(12) United States Patent
Vainstein et al.

(10) Patent No.: US 8,735,650 B2
(45) Date of Patent: May 27, 2014

(54) METHODS OF MODULATING PRODUCTION OF PHENYLPROPANOID COMPOUNDS IN PLANTS

(75) Inventors: Alexander Vainstein, Rechovot (IL); Michal Moyal-Ben-Zvi, Havatselet HaSharon (IL); Ben Rimon-Spitzer, LeHavim (IL)

(73) Assignee: Yissum Research Development Company of the Hebrew University of Jerusalem Ltd., Jerusalem (IL)

(*) Notice: Subject to any disclaimer, the term of this patent is extended or adjusted under 35 U.S.C. 154(b) by 692 days.

(21) Appl. No.: 12/742,707

(22) PCT Filed: Nov. 13, 2008

(86) PCT No.: PCT/IL2008/001490
§ 371 (c)(1),
(2), (4) Date: Aug. 30, 2010

(87) PCT Pub. No.: WO2009/063460
PCT Pub. Date: May 22, 2009

(65) Prior Publication Data
US 2010/0319091 A1    Dec. 16, 2010

Related U.S. Application Data

(60) Provisional application No. 60/987,616, filed on Nov. 13, 2007.

(51) Int. Cl.
*C12N 15/82*    (2006.01)
(52) U.S. Cl.
USPC ........................................... 800/278; 435/468
(58) Field of Classification Search
USPC .......................................................... 800/278
See application file for complete search history.

(56) References Cited

U.S. PATENT DOCUMENTS

| 6,573,432 B1* | 6/2003 | Borevitz et al. ............... 800/295 |
| 7,087,552 B2* | 8/2006 | Blowers et al. ............... 504/114 |
| 2011/0035836 A1* | 2/2011 | Eudes et al. ................... 800/278 |

FOREIGN PATENT DOCUMENTS

| WO | WO 02/00902 | 1/2002 |
| WO | WO 2009/063460 | 5/2009 |

OTHER PUBLICATIONS

Verdonk et al., ODORANT1 Regulates Fragrance Biosynthesis in Petunia Flowers, 17 The Plant Cell, 1612-1624 (2005).*
Stracke et al., Differential regulation of closely related R2R3-MYB transcription factors controls flavonol accumulation in different parts of the *Arabidopsis thaliana* seedling, 50 The Plant Journal, 660-677 (2007).*
Friedberg, Automated protein function prediction-the genomic challenge, 7 Briefings in Bioinformatics, 225-242 at p. 231, top right column (2006).*
Vainstein et al. (Floral Fragrance. New Inroads into an Old Commodity, 127 Plant Physiology, 1383-1389 (2001)).*

(Continued)

*Primary Examiner* — Cynthia Collins
*Assistant Examiner* — Rebecca Coobs

(57) ABSTRACT

A method of enhancing production of a phenylpropanoid compound in a plant or plant cell is disclosed. The method comprising: (a) expressing in the plant or plant cell a heterologous polynucleotide which produces a myb gene of the phenylpropanoid pathway; and (b) contacting the plant or plant cell with at least one substrate of the phenylpropanoid pathway, the substrate being upstream to the production of the phenylpropanoid compound, thereby enhancing the production of a phenylpropanoid compound in the plant or plant cell.

12 Claims, 22 Drawing Sheets
(3 of 22 Drawing Sheet(s) Filed in Color)

(56) References Cited

OTHER PUBLICATIONS

Robertson, VIGS Vectors for Gene Silencing: Many Targets, Many Tools, 55 Annual Review of Plant Biology, 495-519 (2004).*
Burton et al., Virus-induced Silencing of a Plant Cellulose Synthase Gene, 12 The Plant Cell, 691-705 (2000).*
Moyal-Ben-Svi et al., Navigating the Network of Floral Scent Production, XXII International Eucarpia Symposium, Section Ornamentals, Breeding for Beauty ISHS Acta Horticulturae 714 (2006).*
Spitzer et al., Reverse genetics of floral scent: Application of Tobacco Rattle Virus-Based gene silencing in *Petunia*, 145 Plant Physiology, 1241-1250 (2007).*
Uimari et al. (Myb26: a MYB-like protein of pea flowers with affinity for promoters of phenylpropanoid genes, 12 Plant Journal No. 6, 1273-1284 (1997)).*
Communication Relating to the Results of the Partial International Search Dated Apr. 21, 2009 From the International Searching Authority Re.: Application No. PCT/IL2008/001490.
International Search Report Dated Jul. 1, 2009 From the International Searching Authority Re.: Application No. PCT/IL2008/001490.
Written Opinion Dated Jul. 1, 2009 From the International Searching Authority Re.: Application No. PCT/IL2008/001490.
Borevitz et al. "Activation Tagging Identifies A Conserved MYB Regulator of Phenylpropanoid Biosynthesis", The Plant Cell, XP002196250, 12(12): 2383-2393, Dec. 1, 2000. p. 2387-2389.
Moyal Ben Zvi et al. "Interlinking Showy Traits: Co-Engineering of Scent and Colour Biosynthesis in Flowers", Plant Biotechnology Journal, XP002520579, 6(4): 403-415, May 2008.
Xie et al. "Metabolic Engineering of Proanthocyanidins Through Co-Expression of Anthocyanidin Reductase and the PAP1 MYB Transcription Factor", The Plant Journal, XP003012516, 45: 895-907, Jan. 1, 2006. Abstract, p. 897.
International Preliminary Report on Patentability Dated May 18, 2010 From the International Bureau of WIPO Re.: Application No. PCT/IL2008/001490.
International Preliminary Report on Patentability Dated May 27, 2010 From the International Searching Authority Re. Application No. PCT/IL2008/001490.
Communication Pursuant to Article 94(3) EPC Dated Nov. 18, 2011 From the European Patent Office Re. Application No. 08849859.7.

* cited by examiner

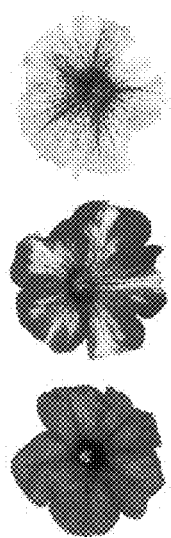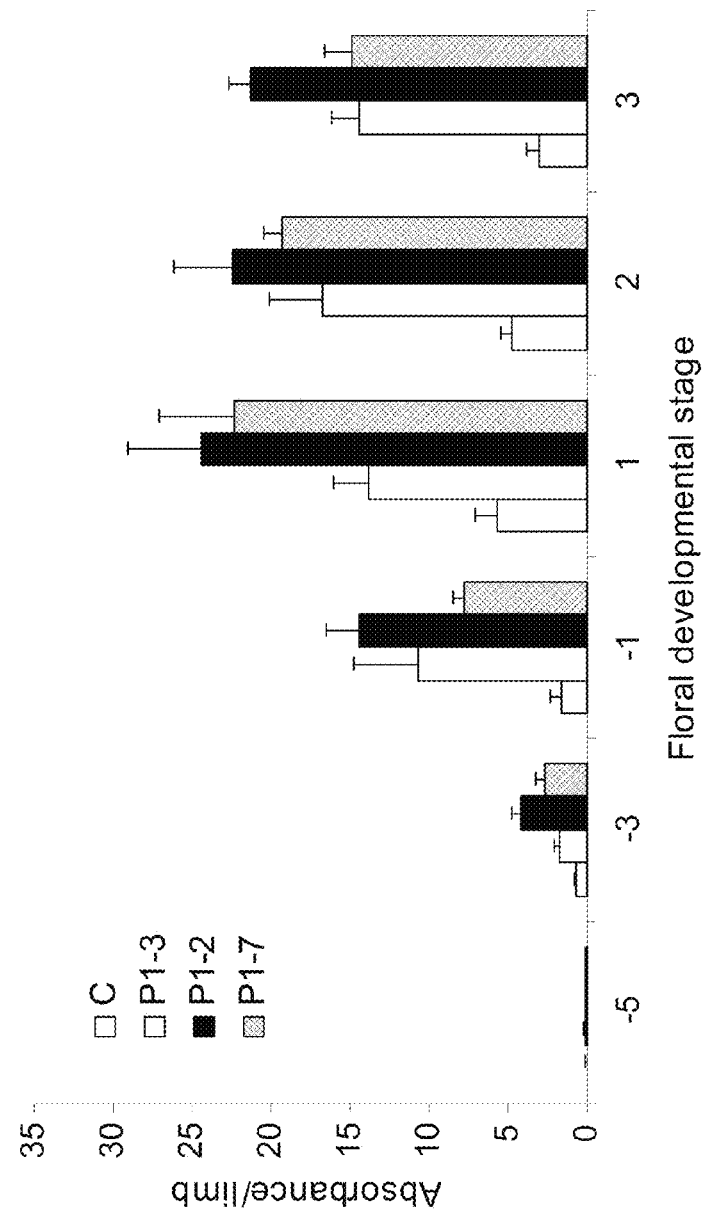
FIG. 1A
FIG. 1B

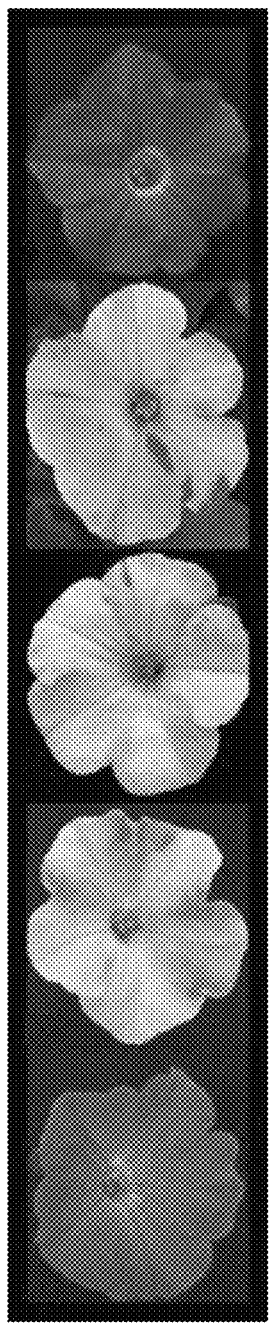
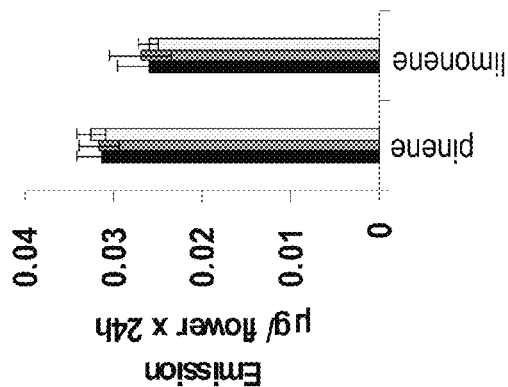
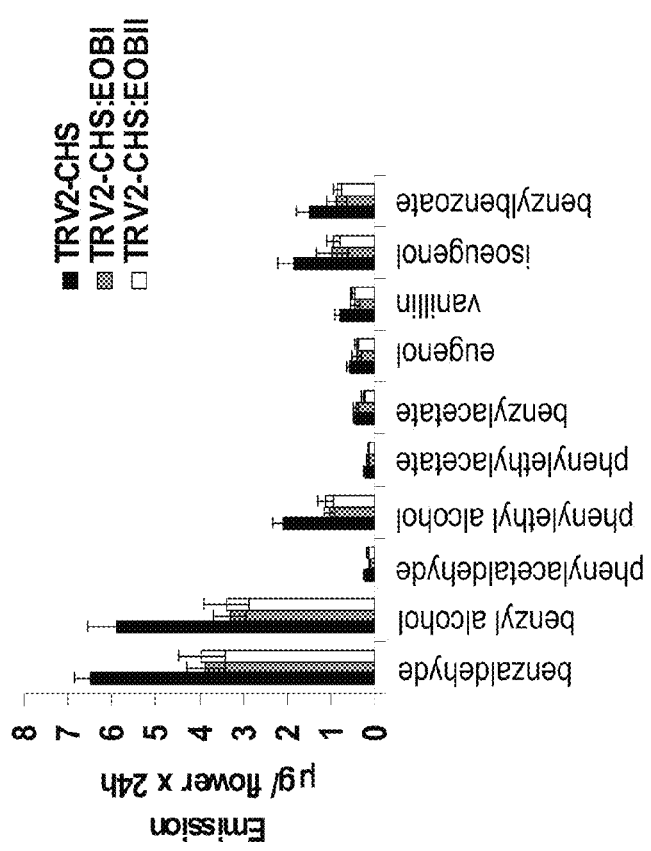
FIG. 9A  FIG. 9B  FIG. 9C  FIG. 9D  FIG. 9E
FIG. 9F
FIG. 9G

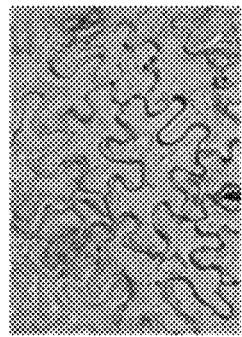
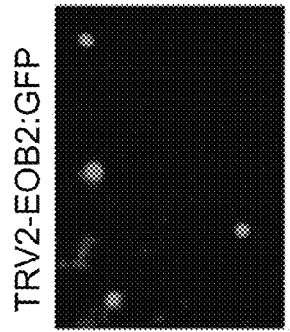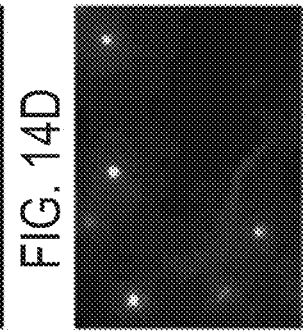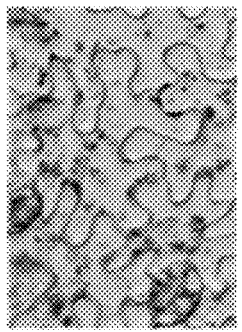
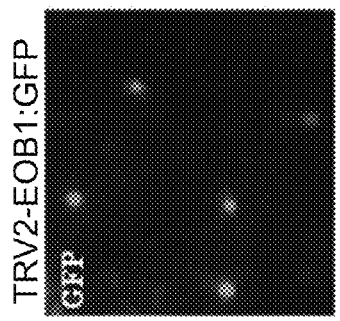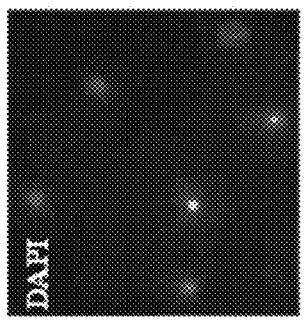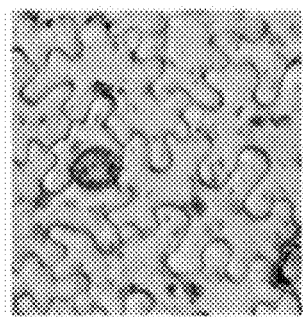

METHODS OF MODULATING PRODUCTION OF PHENYLPROPANOID COMPOUNDS IN PLANTS

RELATED APPLICATIONS

This Application is a National Phase of PCT Patent Application No. PCT/IL2008/001490 having International filing date of Nov. 13, 2008, which claims the benefit of U.S. Provisional Patent Application No. 60/987,616 filed on Nov. 13, 2007. The contents of the above Applications are all incorporated herein by reference.

FIELD AND BACKGROUND OF THE INVENTION

The present invention, in some embodiments thereof, relates to methods of modulating production of phenylpropanoid compounds in plants and, more particularly, but not exclusively, to plant extracts obtained therefrom.

In nature, flower color and fragrance are among the main means adopted by plants to attract pollinators, thereby ensuring plant reproductive success. These characteristics are also commercially important, in that they greatly influence the yield and quality of crops and their commercial appeal.

Flower scent is a composite character determined by a complex mixture of low-molecular-weight volatile molecules, classified by their biosynthetic origin into terpenes, phenylpropanoids and fatty acid derivatives [Chappell, J. and Jones, R. L. (1995) Palo Alto, Calif.: Annual Reviews Inc; Croteau, R. and Karp, F. (1991) In: Perfume: Art, Science and Technology (Lamparsky, D. and Müller, M., eds), pp. 101-126. New York: Elsevier Applied Sciences; Dudareva, N., et al. (2004) Plant Physiol. 135: 1893-1902]. Several structural genes responsible for the formation of volatile compounds have been identified [Schuurink, et al. (2006) Trends Plant Sci. 11: 20-25; van Schie, et al. (2006) Curr. Opin. Plant Biol. 9: 203-208], including genes responsible for the formation of volatile phenylpropanoid and benzenoid compound [Boatright, et al. (2004) Plant Physiol. 135: 1993-2011; Dexter, et al. (2007) Plant J. 49: 265-275; Kaminaga, et al. (2006) J. Biol. Chem. 281: 23357-23366; Tieman, et al. (2006) Proc. Natl. Acad. Sci. USA, 103: 8287-8292], however the precise biochemical steps determining the pathway are still largely unknown (Boatright et al., supra; Schuurink et al., supra). A moderate increase in volatile terpenoid production has been previously achieved in flowers and fruits via ectopic expression of specific structural genes e.g. basil geraniol synthase, tobacco limonene, γ-terpinene and β-pinene synthase, clarkia linalool synthase, strawberry linalool/nerolidol symthase [Davidovich-Rikanati, et al. (2007) Nat. 25: 899-901; Lucker, et al. (2006) In: Biology of Floral Scent (Dudareva, N. and Pichersky, E., eds), pp. 321-338. Boca Raton, Fla.: CRC Press].

Engineering of floral scent is often limited by a shortage of substrate availability, which restricts metabolic flow [Lucker et al., supra; Schwab, W. (2003) Phytochemistry, 62: 837-849]. Moreover, volatile production in plants often has a rhythmic pattern, and is thus limited to a certain period of the day. For example, in *Petunia axillaris*, rhythmus of volatile production is nocturnal, and has been reported as both circadian and light controlled [Schuurink et al., supra; Underwood, et al. (2005) Plant Physiol. 138: 255-266; Verdonk et al. (2003) Phytochemistry, 62: 997-1008]. One way to increase floral scent production is to use transcription factors that control multiple steps in various branches of the pathway [Koes et al. (2005) Trends Plant Sci. 10: 236-242; Mahmoud and Croteau (2002) Trends Plant Sci. 7: 366-373; Pichersky and Dudareva (2007) Trends Biotechnol. 25, 105-110], for example, the transcription factor ODORANT1 which has been shown to be involved in the regulation of volatile biosynthesis in flowers, however, its ability to boost metabolic flow toward scent production remains to be investigated [Verdonk et al. (2005) Plant Cell, 17: 1612-1624].

Another class of metabolites determining showy traits is the anthocyanin pigments which are derived from a well-defined branch of the phenylpropanoid pathway. Numerous structural as well as regulatory genes involved in anthocyanin biosynthesis have been extensively used for the genetic manipulation of flower color e.g. chalcone synthase (Chs), chalcone isomerase (Chi), flavanone 3 hydroxylase (F3h), flavonoid 3'-hydroxylase (F3'h), flavonoid 3'5'-hydroxylase (F3'5'h), flavonol synthase (Fls), flavone synthase (Fns), dihydroflavonol 4-reductase (Dfr), anthocyanidin synthase (Ans), anthocyanidin 3-rutinoside acyltransferase (Ar-at), anthocyanidin 3-glucosyltransferase (3Gt), anthocyanidin 3'-glucosyltransferase (3'Gt), anthocyanidin 3-glucoside glucosyltransferase (3Ggt), anthocyanin 3-hydroxycinnamoyltransferase (3Hat), anthocyanin 3-malonyltransferase (3Mat), anthocyanidin 3-glucoside rhamnosyltransferase (3Rt), maize leaf colour (Lc) and C1, snapdragon Delila [Chandler et al. (2007) Critical Reviews in Plant Sciences, 26(4): 169-197; Winkel-Shirley (2001) Plant Physiol. 126: 485-493]. The regulation of anthocyanin biosynthesis has been shown to occur primarily through the action of Myb transcription factors (Koes et al., supra). However, the activities of some of these regulators are not restricted to the anthocyanin shunt. For example, Pap1 (Production of Anthocyanin Pigment 1) Myb transcription factor from *Arabidopsis thaliana* regulates the production of various non-volatile compounds via regulation of several dozens of genes belonging to the phenylpropanoid pathway [Borevitz, et al. (2000) Plant Cell 12: 2383-2393; Harmer et al. (2000) Science 290: 2110-2113; Sharma and Dixon (2005) Plant J. 44: 62-75; Tohge et al. (2005) Plant J. 42: 218-235; Xie et al. (2006) Plant J. 45: 895-907]. For example, in *Arabidopsis*, overexpression of Pap1 results in the accumulation of lignin, hydroxycinnamic acid esters and flavonoids including anthocyanins, which impart a prominent purple color to plant organs (Borevitz et al., supra).

U.S. Pat. No. 7,087,552 discloses methods for creating, manipulating, modifying and enhancing floral scent in plants and cut flowers by modifying the biosynthesis and/or emission of floral scent from a plant and/or plant cutting. U.S. Pat. No. 7,087,552 teaches applying to the plant or flower a composition containing a floral scent precursor such as benzoic acid, phenylalanine, trans-cinnamic acid, benzylalcohol, salicylic acid, geranyl pyrophosphate, farnesyl pyrophosphate, jasmonic acid, eugenol or isoeugenol.

U.S. Pat. No. 5,283,184 discloses methods and compositions for producing plants (e.g. *Petunia* and Chrysanthemum) exhibiting one or more desired phenotypic or genotypic traits (e.g. reduction in color intensity, an altered pattern color, or a change in basic color of the plant flowers or other plant organs) by introducing into the plant cell a nucleic acid fragment (e.g., a flavonoid biosynthetic pathway gene sequence) that is transcribed to yield a mRNA transcript substantially homologous to the gene's transcript.

U.S. Pat. Appl. No. 20050289662 discloses genetically modified plants comprising a reporter system capable of directly monitoring a phenotypic trait in a plant (e.g. soil pollution). The reporter system for plants according to the teachings of U.S. Pat. Appl. No. 20050289662 may comprise an altered expression (e.g. overexpression) of transcription factors containing a Myb domain such as PAP1 and/or PAP2.

U.S. Pat. Appl. No. 20040128711 discloses method and compositions for the modulation of flavanone and/or isoflavone production in plants by introducing a transgene encoding the PAP1 gene into the plant.

SUMMARY OF THE INVENTION

According to an aspect of some embodiments of the present invention there is provided a method of enhancing production of a phenylpropanoid compound in a plant or plant cell, the method comprising: (a) expressing in the plant or plant cell a heterologous polynucleotide which produces a myb gene of the phenylpropanoid pathway; and (b) contacting the plant or plant cell with at least one substrate of the phenylpropanoid pathway, the substrate being upstream to the production of the phenylpropanoid compound, thereby enhancing the production of a phenylpropanoid compound in the plant or plant cell.

According to an aspect of some embodiments of the present invention there is provided a method of enhancing production of a phenylpropanoid compound in a plant or plant cell, the method comprising: (a) expressing in the plant or plant cell a heterologous polynucleotide which produces a myb gene of the phenylpropanoid pathway; and (b) expressing in the plant or plant cell an enzyme capable of producing at least one substrate of the phenylpropanoid pathway, the substrate being upstream to the production of the phenylpropanoid compound, thereby enhancing the production of a phenylpropanoid compound in the plant or plant cell.

According to an aspect of some embodiments of the present invention there is provided a method of enhancing production of a phenylpropanoid compound in a plant or plant cell, the method comprising expressing in the plant or plant cell a heterologous polynucleotide which produces a myb gene of the phenylpropanoid pathway as set forth in SEQ ID NO: 51 or 53, thereby enhancing the production of the phenylpropanoid compound in the plant or plant cell.

According to some embodiments of the invention, the method further comprising contacting the plant or plant cell with at least one substrate of the phenylpropanoid pathway, the substrate being upstream to the production of the phenylpropanoid compound, thereby enhancing the production of the phenylpropanoid compound in the plant or plant cell.

According to some embodiments of the invention, the method further comprising expressing in the plant or plant cell an enzyme capable of producing at least one substrate of the phenylpropanoid pathway, the substrate being upstream to the production of the phenylpropanoid compound, thereby enhancing the production of the phenylpropanoid compound in the plant or plant cell.

According to an aspect of some embodiments of the present invention there is provided a method of reducing production of a phenylpropanoid compound in a plant or plant cell, the method comprising downregulating expression of a myb gene of the phenylpropanoid pathway in the plant or plant cell, thereby reducing production of the phenylpropanoid compound in the plant or plant cell.

According to some embodiments of the invention, the downregulating is effected by expressing in the plant or plant cell an isolated polynucleotide comprising a nucleic acid sequence at least 80% homologous to SEQ ID NOs: 55 or 56.

According to some embodiments of the invention, the phenylpropanoid compound is a volatile compound.

According to some embodiments of the invention, the volatile compound is selected from the group consisting of a phenylacetaldehyde, a benzaldehyde, a benzyl alcohol, a phenylethyl alcohol, a phenylethyl acetate, a benzyl acetate, an eugenol, a vanillin, a benzylbenzoate, a methylbenzoate, an isoeugenol, a benzaldehyde 4-hydroxy, a benzaldehyde 3,4-dimethoxy, a benzaldehyde 4-hydroxy 3-methoxy, an orcinol methyl ether, an orcinol dimethyl ether, a methyleugenol, an isomethyleugenol, a methylsalicylate, and a 3,5-dimethoxytoluene.

According to some embodiments of the invention, the phenylpropanoid compound is a non-volatile compound.

According to some embodiments of the invention, the non-volatile compound is selected from the group consisting of an anthocyanin, a proanthocyanin, a stilbene, a flavonoid, a chalcone, an aurone, a flavone and a flavonol.

According to some embodiments of the invention, the heterologous polynucleotide comprises a nucleic acid sequence at least 80% homologous to SEQ ID NOs: 1, 51 or 53.

According to some embodiments of the invention, the heterologous polynucleotide comprises a nucleic acid sequence encoding a polypeptide having an amino acid sequence at least 80% homologous to SEQ ID NOs: 2, 52 or 54.

According to some embodiments of the invention, the myb gene comprises an amino acid sequence endogenous to the plant.

According to some embodiments of the invention, the at least one substrate is selected from the group consisting of phenylalanine, cinnamic acid, benzoic acid, coumarin acid, orcinol, salicylic acid, coniferyl alcohol, coniferyl acetate and ferrulic acid.

According to some embodiments of the invention, the method step (a) and/or (b) is effected during night hours.

According to some embodiments of the invention, the method step (a) and/or (b) is effected during day hours.

According to some embodiments of the invention, the production of the phenylpropanoid compound is constant during day and night following (a) and/or (b).

According to some embodiments of the invention, the method step (a) and/or (b) is effected during a predetermined developmental stage.

According to some embodiments of the invention, the method step (a) and/or (b) is effected in a tissue specific manner.

According to some embodiments of the invention, expressing in the plant or plant cell an enzyme capable of producing at least one substrate is effected by expressing in the plant or plant cell at least one polynucleotide which encodes for an enzyme which catalyzes biosynthesis of the substrate.

According to some embodiments of the invention, the enzyme selected from the group consisting of a prephenate dehydratase (PDT), a chorismate mutase (CM), a prephenate aminotransferase (PAT), an arogenate dehydratase (ADT) and a cyclohexadienyl dehydratase (CDT).

According to some embodiments of the invention, the plant is a *Petunia*.

According to some embodiments of the invention, the production of the phenylpropanoid compound in the plant or plant cell is enhanced by at least 3 fold.

According to an aspect of some embodiments of the present invention there is provided an isolated polynucleotide for down-regulating expression of a myb gene of the phenylpropanoid pathway in a plant.

According to some embodiments of the invention, the isolated polynucleotide being selected from the group consisting of SEQ ID NOs: 55 or 56.

According to an aspect of some embodiments of the present invention there is provided a nucleic acid expression construct comprising a nucleic acid sequence expressing the isolated polynucleotide of claim 25 or 26.

According to an aspect of some embodiments of the present invention there is provided a genetically modified plant or plant cell comprising the isolated polynucleotide of claim 25-27.

According to an aspect of some embodiments of the present invention there is provided a nucleic acid construct comprising a first nucleic acid sequence encoding a myb gene of the phenylpropanoid pathway and a second nucleic acid sequence encoding a gene for catalyzing biosynthesis of at least one substrate of the phenylpropanoid pathway, wherein the first nucleic acid sequence and the second nucleic acid sequence are under transcription control of at least one cis-acting regulatory element.

According to an aspect of some embodiments of the present invention there is provided a nucleic acid construct system comprising: (i) a first nucleic acid construct comprising a first nucleic acid sequence encoding a myb gene of the phenylpropanoid pathway; and (ii) a second nucleic acid construct comprising a second nucleic acid sequence encoding a gene for catalyzing biosynthesis of at least one substrate of the phenylpropanoid pathway; wherein the first nucleic acid sequence and the second nucleic acid sequence are under transcription control of a cis-acting regulatory element.

According to an aspect of some embodiments of the present invention there is provided a genetically modified scent emitting plant exhibiting constant scent emission which is at least as high as that produced from a non-genetically modified plant of the same species during high scent emission hours.

According to some embodiments of the invention, the genetically modified scent emitting plant comprising the nucleic acid construct of claim 29.

According to some embodiments of the invention, the genetically modified scent emitting plant comprising the nucleic acid construct system of claim 30.

According to an aspect of some embodiments of the present invention there is provided a method of plant and plant cell extraction, the method comprising: (a) expressing in the plant or plant cell a heterologous polynucleotide which produces a myb gene of the phenylpropanoid pathway; and (b) isolating a phenylpropanoid compound-containing fraction from the plant or plant cell expressing the myb gene.

According to an aspect of some embodiments of the present invention there is provided an isolated plant fraction having a phenylpropanoid compound profile as that of FIG. 2E closed bars.

According to some embodiments of the invention, the phenylpropanoid compound is volatile.

According to an aspect of some embodiments of the present invention there is provided an isolated polynucleotide comprising a nucleic acid sequence encoding the polypeptide set forth in SEQ ID NO: 59.

According to an aspect of some embodiments of the present invention there is provided an isolated polynucleotide comprising a nucleic acid sequence encoding the polypeptide set forth in SEQ ID NO: 52.

According to an aspect of some embodiments of the present invention there is provided an isolated polynucleotide comprising a nucleic acid sequence encoding the polypeptide set forth in SEQ ID NO: 54.

According to an aspect of some embodiments of the present invention there is provided an isolated polynucleotide comprising the nucleic acid sequence set forth in SEQ ID NO: 51.

According to an aspect of some embodiments of the present invention there is provided an isolated polynucleotide comprising the nucleic acid sequence set forth in SEQ ID NO: 53.

According to an aspect of some embodiments of the present invention there is provided an isolated polypeptide comprising the amino acid sequence set forth in SEQ ID NO: 59.

According to an aspect of some embodiments of the present invention there is provided an isolated polypeptide comprising the amino acid sequence set forth in SEQ ID NO: 52.

According to an aspect of some embodiments of the present invention there is provided an isolated polypeptide comprising the amino acid sequence set forth in SEQ ID NO: 54.

According to an aspect of some embodiments of the present invention there is provided a nucleic acid construct comprising the isolated polynucleotide of claim 37-41 under transcription control of a cis-acting regulatory element.

According to an aspect of some embodiments of the present invention there is provided a genetically modified plant or plant cell comprising the nucleic acid construct of claim 45.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-B depict increased pigmentation in *petunia* flowers expressing CaMV 35S-driven Pap1. FIG. 1A shows flowers of Pap1-transgenic *petunia* lines P1-2, P1-7 and control flowers (from left to right, respectively); and FIG. 1B is a bar graph showing anthocyanin content in corolla limbs of control (depicted as C) and Pap1-transgenic lines P1-3, 2 and 7. Limbs of flowers at different developmental stages [from 5 days before anthesis (−5) to 3 days post-anthesis (3)] were collected, and anthocyanin was extracted and estimated using the formula Absorbance=$A_{530}$-0.25 $A_{657}$. Each graph represents the average of three independent experiments. Standard errors are indicated by vertical bars.

Figure 2A:
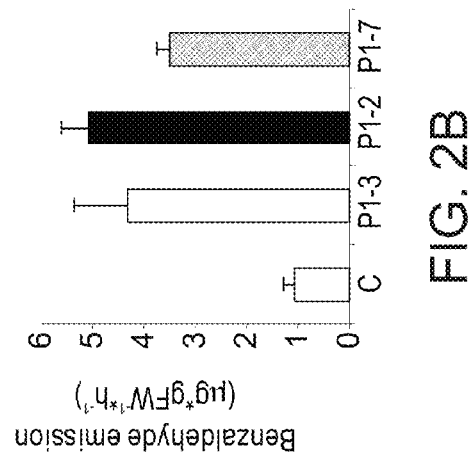
Figure 2B:
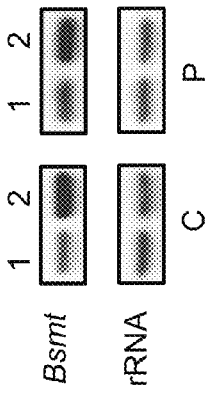
Figure 2C:
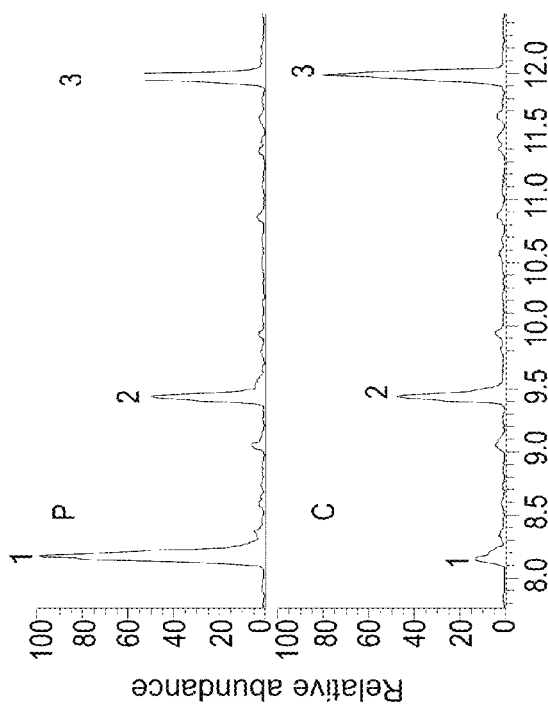
Figure 2D:
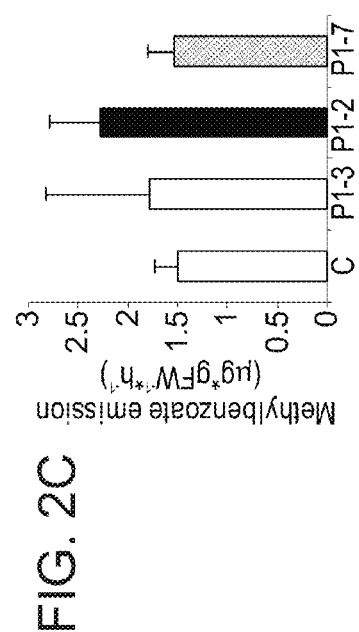
Figure 2E:
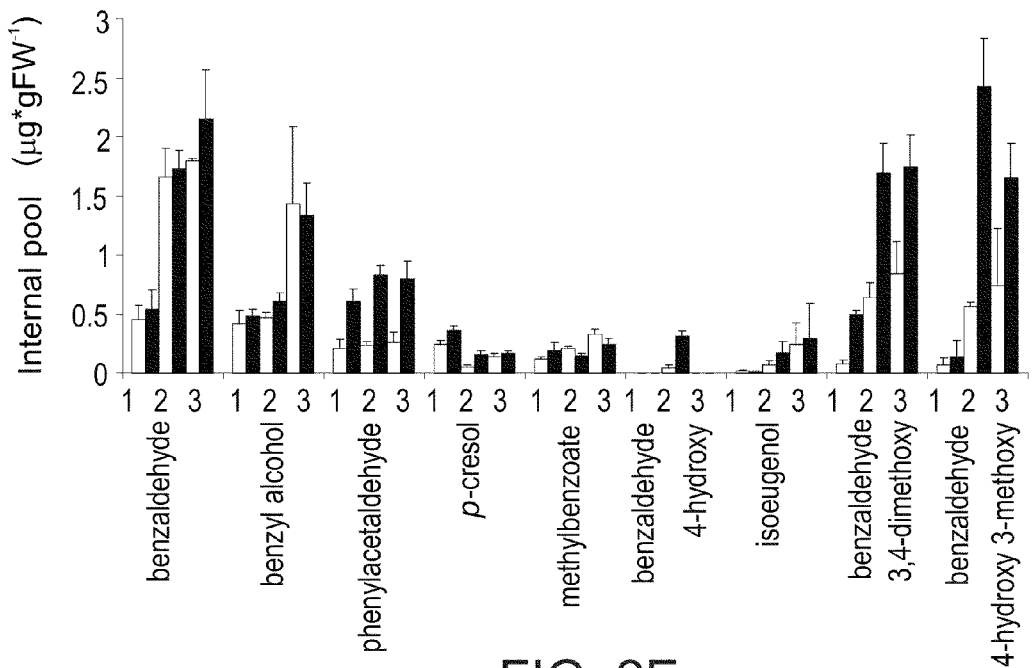
Figure 2F:
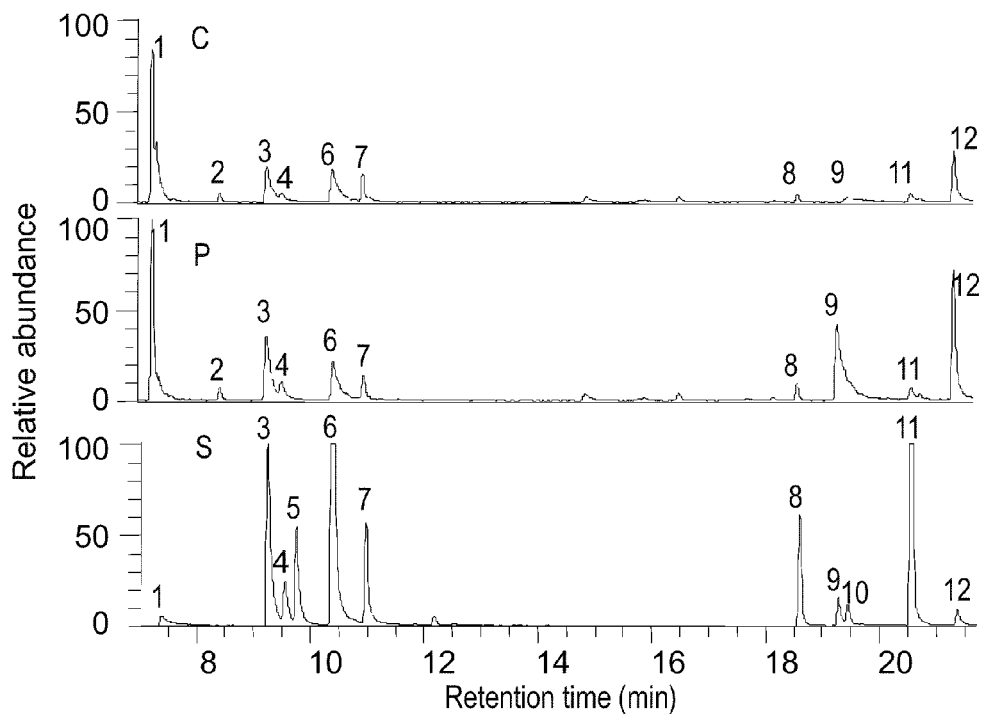

FIGS. 2A-F depict increased scent production in *petunia* flowers expressing Pap1. FIG. 2A is a representative chromatogram of volatiles emitted from control (depicted by C) and Pap1-transgenic line 2 (depicted by P) *petunia* flowers as determined using the dynamic headspace technique. Analysis was conducted for 12 hours during the first night post-anthesis. 1—benzaldehyde, 2—iso-butylbenzene (internal standard), 3—methylbenzoate; FIG. 2B depicts levels of benzaldehyde emitted from flowers of control (depicted by C) and Pap1-transgenic lines (P1-3, 2 and 7). Each graph represents the average of three independent experiments. Standard errors are indicated by vertical bars; FIG. 2C depicts levels of methylbenzoate emitted from flowers of control (depicted by C) and Pap1-transgenic lines (P1-3, 2 and 7) as determined using the dynamic headspace technique. Analysis was conducted for 12 hours during the first night post-anthesis. Each graph represents the average of three independent experiments with standard errors indicated by vertical bars; FIG. 2D depicts RNA-blot analysis of S-adenosyl-L-methionine:benzoic acid/salicylic acid carboxyl methyltransferase (Bsmt) levels in limbs [first (1) and second (2) day post-anthesis] of control (depicted by C) and Pap1-transgenic line 2 (depicted by P). The blot was rehybridized with an 18S rRNA probe to ensure equal loading of samples; FIG. 2E depicts internal pools of volatile compounds accumulated in control (depicted by white bars) and Pap1-transgenic line 2 (depicted by black bars) limbs. Limbs of flowers at different developmental stages [from first to third days (1-3) post-anthesis] were analyzed. Each graph represents the average of three independent experiments with standard errors indicated by vertical bars; and FIG. 2F is a representative chromatogram of volatile compounds accumulating in limbs of Pap1-transgenic line 2 (depicted by P) and control (depicted by C) *petunia* flowers. Chromatogram of authentic standards (depicted by S) of volatile compounds is shown. 1—benzaldehyde, 2—iso-butylbenzene (internal standard), 3—benzyl alcohol, 4—phenylacetaldehyde, 5—o-cresol, 6—p-cresol, 7—methylbenzoate, 8—benzaldehyde 4-hydroxy, 9—benzaldehyde 4-hydroxy 3-methoxy, 10—eugenol, 11—isoeugenol, 12—benzaldehyde 3,4-dimethoxy.

Figure 3:
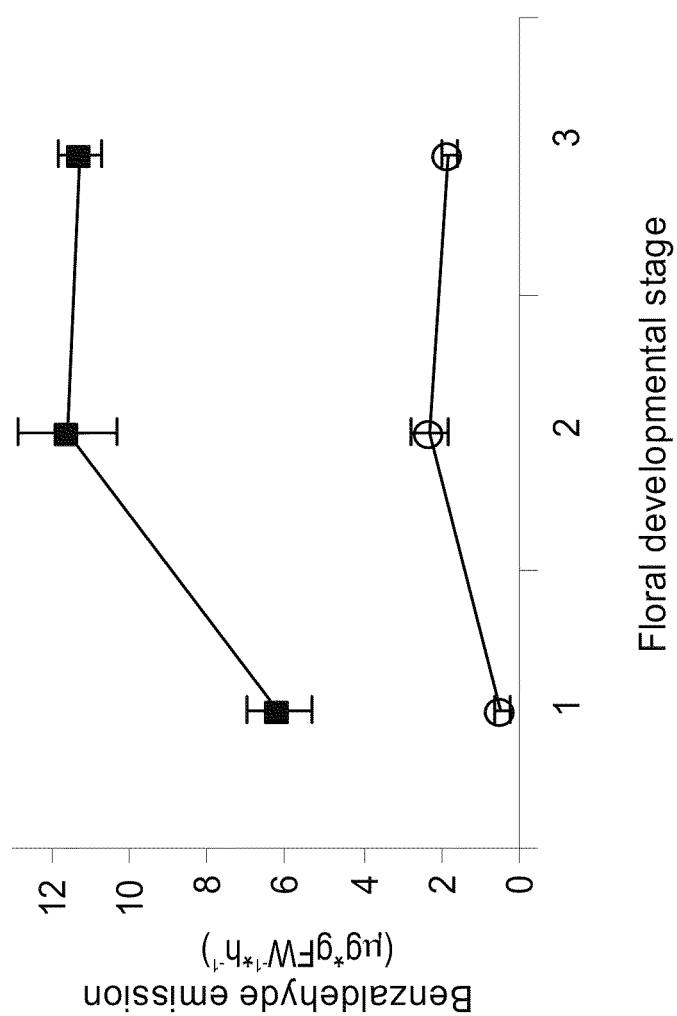

FIG. 3 is a line graph depicting developmental profiles of benzaldehyde emission in control and Pap1-transgenic *petunia* flowers. Levels of benzaldehyde emission from flowers of control (depicted by circles) and flowers of Pap1-transgenic line 2 (depicted by squares) at different developmental stages as determined using the dynamic headspace technique. Analysis was conducted for 12 hours using flowers during the first, second and third night post-anthesis (1, 2 and 3, respectively). Each point is the average of three independent experiments. Standard errors are indicated by vertical bars.

Figure 4A:
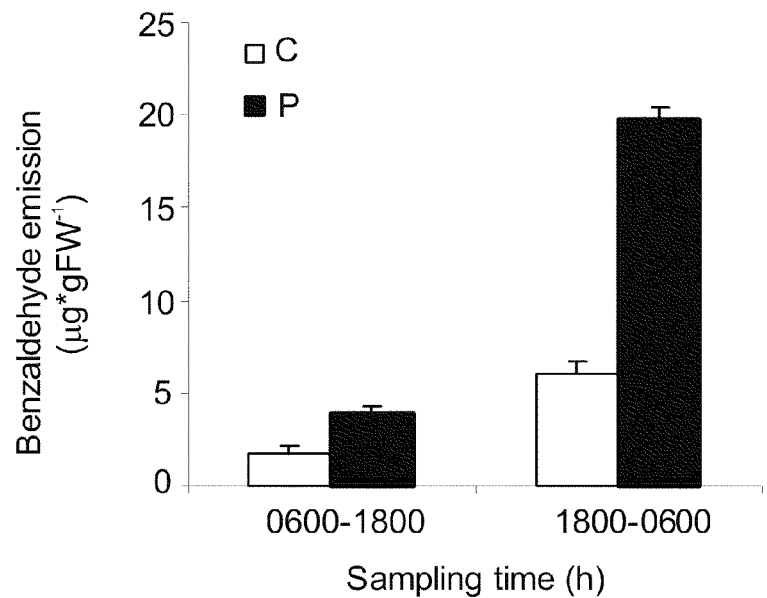
Figure 4B:
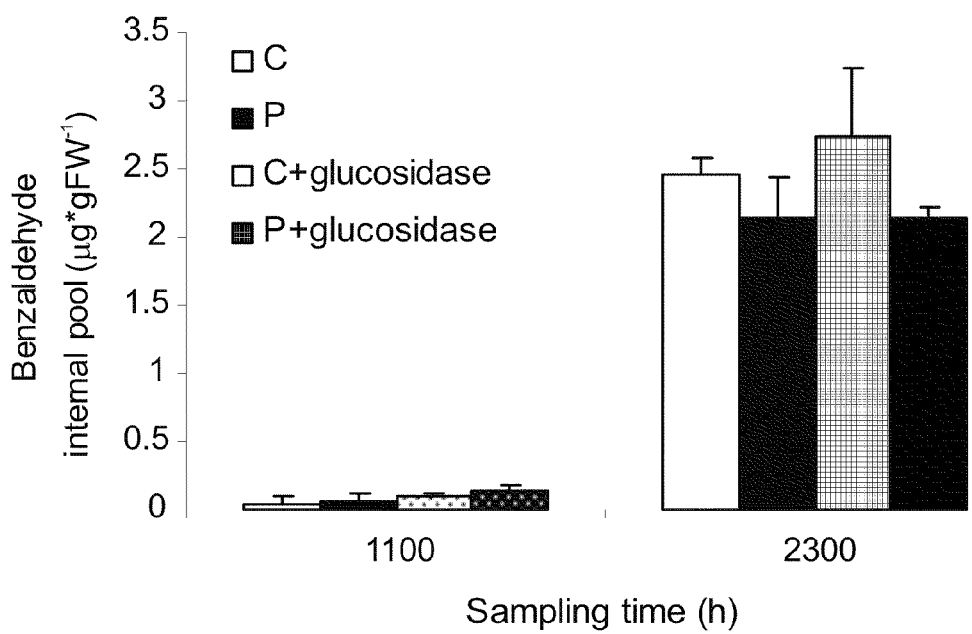

FIGS. 4A-B are bar graphs depicting benzaldehyde production during a day/night cycle in control and Pap1-transgenic *petunia* flowers. FIG. 4A depicts the levels of benzaldehyde emission from control flowers (depicted by C) and Pap1-transgenic line 2 flowers (depicted by P) two days post-anthesis as determined using the dynamic headspace technique. Headspace collections were performed during the day for 12 hours under light conditions (0600-1800 hours) and during the night for 12 hours under dark conditions (1800-0600 hours); and FIG. 4B depicts determination of internal pools of benzaldehyde. Free and total (following glucosidase treatment) pools of benzaldehyde were assayed in limbs collected during the day (1100 h) and night (2300 h) using extraction with hexane. Each graph is the average of three independent experiments. Standard errors are indicated by vertical bars.

Figures 5A, 5B, 5C, 5D:
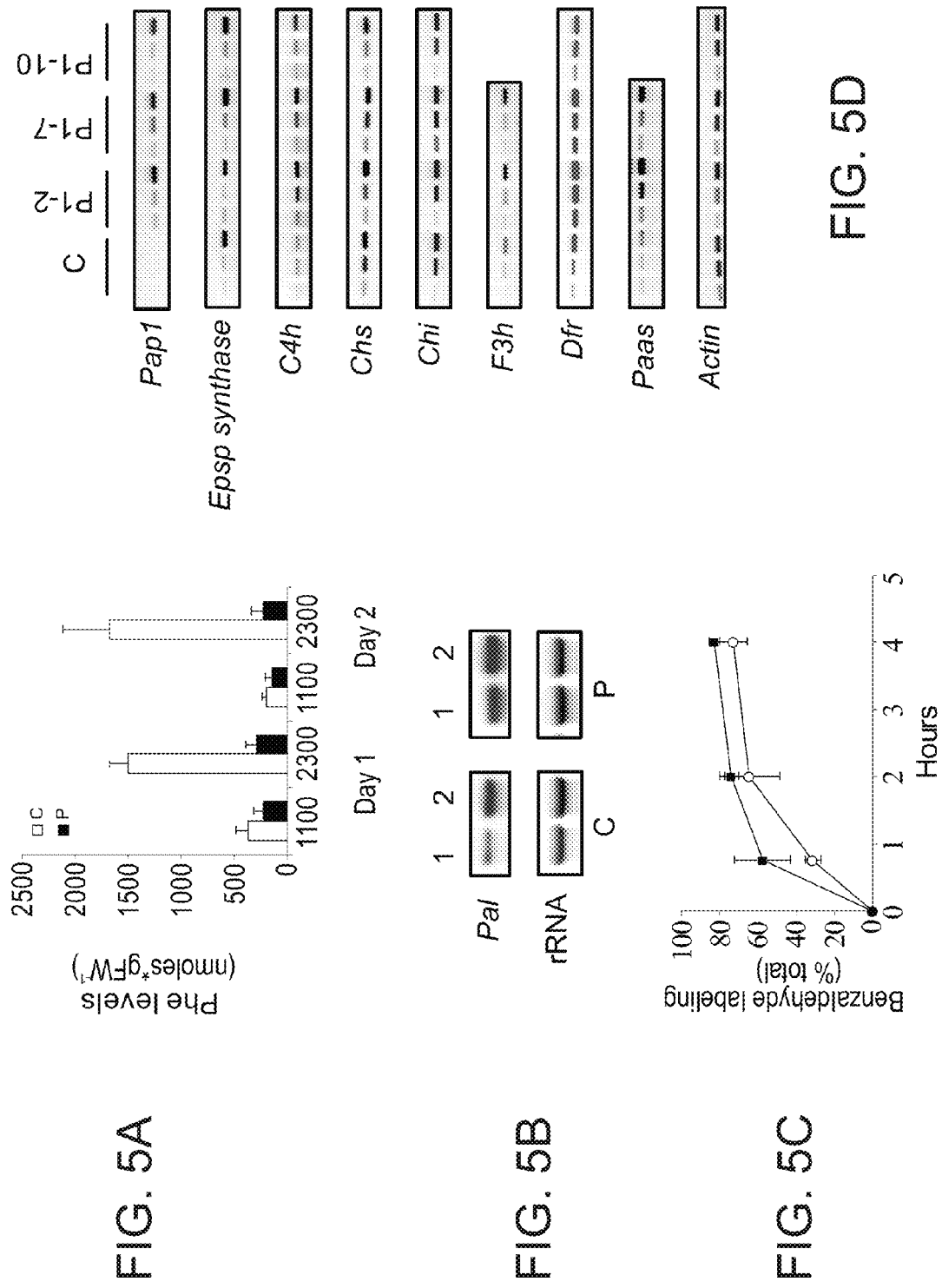

FIGS. 5A-D depict increased activation of the phenylpropanoid pathway in *petunia* flowers expressing Pap1. FIG. 5A depicts levels of Phe in limbs of control (depicted by C) and Pap1-transgenic line 2 (depicted by P). Petunias were analyzed during the day (1100 hour) and night (2300 hour) on the first and second days post-anthesis; FIG. 5B depicts RNA-blot analysis of phenylalanine ammonia lyase (Pa1) levels in limbs [first (1) and second (2) day post-anthesis] of control (C) and Pap1-transgenic line 2 (P) *petunia* flowers; FIG. 5C depicts in-vivo labeling kinetics of benzaldehyde in control and Pap1-transgenic *petunia* flowers. Volatiles, emitted from excised corolla limbs (collected at 2300 hour) fed with $^2H_5$-Phe [control (depicted by open circles) and Pap1-transgenic line 2 (depicted by closed squares)] were sampled for 0.75, 2 and 4 hours, and the total amount and isotope abundance of benzaldehyde were analyzed by GC-MS; FIG. 5D depicts semi-quantitative RT-PCR analysis showing the expression of genes from the phenylpropanoid pathway in Pap1-transgenic and control *petunia* flowers. cDNA prepared from total RNA isolated from limbs of control (depicted by C) and three Pap1-transgenic lines (P1-2, P1-7 and P1-10) was used for PCR amplification of specific genes. For each sample, three amplification products (following 26, 28 and 30 cycles of PCR from left to right) are shown. Ethidium bromide-stained agarose gels show RT-PCR products.

Figure 6A:
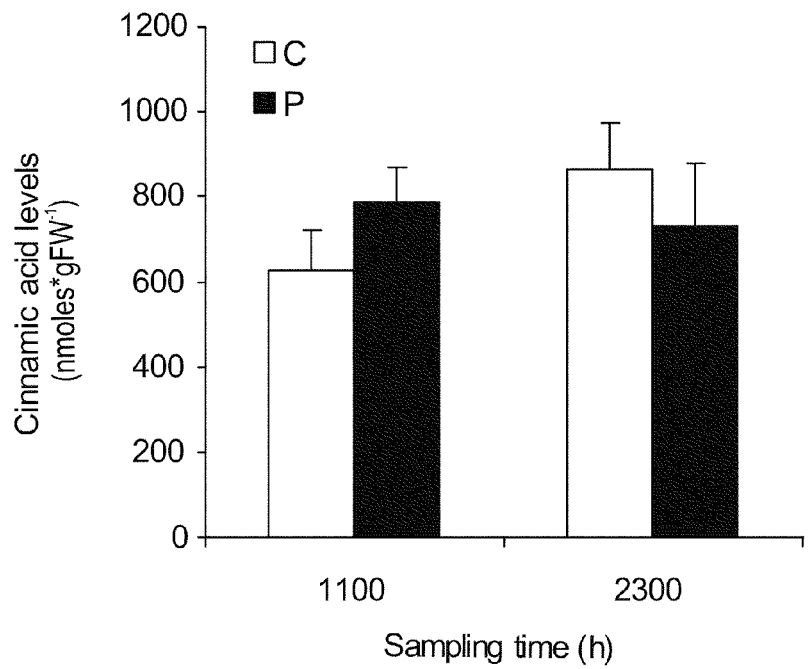
Figure 6B:
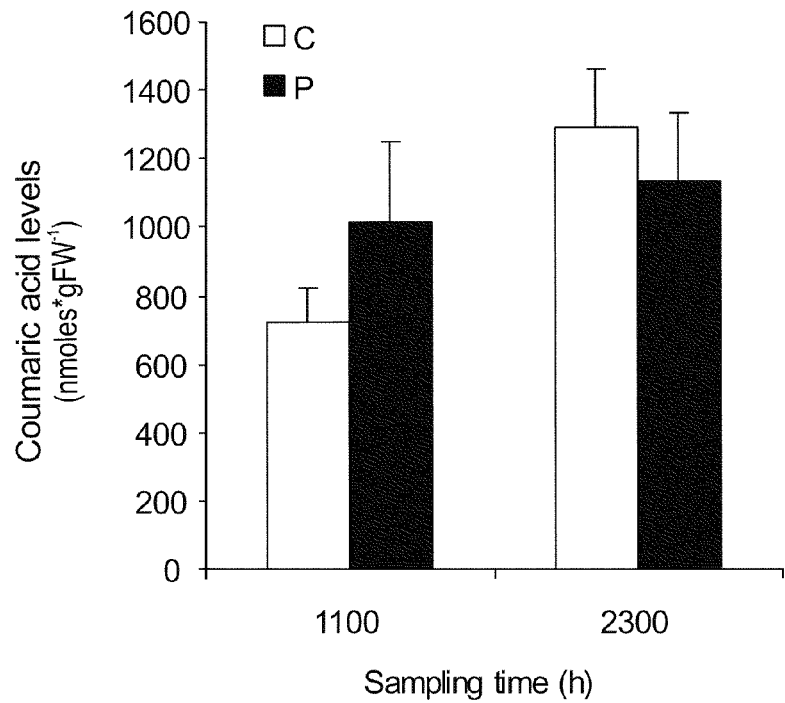

FIGS. 6A-B depict pools of cinnamic acid (FIG. 6A) and coumaric acid (FIG. 6B) in control and Pap1-transgenic *petunia* flowers. Levels of cinnamic and coumaric acid in limbs of control (depicted by C) and Pap1-transgenic line 2 (depicted by P) *petunia* were analyzed during the day (1100 hour) and night (2300 hour) on the first day post-anthesis. Each graph represents an average of results from at least three independent experiments. Standard errors are indicated by vertical bars.

Figure 7A:
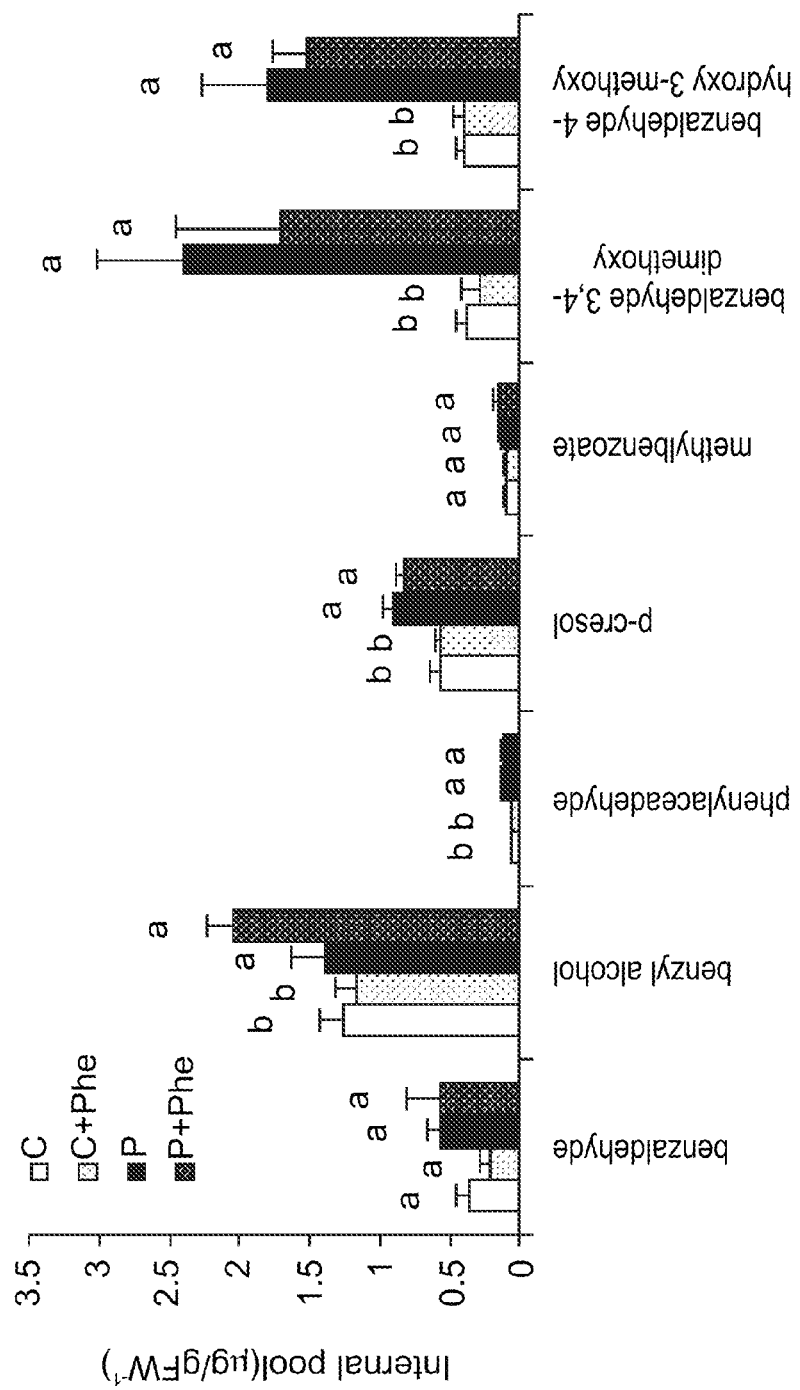
Figure 7C:
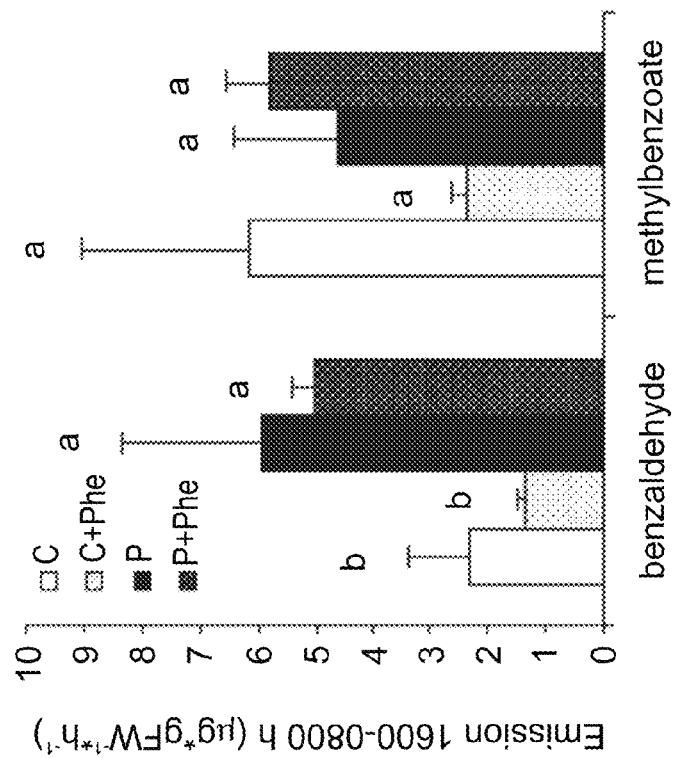
Figure 7B:
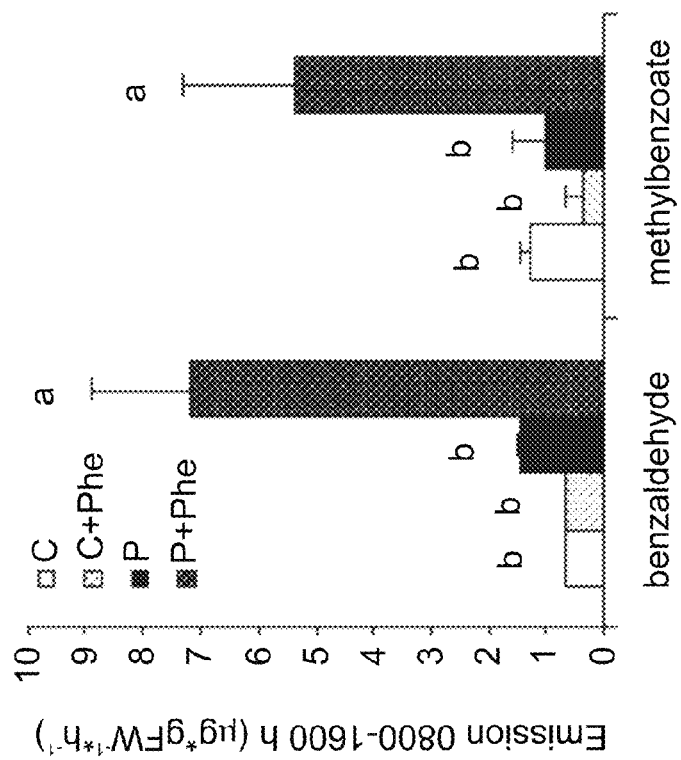

FIGS. 7A-C depict the effect of phenylalanine (Phe) feeding on volatile production in Pap1-transgenic and control flowers. FIG. 7A is a bar graph depicting the internal pools of volatile compounds accumulated in control (depicted by C) and Pap1-transgenic line 2 (depicted by P) limbs with (+Phe) or without feeding with phenylalanine Flowers were collected at 1600 hour, placed in a glass vial containing 10 ml of water with or without L-phenylalanine and at 2300 hour volatile were extracted. FW, fresh weight; FIGS. 7B-C are bar graphs depicting the levels of benzaldehyde and methylbenzoate emitted from control (depicted by C) and Pap1-transgenic line 2 (depicted by P) flowers with (+Phe) or without feeding with Phe. The headspace was collected during the day (0800-1600 h) (FIG. 7B) and night (1600-0800 h) (FIG. 7C). Columns represent the mean values of independent experiments (n=3). Standard errors are indicated by vertical bars. The significance of the differences in the internal pools of volatile compounds (FIG. 7A) and in the emission levels of volatile compounds between Pap1-transgenic line 2 and control non-transgenic flowers with or without Phe feeding during the day (FIG. 7B) or night (FIG. 7C) was calculated using Tukey's all pairwise multiple comparison procedure following two-way analysis of variance (ANOVA), conducted separately for each compound. Values with different letters are significantly different (P<0.05).

Figure 8:
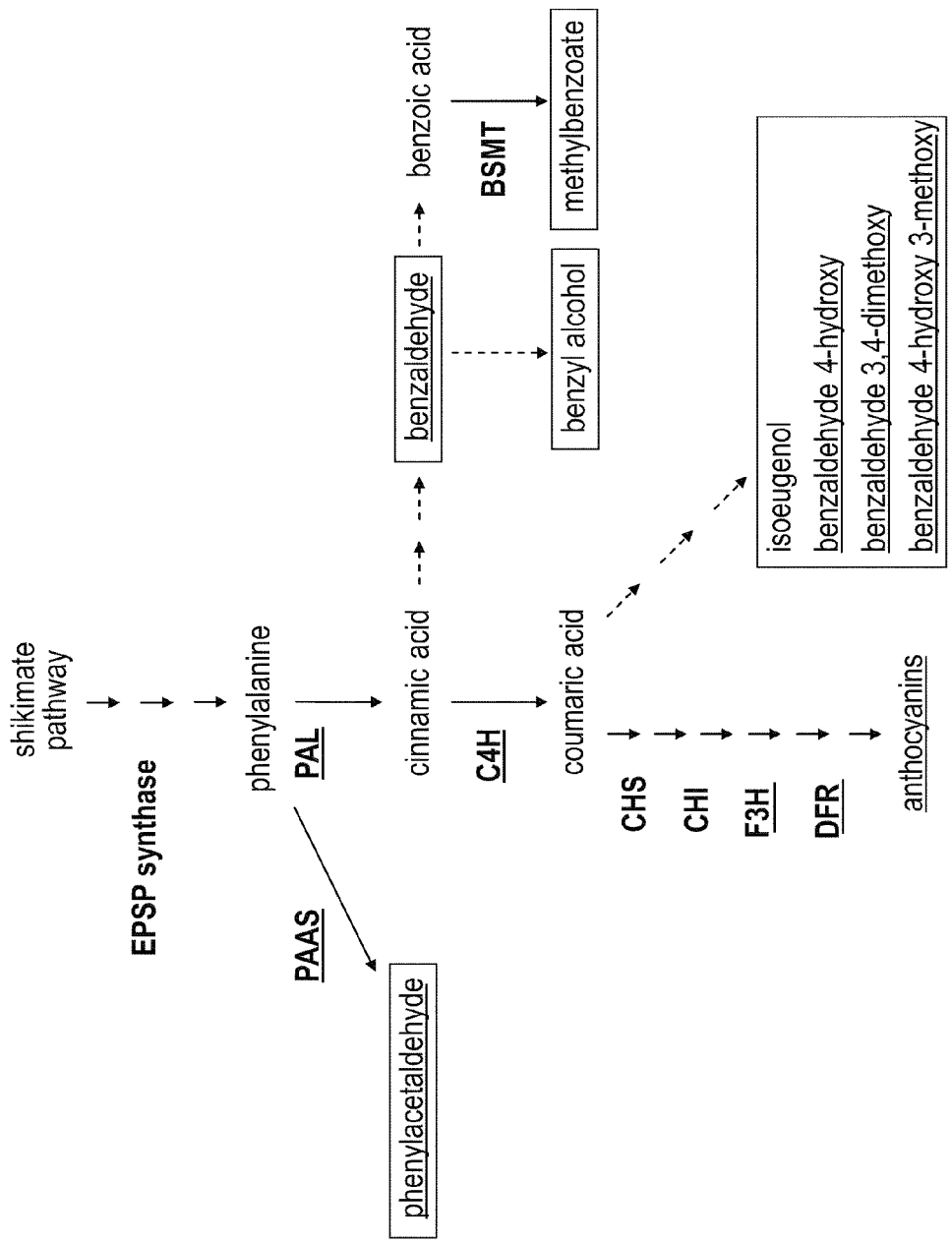

FIG. 8 is a schematic representation of the pathway leading to the production of some phenylpropanoids determining color and scent profiles in *petunia* flowers. Single arrows indicate one step reactions. Volatile compounds are boxed, and solid and hatched arrows indicate established and proposed biochemical reactions, respectively. Metabolites produced to a higher level and genes whose expression was upregulated in Pap1-transgenic vs. control *petunia* flowers are underlined. EPSP synthase—5-enolpyruvylshikimate 3-phosphate synthase, PAAS—phenylacetaldehyde synthase, PAL—phenylalanine ammonia lyase, BSMT—S-adenosyl-L-Met:benzoic acid/salicylic acid carboxyl methyltransferase, C4H—cinnamic acid-4-hydroxylase, CHS— chalcone synthase, CHI—chalcone isomerase, F3H—flavanone 3-hydroxy lase, DFR—dihydroflavonol-4-reductase.

Figure 9H:
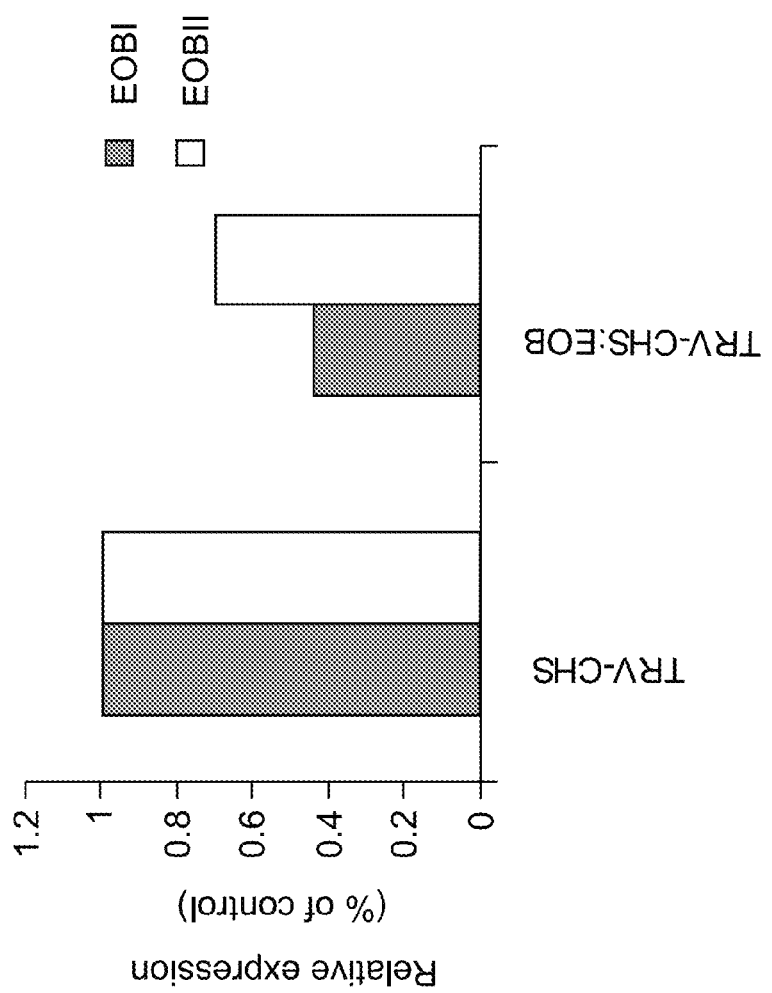

FIGS. 9A-H depict scanning for transcription factors regulating volatile production and their effect in *Petunia* using VIGS. Putative Myb-like transcription factors EOBI and EOBII were silenced via fusion of the 3' parts of their sequences to pTRV2-CHS, creating pTRV2-CHS:EOBI and pTRV2-CHS:EOBII fusions, respectively, and introducing them into P720 *petunia* plants (FIGS. 9B, 9C and 9D, respectively). Discoloration of *petunia* corollas (FIGS. 9B-D) shows successful VIGS silencing as compared to control *petunia* infected with an empty TRV2 (FIG. 9A). In FIG. 9E, petals were harvested from a *petunia* plant infected with TRV2 containing a conserved EOB domain (TRV2-EOB); FIGS. 9F-G depict the similar and significant reduction in benzenoid (but not terpenoid volatile compounds) by both EOBI and II. Headspace analysis was conducted for 16 h with flowers collected 2 days post-anthesis. Each graph represents the average of four to seven independent experiments with SEs indicated by vertical lines. A *petunia* plant inoculated with pTRV2-CHS constructs was used as control; FIG. 9H depicts a quantitative real-time PCR analysis used to determine EOBI and EOBII transcript levels in *petunia* flowers infected with pTRV2-CHS and pTRV2-CHS:EOB. Actin was used as a reference gene. Relative transcript levels for each gene were normalized to that of TRV2-CHS infected petals. The results represent means of three to four experiments.

Figure 10A:
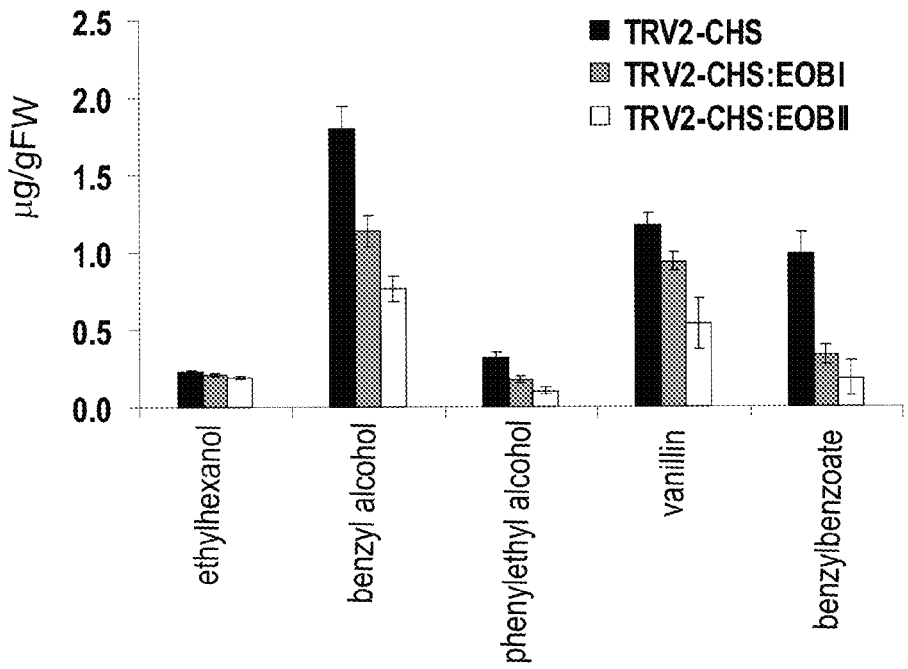
Figure 10B:
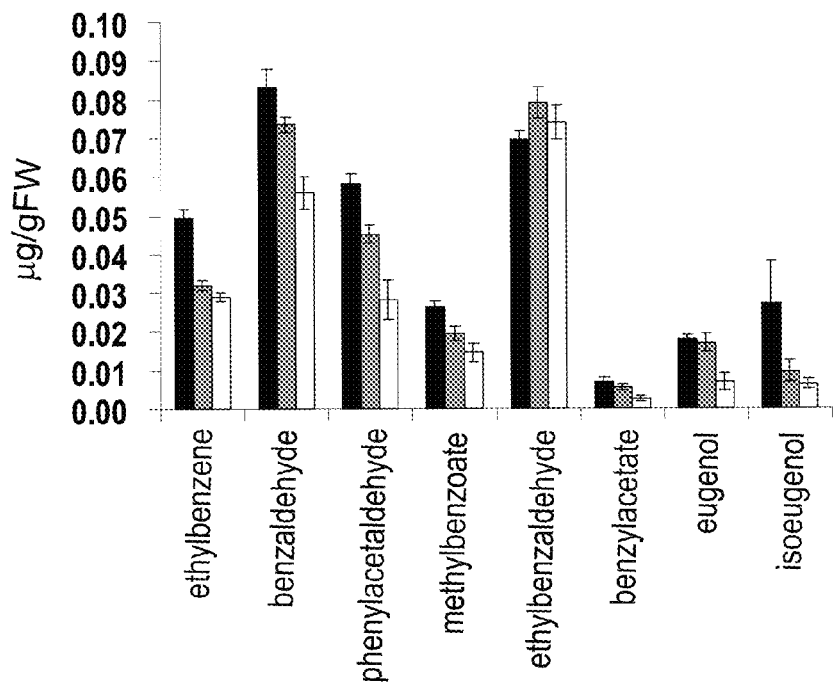

FIGS. 10A-B depict the internal volatile pool levels in corollas of *petunia* flowers infected with pTRV2-CHS, pTRV2-CHS:EOBI and pTRV2-CHS:EOBII as determined by GC-MS. Petals were collected and extraction was performed at 7:00 h. Each graph represents the average of four to seven independent experiments with SEs indicated by vertical lines.

Figure 11:
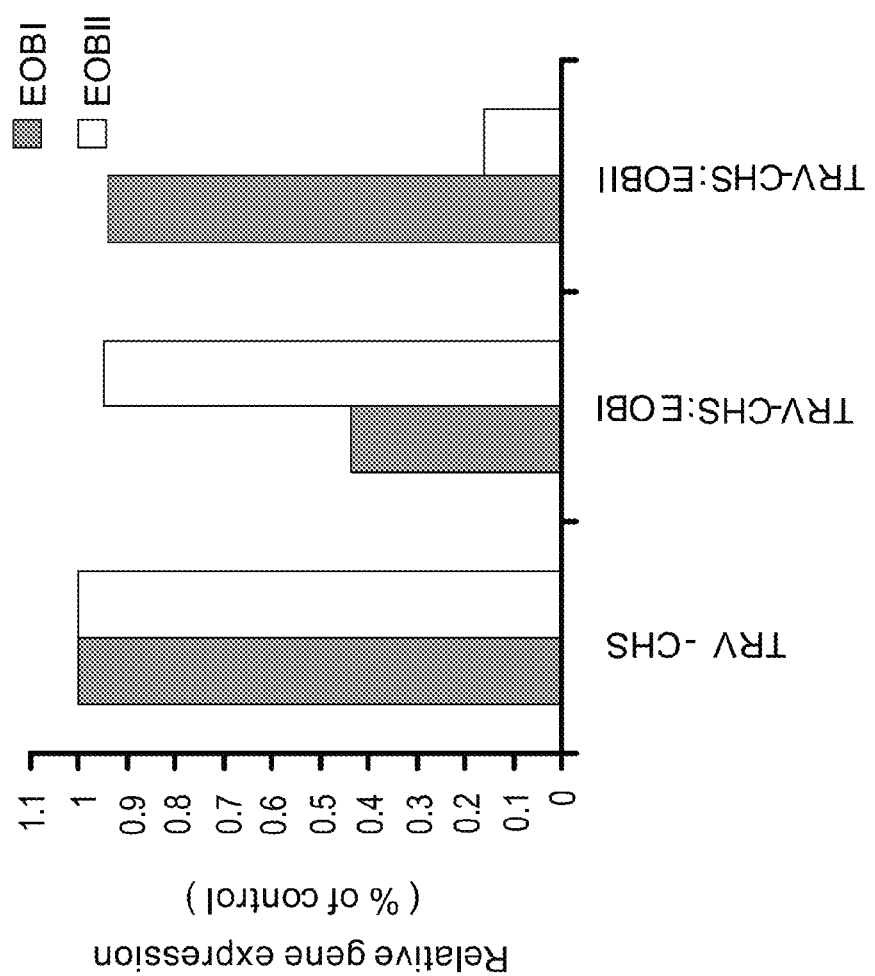

FIG. 11 depicts the silencing of EOBI and EOBII in pTRV2-CHS:EOBI and pTRV2-CHS:EOBII infected *petunia* plants. Quantitative real-time PCR analysis was used to determine EOBI and EOBII transcript levels in *petunia* flowers infected with pTRV2-CHS, pTRV2-CHS:EOBI and pTRV2-CHS:EOBII. Actin was used as a reference gene. Relative transcript levels for each gene were normalized to that of TRV2-CHS infected petals. The results represent means of three to four experiments.

Figure 12A:
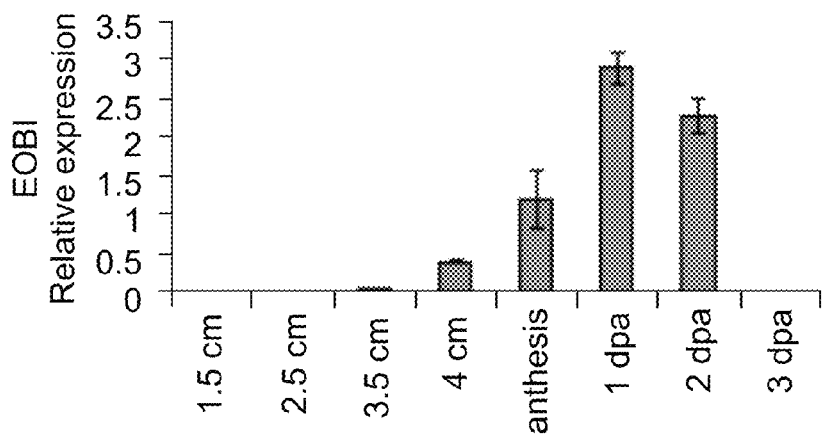
Figure 12B:
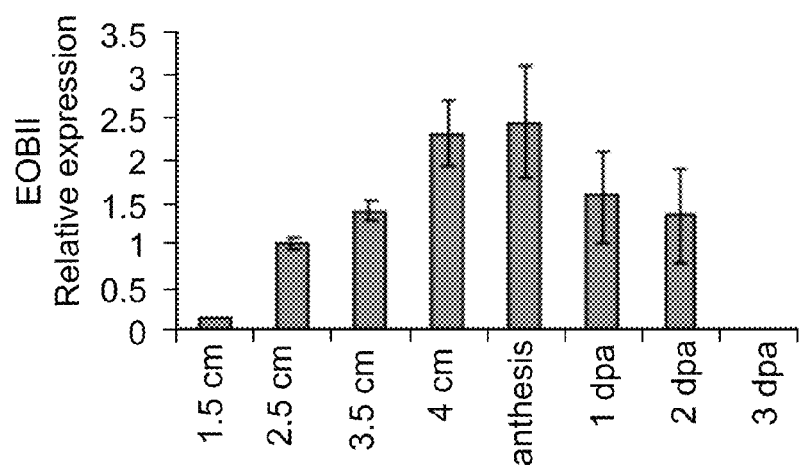
Figure 12C:
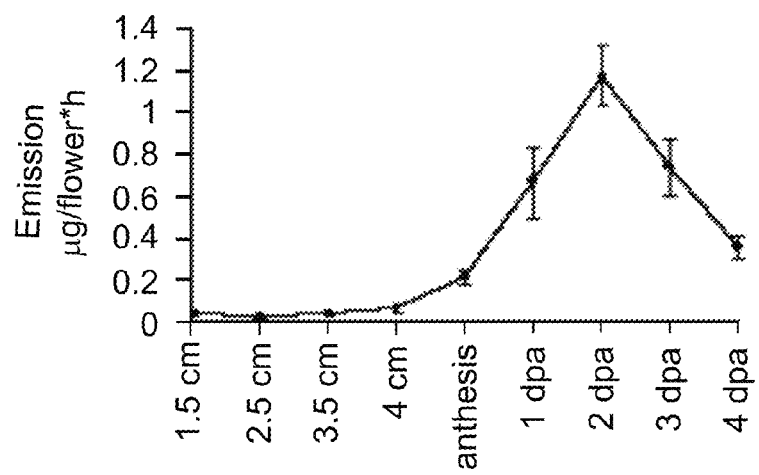
Figure 12D:
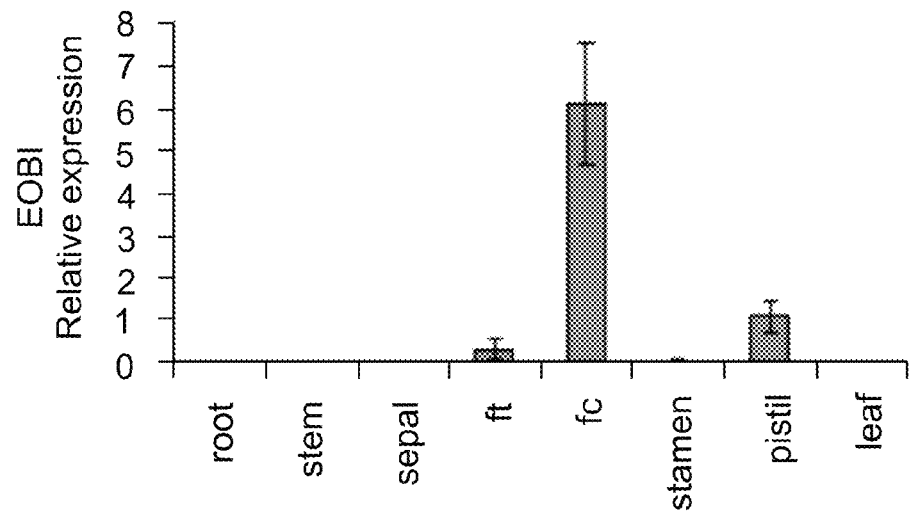
Figure 12E:
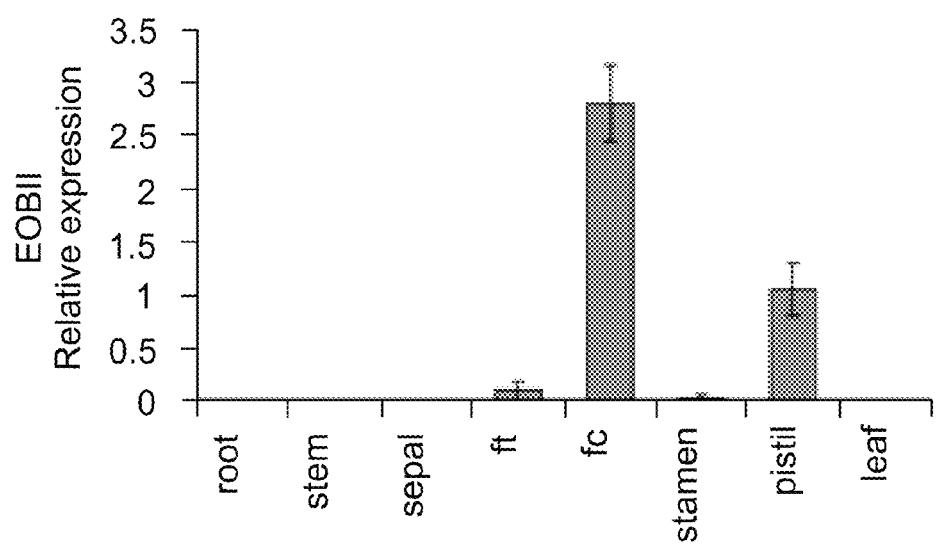
Figure 12F:
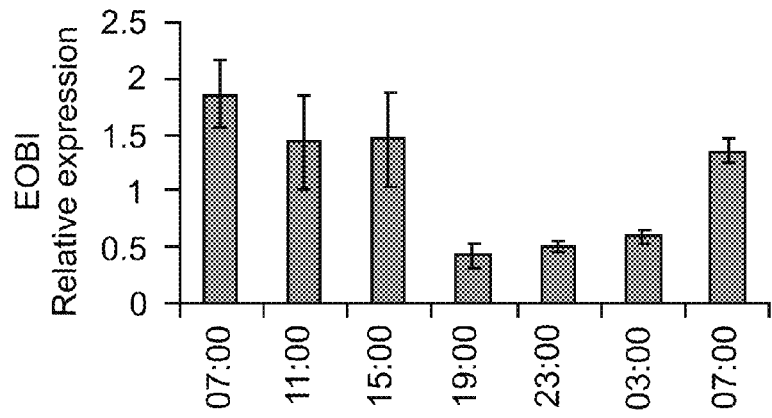
Figure 12G:
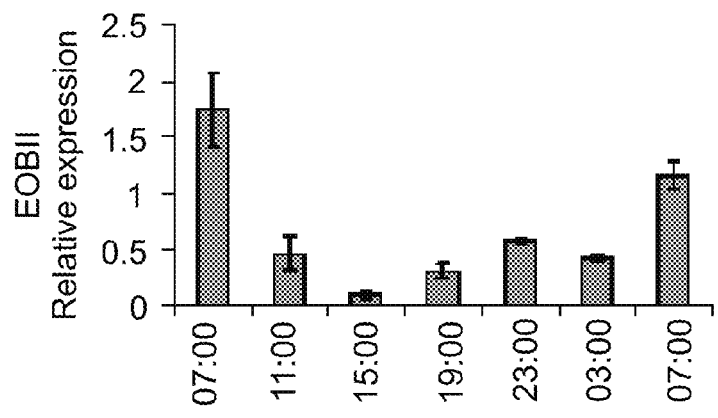
Figure 12H:
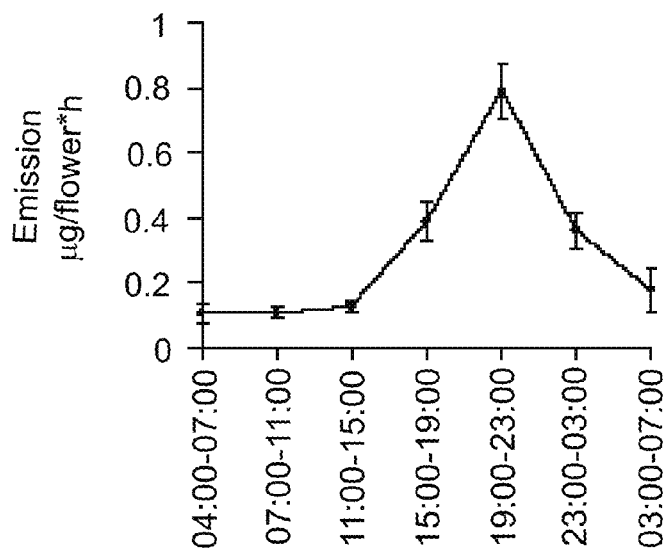

FIGS. 12A-H depict the spatial, temporal and developmental regulation of EOBI and EOBII transcript levels and of scent emission in petunia. FIGS. 12A-B, 12D-E and 12F-G depict transcript levels of EOBI (FIGS. 12A, 12D and 12F) and EOBII (FIGS. 12B, 12E and 12G) which were analyzed using quantitative real-time PCR. The RNA was extracted from flower corollas at different development stages (FIGS. 12A-B), from different organs of *petunia* (FIGS. 12D-E) and at different time points during a 24 h period (FIGS. 12F-G). Actin was used as the reference gene. The results represent means of three experiments and SEs are indicated by vertical lines. Of note, ft stands for flower tube and fc stands for flower corolla; FIGS. 12C and 12H depict levels of volatiles emitted from *petunia* flowers as determined using GC-MS. Dynamic headspace analysis was conducted for 24 h with flowers collected at different development stages (FIG. 12C), from young buds 1.5 cm in length to flowers 4 days postanthesis (dpa), or every 4 h (FIG. 12H) for 27 h. Each time point represents the average of three to five independent experiments with SEs indicated by vertical lines.

Figure 13A:
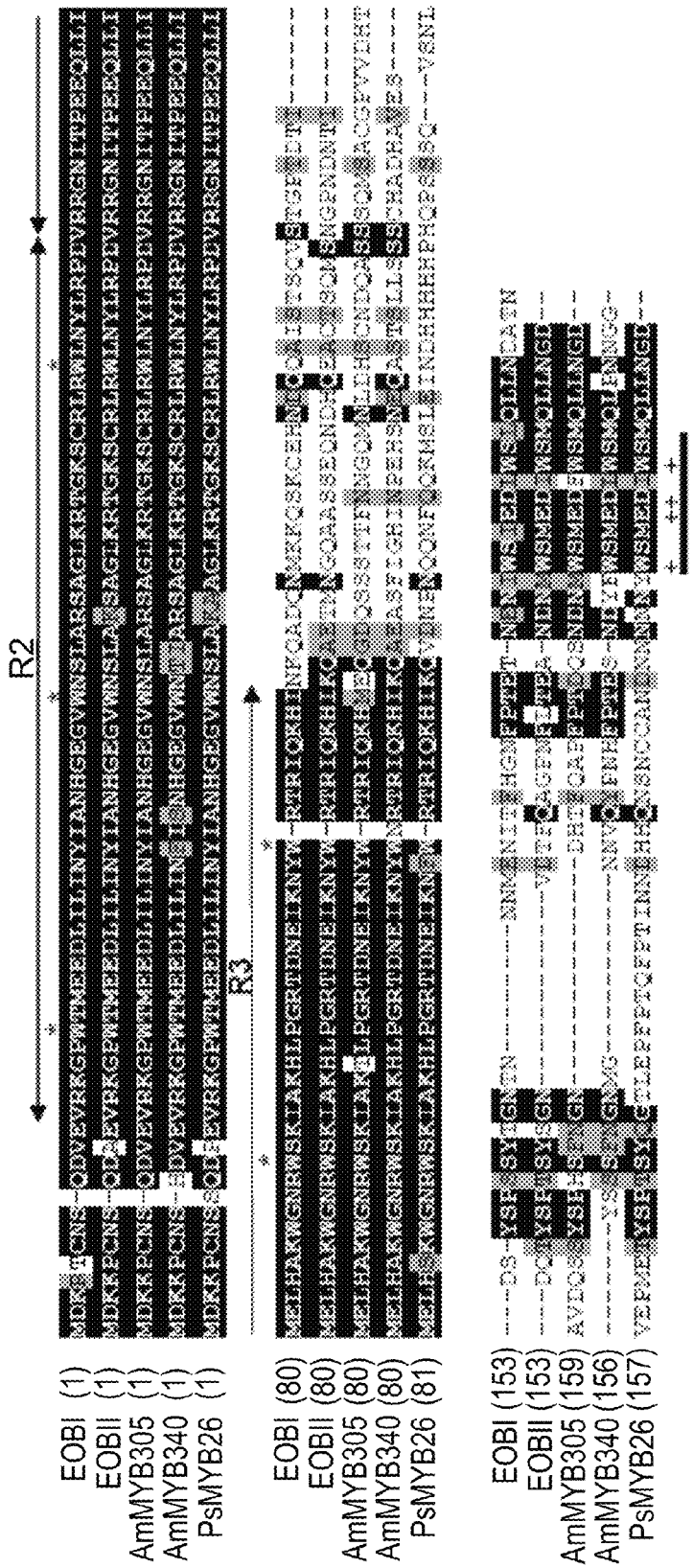
Figure 13B:
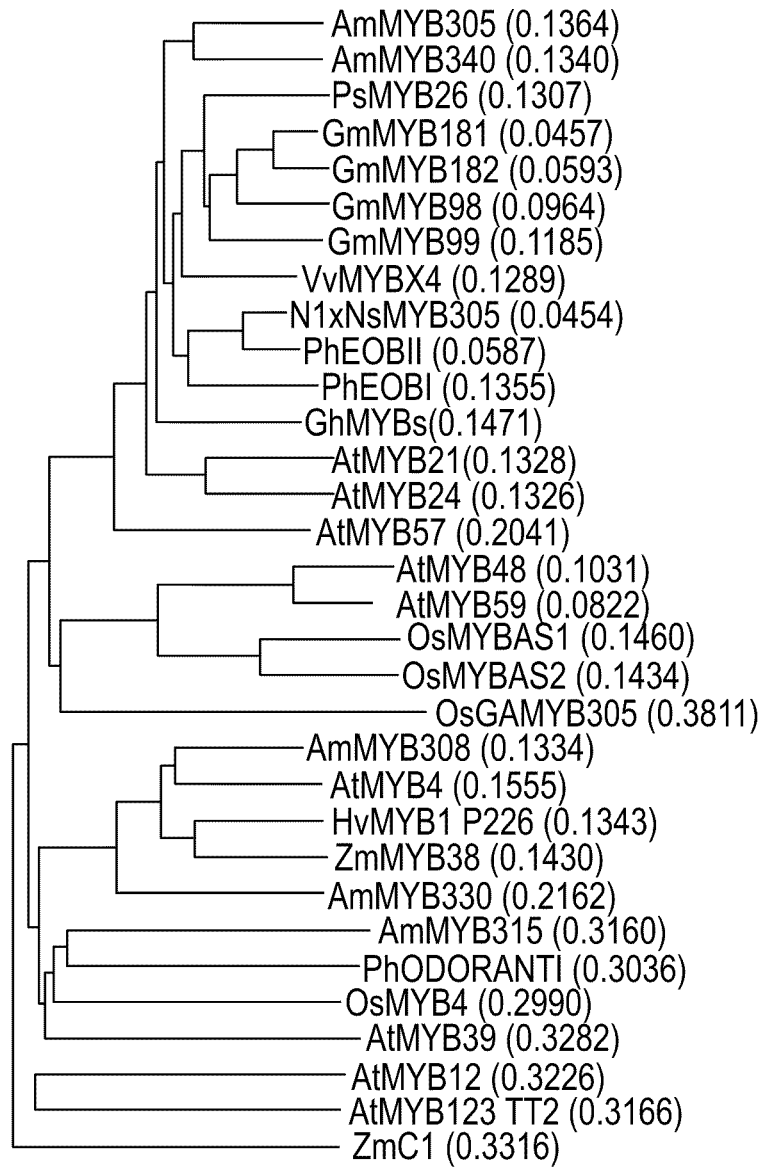

FIGS. 13A-B depict the sequence alignment of EOBI and EOBII and their proximity to related genes. FIG. 13A depicts sequence alignment of EOBI and EOBII. Identical amino acids are shaded in black, conserved changes are depicted in gray. The two MYB repeats (R2 and R3) are indicated with sets of arrows, and the critical tryptophan residues are indicated by star marks. The motif region is underlined, with the conserved amino acids marked by +. Numbers in parenthesis indicate amino acid positions; FIG. 13B depict a tree generated by neighbor joining method in AlignX of vector NTI Advance 9.0. Calculated relative distance values are shown in parenthesis following the protein name.

FIGS. 14A-H depict the Nuclear localization of EOBI and EOBII. GFP expression of EOBI:GFP, EOB2:GFP and GFP was monitored by a florescent microscope. Localization of the fusion proteins EOBI:GFP and EOBII:GFP in leaf epidermis is shown in the left and center columns, respectively. Fluorescence of non-fused GFP control in cells is shown in the right column. Nucleus stained with 4,6-diamidino-2-phenylindole (DAPI) is shown in blue and bright field is shown in the bottom panels.

Figure 15A:
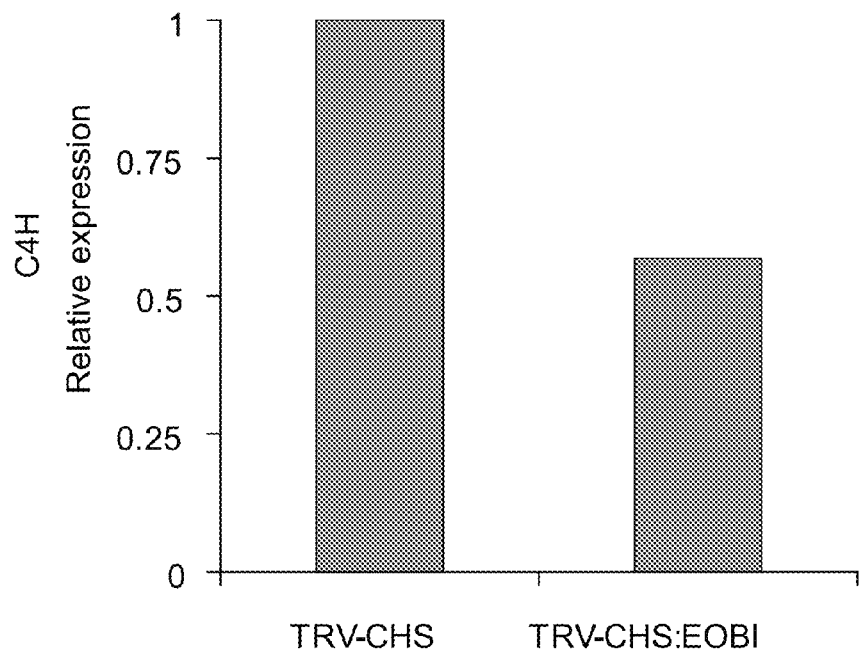
Figure 15B:
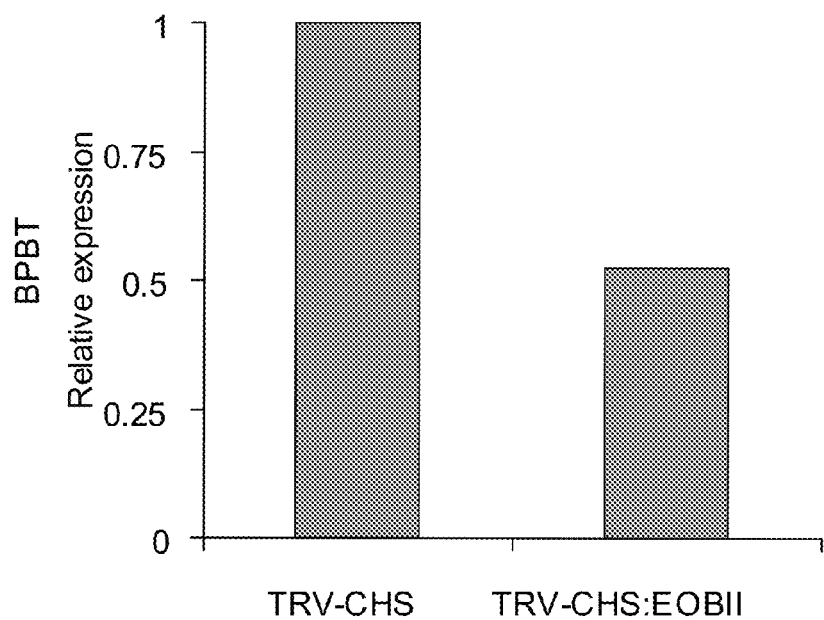
Figure 15C:
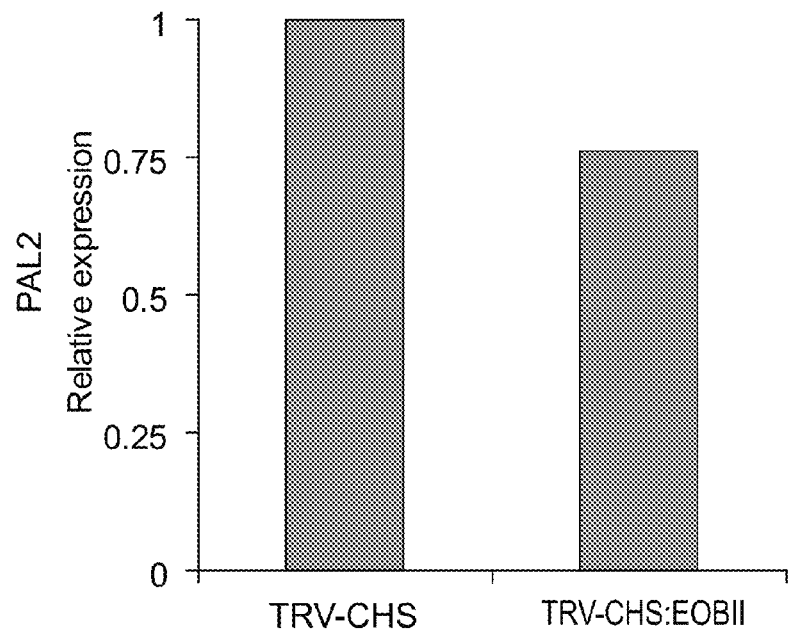
Figure 15D:
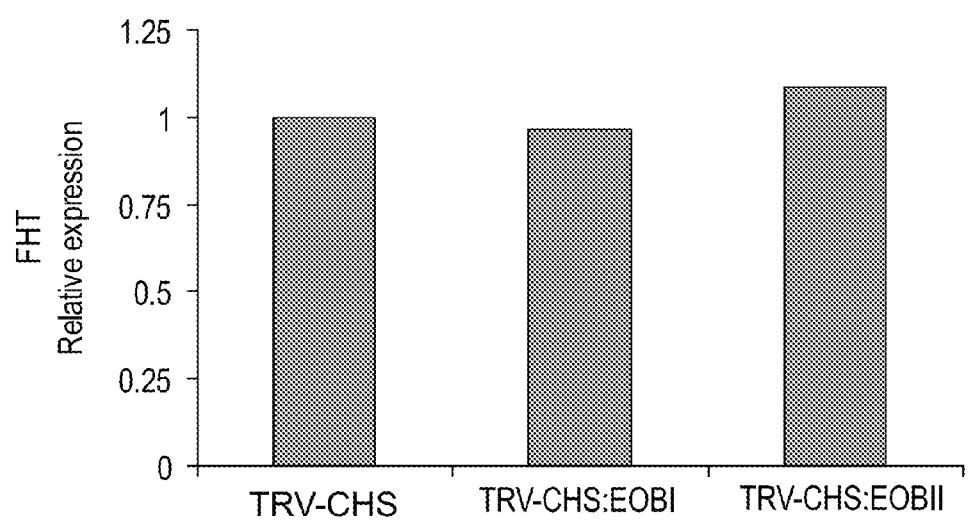

FIGS. 15A-D depict the effect of EOBI and EOBII silencing on the transcript levels of different phenylpropanoid structural genes. Quantitative real-time PCR analysis was used to determine C4H (FIG. 15A) transcript levels in *petunia* flowers silenced with pTRV2-CHS and pTRV2-CHS:EOBI; FIGS. 15B and 15C depict BPBT and PAL2 transcript levels, respectively, in *petunia* flowers silenced with pTRV2-CHS and pTRV2-CHS:EOBII; and FIG. 15D depict FHT transcript level in *petunia* flowers silenced with pTRV2-CHS:EOBI, pTRV2-CHS:EOBII and pTRV2-CHS. Actin was used as a reference gene. Relative transcript levels for each gene were normalized to that of TRV2-CHS infected petals. The results represent means of three to four experiments.

DESCRIPTION OF SPECIFIC EMBODIMENTS OF THE INVENTION

The present invention, in some embodiments thereof, relates to methods of modulating production of phenylpropanoid compounds in plants and, more particularly, but not exclusively, to plant extracts obtained therefrom.

The principles and operation of the present invention may be better understood with reference to the drawings and accompanying descriptions.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

While reducing the present invention to practice, the present inventors have identified the role of myb genes in the regulation of phenylpropanoid production in plants. Based on this finding the present inventors were able to modulate phenylpropanoid production and change the scent emission rhythmus of plants to constantly high scent emission during day and night. Furthermore, the present inventors have uncovered new genes of the myb gene family and further exhibited the function of these newly identified genes in the phenylpropanoid pathway in plants.

As is shown hereinbelow and in the Examples section which follows, the present inventors have shown that overexpression of the myb gene, Pap1 (GenBank accession no. AF325123, SEQ ID NOs: 1 and 2) leads to increased pigmentation (FIGS. 1A-B) and scent in *Petunia* flowers. Increased pigmentation and scent were accompanied by increased levels of transcripts encoding for enzymes involved in the production of both volatile (PAAS) and non-volatile (F3H and DFR) phenylpropanoid compounds. The Pap1 transgenic flowers exhibited about 3-5 fold increase in volatile emission (FIGS. 2A-B) and about 10 fold increase in internal pool levels of volatile compounds (FIGS. 2E-F). Furthermore, the present inventors have shown that Pap1 overexpression leads to increased phenylalanine (Phe) utilization in *Petunia* (FIG. 5C) via wide transcriptional activation of the phenylpropanoid pathway including L-Phe ammonia lyase (PAL, FIG. 5B), C4H, PAAS, F3H and DFR (FIG. 5D). Administration of Phe to Pap1 transgenic flowers (e.g. during the day) resulted in a significant increase in volatile emission (about 7-fold and 5-fold increase in benzaldehyde and methylbenzoate emission, respectively, FIGS. 7B-C).

Moreover, it is shown herein that the present inventors have cloned two new genes of the Myb transcription factor family. These genes (designated herein as EOBI and EOBII) were discovered in *Petunia*. Sequence analysis of these new polynucleotides showed that they encode for a 202 amino acid protein (EOBI, SEQ ID NO: 52) and a 197 amino acid protein (EOBII, SEQ ID NO: 54), both comprising the conserved Myb R2R3 binding domain and a W-MDDIW motif (SEQ ID NO: 57, FIG. 13A). Downregulation of these genes in *Petunia* by virus-induced gene silencing (VIGS) resulted in a significant reduction in internal pool levels (FIGS. 10A-B) and emission levels (FIG. 9F) of phenylpropanoid volatile compounds as well as in the levels of transcripts encoding for enzymes involved in the production of phenylpropanoid compounds (C4H, BPBT and PAL-2, FIGS. 15A-C). Moreover, these gene transcripts were shown herein to accumulate to the highest levels in flowers at anthesis (EOBII, FIG. 12B) or 1 day post anthesis (EOBI, FIG. 12A) and their levels peaked several hours prior to scent production (FIG. 12F-G). Taken together, all these findings substantiate Myb genes (e.g. Pap1, EOBI and EOBII) as specific regulators of the phenylpropanoid pathway, as for example, in volatile phenylpropanoid production.

Thus, according to one aspect of the present invention there is provided a method of enhancing production of a phenylpropanoid compound in a plant or plant cell, the method comprising expressing in the plant or plant cell a heterologous polynucleotide which produces a myb gene of the phenylpropanoid pathway, thereby enhancing the production of the phenylpropanoid compound in the plant or plant cell.

As used herein the term "myb gene of the phenylpropanoid pathway" refers to a gene which encodes for a protein that comprises at least one copy of the conserved MYB DNA-binding domain (PF00249). Typically the myb domain is a sequence of about 50 amino acids in length with a structure similar to the helix-turn-helix motif of prokaryotic transcriptional repressors and eukaryotic homeodomains.

In an exemplary embodiment, the myb domain is an R2R3 domain (for example as set forth in SEQ ID NOs: 60-62). In a further exemplary embodiment, the myb gene comprises a Myb domain and a W-MDDIW motif (SEQ ID NO: 57).

As used herein, the phrase "heterologous polynucleotide" refers to a nucleic acid sequence which is not naturally expressed within the plant or which overexpression in the plant is desired. The heterologous polynucleotide may be introduced into the plant in a stable or transient manner.

As used herein the phrase "polynucleotide" refers to a single or double stranded nucleic acid sequences which is isolated and provided in the form of an RNA sequence, a complementary polynucleotide sequence (cDNA), a genomic polynucleotide sequence and/or a composite polynucleotide sequences (e.g., a combination of the above).

As used herein the phrase "complementary polynucleotide sequence" refers to a sequence, which results from reverse transcription of messenger RNA using a reverse transcriptase or any other RNA dependent DNA polymerase. Such a sequence can be subsequently amplified in vivo or in vitro using a DNA dependent DNA polymerase.

As used herein the phrase "genomic polynucleotide sequence" refers to a sequence derived (isolated) from a chromosome and thus it represents a contiguous portion of a chromosome.

As used herein the phrase "composite polynucleotide sequence" refers to a sequence, which is at least partially complementary and at least partially genomic. A composite sequence can include some exonal sequences required to encode the polypeptide of the present invention, as well as some intronic sequences interposing therebetween. The intronic sequences can be of any source, including of other genes, and typically will include conserved splicing signal sequences. Such intronic sequences may further include cis acting expression regulatory elements.

It will be appreciated that the heterologous polynucleotide can encode a myb gene of the phenylpropanoid pathway. Alternatively or additionally the heterologous polynucleotide may comprise a regulatory sequence (e.g., cis-acting) capable of upregulating endogenous production of a myb-gene of the phenylpropanoid pathway in the plant. Directed insertion of regulatory sequences, or modification of regulatory sequences can be effected using methods which are well known in the art [see e.g. Okuzaki and Toriyarna Chimeric RNA/DNA oligonucleotide-directed gene targeting in rice. Plant Cell Rep (2004) 22:509-512; Dong et al., Oligonucleotide-directed gene repair in wheat using a transient plasmid gene repair assay system. Plant Cell Rep (2006) 25: 457-465; Ow, Site-Specific Recombination for Plant Genetic Engineering: Strategy for Agro-Mediated Gene Stacking Eds. R. E. Litz and R. Scorza. Proc. IS on Biotechnol. Temp. Fruit Crops & Trop. Species. Acta Hort. 738, ISHS (2007), each of which is incorporated by reference in its entirety].

According to exemplary embodiments of this aspect of the present invention, the polynucleotide comprises a nucleic acid sequence at least at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more say 100% homologous to Pap1 (GenBank accession no. AF325123, SEQ ID NO: 1), EOBI (GenBank accession no: EU360892, SEQ ID NO: 51) or EOBII (GenBank accession no: EU360893, SEQ ID NO: 53).

According to other exemplary embodiments of this aspect of the present invention the polynucleotide comprises a nucleic acid sequence encoding a polypeptide having an amino acid sequence at least at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more say 100% homologous to Pap1 (GenBank accession no. AF325123, SEQ ID NO: 2), EOBI (GenBank accession no: EU360892, SEQ ID NO: 52) or EOBII (GenBank accession no: EU360893, SEQ ID NO: 54).

Homology (e.g., percent homology) can be determined using any homology comparison software, including for example, the Blast or TBLAST software of the National Center of Biotechnology Information (NCBI) such as by using default parameters, when starting from a polypeptide sequence; or the tBLASTX algorithm (available via the NCBI) such as by using default parameters, which compares the six-frame conceptual translation products of a nucleotide query sequence (both strands) against a protein sequence database.

Homologous sequences include both orthologous and paralogous sequences. The term "paralogous" relates to gene-duplications within the genome of a species leading to paralogous genes. The term "orthologous" relates to homologous genes in different organisms due to ancestral relationship.

Thus, additional examples of homologous/orthologous sequences are listed in Tables 1 and 2, hereinbelow. Determining the suitability of any of the polynucleotide sequences as regulators of the phenylpropanoid pathway can be effected by methods which are well known in the art and which are further described hereinbelow (e.g. scent emission, pigmentation).

TABLE 1

EOBI homologous genes

| EOBI homologies using tblastn | EOBI homologies using blastp | EOBI homologies using blastn | EOBI homologies using blastn in EST database |
|---|---|---|---|
| gb\|EU111678.1\| | gb\|ABU97107.1\| | EU111679.1 | DC240927.1 |
| gb\|EU111679.1\| | gb\|ABU97106.1\| | EU111678.1 | EB693289.1 |
| emb\|AJ554698.1\| | emb\|CAD87008.1\| | AB289443.1 | EB697946.1 |
| gb\|EU181426.1\| | sp\|P81391\|MYB05__ANTMA | Y11105.1 | EB695721.1 |
| dbj\|AB289444.1\| | sp\|P81396\|MYB40__ANTMA | AC215353.2 | EB695695.1 |
| dbj\|AB289443.1\| | emb\|CAN77103.1\| | AC215853.1 | EB695442.1 |
| gb\|DQ822906.1\| | dbj\|BAF96932.1\| | AC215465.1 | EB695274.1 |
| emb\|Y11105.1\|PSMYB26 | gb\|ABW34394.1\| | AB434573.1 | EB695254.1 |
| gb\|DQ822908.1\| | dbj\|BAF96931.1\| | DQ822901.1 | EB695104.1 |
| gb\|DQ822907.1\| | gb\|ABH02847.1\| | DQ822898.1 | EB694806.1 |
| gb\|DQ822931.1\| | emb\|CAA71992.1\| | DQ822966.1 | EB694757.1 |
| gb\|AY086615.1\| | gb\|ABH02849.1\| | | EB694662.1 |
| ref\|NM_123399.4\| | gb\|ABH02848.1\| | | EB693710.1 |
| gb\|AY519632.1\| | gb\|ABH02872.1\| | | EB693586.1 |
| gb\|AF175987.1\|AF175987 | gb\|AAM63674.1\| | | EB693202.1 |
| emb\|BX829759.1\|CNS0A1B5 | ref\|NP_198851.1\| | | EB692691.1 |
| gb\|AY519589.1\| | ref\|NP_189418.2\| | | EB691847.1 |
| ref\|NM_113696.2\| | dbj\|BAB40790.1\| | | EB691296.1 |
| dbj\|AK118439.1\| | dbj\|BAA21618.1\| | | EB693508.1 |
| dbj\|AB058642.1\| | ref\|NP_186802.1\| | | EB694671.1 |
| dbj\|AB005888.1\| | gb\|AAM67076.1\| | | EB694184.1 |
| gb\|AY519582.1\| | gb\|ACF83741.1\| | | EB693861.1 |
| gb\|BT005574.1\| | ref\|NP_001049937.1\| | | EB693023.1 |
| ref\|NM_111019.2\| | gb\|EAY89765.1\| | | EB692586.1 |
| dbj\|AK118091.1\| | gb\|EAZ26713.1\| | | EB691662.1 |
| gb\|AY088761.1\| | gb\|AAL84762.1\|AF474129_1 | | EB689567.1 |
| emb\|BX822161.1\|CNS0A4YP | gb\|ACF87244.1\| | | EB695736.1 |
| emb\|CT834128.1\| | ref\|NP_001060700.1\| | | EB695408.1 |
| emb\|CT830663.1\| | dbj\|BAC21351.1\| | | EB693865.1 |
| gb\|BT038736.1\| | gb\|EAY83532.1\| | | EB693816.1 |
| ref\|NM_001056472.1\| | gb\|ABA98967.1\| | | EB692876.1 |
| dbj\|AK120551.1\| | gb\|EAY96442.1\| | | EB692383.1 |
| gb\|BT042239.1\| | ref\|NP_001054560.1\| | | EB692381.1 |
| ref\|NM_001067235.1\| | ref\|NP_001068466.1\| | | EB692280.1 |
| dbj\|AK103455.1\| | gb\|ABU93236.1\| | | EB691938.1 |
| ref\|NM_001061095.1\| | gb\|AAK08983.1\| | | EB694379.1 |
| emb\|CU406184.1\| | emb\|CAN76459.1\| | | EB694062.1 |
| gb\|EF587267.1\| | gb\|EAZ19253.1\| | | EB693457.1 |
| gb\|AY026332.1\| | emb\|CAO42159.1\| | | EB694513.1 |
| ref\|NM_001074998.1\| | emb\|CAO68074.1\| | | EB694202.1 |
| ref\|NM_001062891.1\| | gb\|EAY72379.1\| | | EB694119.1 |
| gb\|BT009018.1\| | gb\|EAY99070.1\| | | EB689270.1 |
| gb\|AF485900.1\| | gb\|EAZ10389.1\| | | EB424656.1 |
| gb\|BT040615.1\| | ref\|NP_001056356.1\| | | CV299555.1 |
| dbj\|AK069082.1\| | gb\|ACF85620.1\| | | CV299475.1 |
| gb\|DQ074462.1\| | gb\|AAL84765.1\|AF474132_1 | | CV298677.1 |
| ref\|NM_001048443.1\| | ref\|NP_001041908.1\| | | EB695156.1 |
| dbj\|AK241615.1\| | dbj\|BAB18296.1\| | | EB693169.1 |
| dbj\|AP008207.1\| | gb\|AAO49418.1\|AF485900_1 | | EB691789.1 |
| dbj\|AP003140.2\| | gb\|AAZ20430.1\| | | EB693862.1 |
| dbj\|AP002883.2\| | ref\|NP_001042810.1\| | | EB693657.1 |
| ref\|NM_001049345.1\| | gb\|AAG51527.1\|AC051631_7 | | EB693472.1 |
| gb\|AY519562.1\| | ref\|NP_564519.1\| | | EB427455.1 |
| dbj\|AK229083.1\| | ref\|NP_176999.1\| | | EB695243.1 |
| ref\|NM_103696.2\| | gb\|ABC54973.1\| | | EB695131.1 |
| gb\|AY008377.2\| | gb\|ABH02842.1\| | | EB693120.1 |

TABLE 1-continued

EOBI homologous genes

| EOBI homologies using tblastn | EOBI homologies using blastp | EOBI homologies using blastn | EOBI homologies using blastn in EST database |
|---|---|---|---|
| ref\|NM_105503.2\| | gb\|ABC54967.1\| | | EB692584.1 |
| gb\|AY519568.1\| | ref\|NP_564230.1\| | | EB691864.1 |
| dbj\|AP008213.1\| | gb\|ACG34790.1\| | | EB691758.1 |
| dbj\|AP003813.4\| | gb\|ACF81318.1\| | | AW928296.1 |
| dbj\|AP003816.2\| | emb\|CAO44955.1\| | | CV506606.1 |
| gb\|DQ446290.1\| | emb\|CAN63179.1\| | | AI897784.2 |
| gb\|AY519558.1\| | gb\|ABC54990.1\| | | AI897681.1 |
| gb\|DQ277667.1\| | ref\|NP_199773.1\| | | EB693605.1 |
| gb\|EU962672.1\| | gb\|ABC54957.1\| | | AI486576.1 |
| gb\|DQ277661.1\| | gb\|ABC54969.1\| | | EB691761.1 |
| gb\|BT036313.1\| | ref\|NP_182241.1\| | | EB689377.1 |
| ref\|NM_102344.2\| | gb\|AAM43912.1\|AF510112_1 | | EB688758.1 |
| gb\|AF334815.2\|AF334815 | gb\|AAB58313.1\| | | BG642441.1 |
| gb\|DQ822901.1\| | gb\|ABH02839.1\| | | AI487923.2 |
| dbj\|AK107424.1\| | gb\|AAB58314.1\| | | BQ584246.1 |
| gb\|DQ277685.1\| | gb\|ABH02913.1\| | | AW737355.1 |
| gb\|BT026076.1\| | gb\|ABK28415.1\| | | CX541696.1 |
| ref\|NM_124340.2\| | gb\|ABC54984.1\| | | CX540372.1 |
| gb\|AY519635.1\| | gb\|ABC54983.1\| | | CX538934.1 |
| gb\|DQ277649.1\| | dbj\|BAB62112.1\| | | BQ146360.1 |
| gb\|DQ822898.1\| | dbj\|BAB62121.1\| | | BI273011.1 |
| gb\|DQ277672.1\| | dbj\|BAB62119.1\| | | DR462104.1 |
| gb\|DQ277663.1\| | dbj\|BAB62114.1\| | | FG485639.1 |
| gb\|U33917.1\|CPU33917 | gb\|ABC54986.1\| | | FG453884.1 |
| gb\|AF510112.1\| | dbj\|BAB62110.1\| | | FG453150.1 |
| gb\|BT011656.1\| | ref\|NP_001043670.1\| | | FG508873.1 |
| gb\|AY519579.1\| | gb\|ABC54966.1\| | | EY197638.1 |
| dbj\|AK229140.1\| | gb\|ACF79639.1\| | | EX166322.1 |
| ref\|NM_130287.2\| | gb\|EAZ12843.1\| | | AI489912.1 |
| gb\|BT010949.1\| | dbj\|BAB62115.1\| | | FG453111.1 |
| gb\|DQ652860.1\| | dbj\|BAB62118.1\| | | FG453703.1 |
| gb\|DQ277678.1\| | ref\|NP_187301.1\| | | EX292075.1 |
| gb\|DQ277677.1\| | gb\|AAS10054.1\| | | EX289184.1 |
| gb\|DQ277680.1\| | gb\|ABB84756.1\| | | EB692604.1 |
| gb\|DQ822972.1\| | emb\|CAO40161.1\| | | FG428833.1 |
| emb\|BX821709.1\|CNS0A89G | ref\|NP_001031091.1\| | | FG453401.1 |
| ref\|NM_001050205.1\| | gb\|ACG45505.1\| | | EB694642.1 |
| gb\|DQ277659.1\| | emb\|CAM58451.1\| | | BJ553935.1 |
| gb\|BT034634.1\| | emb\|CAN66274.1\| | | EL359998.1 |
| gb\|EU952438.1\| | gb\|AAS58509.1\| | | EH709562.1 |
| ref\|NM_111525.2\| | ref\|NP_189074.1\| | | EH709022.1 |
| gb\|AF262733.2\|AF262733 | gb\|ABH02836.1\| | | EH707269.1 |
| gb\|AY519584.1\| | gb\|ACI16512.1\| | | EH705899.1 |
| gb\|DQ277682.1\| | gb\|AAS10076.1\| | | EH705342.1 |

TABLE 2

EOBII homologous genes

| EOBII homologies using tblastn | EOBII homologies using tblastn | EOBII homologies using blastn | EOBII homologies using blastn in EST database |
|---|---|---|---|
| gb\|EU111678.1\| | gb\|ABU97107.1\| | EU111679.1 | |
| gb\|EU111679.1\| | gb\|ABU97106.1\| | Y11105.1 | CV298677.1 |
| gb\|EU181426.1\| | emb\|CAN77103.1\| | DQ277680.1 | CV295420.1 |
| emb\|AJ554698.1\| | gb\|ABW34394.1\| | NM_113696.2 | CV293861.1 |
| emb\|Y11105.1\|PSMYB26 | sp\|P81391\|MYB05_ANTMA | AY519589.1 | CV293375.1 |
| gb\|DQ822906.1\| | emb\|CAD87008.1\| | AK118439.1 | CV293412.1 |
| dbj\|AB289444.1\| | emb\|CAA71992.1\| | DQ277677.1 | CV295159.1 |
| gb\|DQ822931.1\| | gb\|ABH02847.1\| | AB005888.1 | EB424656.1 |
| gb\|DQ822908.1\| | dbj\|BAF96932.1\| | AY088761.1 | EB427455.1 |
| dbj\|AB289443.1\| | sp\|P81396\|MYB40_ANTMA | DQ277678.1 | EB694379.1 |
| gb\|DQ822907.1\| | gb\|ABH02872.1\| | NM_111019.2 | EB693862.1 |
| ref\|NM_113696.2\| | gb\|ABH02849.1\| | AY519582.1 | EB693710.1 |
| dbj\|AK118439.1\| | dbj\|BAF96931.1\| | BX822161.1 | EB694806.1 |
| gb\|AY519589.1\| | gb\|ABH02848.1\| | EU048872.1 | EB695721.1 |
| gb\|AY086615.1\| | ref\|NP_189418.2\| | DQ277679.1 | EB695408.1 |

TABLE 2-continued

EOBII homologous genes

| EOBII homologies using tblastn | EOBII homologies using tblastn | EOBII homologies using blastn | EOBII homologies using blastn in EST database |
|---|---|---|---|
| dbj\|AB005888.1\| | gb\|AAM63674.1\| | AC215353.2 | EB695104.1 |
| ref\|NM_123399.4\| | dbj\|BAA21618.1\| | AC215853.1 | EB691296.1 |
| emb\|BX829759.1\|CNS0A1B5 | ref\|NP_198851.1\| | AC215465.1 | EB695695.1 |
| gb\|AY519632.1\| | dbj\|BAB40790.1\| | AB434573.1 | EB695442.1 |
| gb\|AF175987.1\|AF175987 | ref\|NP_186802.1\| | AF062870.1 | EB695274.1 |
| dbj\|AB058642.1\| | gb\|AAM67076.1\| | AC009325.8 | EB694757.1 |
| gb\|AY519582.1\| | gb\|ACF83741.1\| | NM_001084780.1 | EB694662.1 |
| gb\|BT005574.1\| | ref\|NP_001049937.1\| | NM_114482.1 | EB693586.1 |
| emb\|BX822161.1\|CNS0A4YP | gb\|EAY89765.1\| | NM_001035739.1 | EB691847.1 |
| ref\|NM_111019.2\| | gb\|EAZ26713.1\| | AY519594.1 | EB693457.1 |
| dbj\|AK118091.1\| | gb\|AAL84762.1\|AF474129_1 | DQ075257.1 | EB693169.1 |
| gb\|AY088761.1\| | ref\|NP_001060700.1\| | DQ075256.1 | EB697946.1 |
| emb\|CT834128.1\| | dbj\|BAC21351.1\| | DQ075255.1 | EB689567.1 |
| gb\|BT038736.1\| | gb\|ACF87244.1\| | AF272733.1 | EB695736.1 |
| emb\|CT830663.1\| | gb\|AAO49418.1\|AF485900_1 | AK176475.1 | EB695254.1 |
| ref\|NM_001056472.1\| | ref\|NP_001068466.1\| | Z95772.1 | EB694671.1 |
| dbj\|AK120551.1\| | gb\|EAY83532.1\| | | EB694119.1 |
| ref\|NM_001067235.1\| | gb\|ABA98967.1\| | | EB694062.1 |
| dbj\|AK103455.1\| | gb\|AAK08983.1\| | | EB693865.1 |
| gb\|AF485900.1\| | gb\|EAZ19253.1\| | | EB693289.1 |
| gb\|BT042239.1\| | gb\|EAY96442.1\| | | EB693202.1 |
| ref\|NM_001074998.1\| | ref\|NP_001054560.1\| | | EB692586.1 |
| gb\|AY026332.1\| | emb\|CAO68074.1\| | | EB692383.1 |
| ref\|NM_001061095.1\| | emb\|CAN76459.1\| | | EB691938.1 |
| emb\|CU406184.1\| | gb\|ABU93236.1\| | | EB691789.1 |
| gb\|EF587267.1\| | emb\|CAO42159.1\| | | EB689270.1 |
| ref\|NM_001062891.1\| | gb\|EAY99070.1\| | | EB695156.1 |
| gb\|BT009018.1\| | ref\|NP_001056356.1\| | | EB692280.1 |
| dbj\|AK069082.1\| | gb\|EAY72379.1\| | | EB693861.1 |
| gb\|DQ074462.1\| | gb\|EAZ10389.1\| | | EB692691.1 |
| gb\|DQ446290.1\| | gb\|AAZ20430.1\| | | EB694184.1 |
| gb\|AY519558.1\| | ref\|NP_564230.1\| | | EB692876.1 |
| ref\|NM_102344.2\| | ref\|NP_001041908.1\| | | EB694513.1 |
| gb\|AF334815.2\|AF334815 | dbj\|BAB18296.1\| | | EB693508.1 |
| ref\|NM_001048443.1\| | gb\|ACF85620.1\| | | EB692381.1 |
| gb\|BT040615.1\| | ref\|NP_176999.1\| | | EB695243.1 |
| ref\|NM_105503.2\| | gb\|AAL84765.1\|AF474132_1 | | EB695131.1 |
| gb\|AY519568.1\| | ref\|NP_001042810.1\| | | EB692584.1 |
| dbj\|AK107424.1\| | gb\|ABH02842.1\| | | EB693657.1 |
| dbj\|AK241615.1\| | gb\|ABK28415.1\| | | EB691864.1 |
| dbj\|AP008207.1\| | gb\|ABC54973.1\| | | EB691662.1 |
| dbj\|AP003140.2\| | gb\|ABC54967.1\| | | EB691758.1 |
| dbj\|AP002883.2\| | ref\|NP_182241.1\| | | EB693472.1 |
| ref\|NM_001049345.1\| | gb\|AAG51527.1\|AC051631_7 | | EB693120.1 |
| gb\|DQ652860.1\| | gb\|ABC54990.1\| | | EB694202.1 |
| gb\|DQ822901.1\| | gb\|ABH02839.1\| | | EB693023.1 |
| gb\|DQ277667.1\| | ref\|NP_564519.1\| | | EB693816.1 |
| gb\|DQ277661.1\| | gb\|ABC54957.1\| | | EB693605.1 |
| gb\|DQ822898.1\| | dbj\|BAB62112.1\| | | AI486576.1 |
| dbj\|AP008213.1\| | dbj\|BAB62119.1\| | | EB691761.1 |
| dbj\|AP003813.4\| | dbj\|BAB62114.1\| | | AW928296.1 |
| dbj\|AP003816.2\| | dbj\|BAB62121.1\| | | EB688758.1 |
| gb\|DQ277685.1\| | gb\|ABC54969.1\| | | CV502728.1 |
| emb\|BX821709.1\|CNS0A89G | dbj\|BAB62110.1\| | | AI897784.2 |
| gb\|BT011656.1\| | gb\|ABC54984.1\| | | AI897681.1 |
| gb\|AY519579.1\| | gb\|ABC54983.1\| | | DC240927.1 |
| gb\|AY519562.1\| | gb\|ABC54986.1\| | | EB689377.1 |
| dbj\|AK229140.1\| | dbj\|BAB62115.1\| | | EB692604.1 |
| ref\|NM_130287.2\| | dbj\|BAB62118.1\| | | BG642441.1 |
| gb\|BT010949.1\| | gb\|AAM43912.1\|AF510112_1 | | AI487923.2 |
| gb\|DQ277649.1\| | gb\|ACF81318.1\| | | CV506606.1 |
| dbj\|AK229083.1\| | gb\|ACG34790.1\| | | DR462104.1 |
| ref\|NM_103696.2\| | gb\|ABC54966.1\| | | EY197678.1 |
| gb\|AY008377.2\| | gb\|AAB58313.1\| | | EX166322.1 |
| gb\|DQ277672.1\| | emb\|CAO44955.1\| | | CV466307.1 |
| gb\|DQ277663.1\| | emb\|CAN63179.1\| | | CV130213.1 |
| gb\|DQ277678.1\| | gb\|AAB58314.1\| | | ES817664.1 |
| gb\|EU962672.1\| | gb\|ACF79639.1\| | | CO113188.1 |
| gb\|DQ277677.1\| | ref\|NP_199773.1\| | | CN495741.1 |
| gb\|BT036313.1\| | gb\|ABB84756.1\| | | AI489912.1 |
| gb\|DQ277680.1\| | ref\|NP_001031091.1\| | | EB694642.1 |
| gb\|DQ277659.1\| | gb\|EAZ12843.1\| | | CX540372.1 |

TABLE 2-continued

EOBII homologous genes

| EOBII homologies using tblastn | EOBII homologies using tblastn | EOBII homologies using blastn | EOBII homologies using blastn in EST database |
|---|---|---|---|
| gb\|AF510112.1\| | ref\|NP_001043670.1\| | | CX538934.1 |
| gb\|U33917.1\|CPU33917 | gb\|ABH02913.1\| | | BI273011.1 |
| gb\|BT034634.1\| | gb\|ACG45505.1\| | | CX541696.1 |
| gb\|EU952438.1\| | ref\|NP_187301.1\| | | AJ791605.1 |
| gb\|BT026076.1\| | gb\|AAS10054.1\| | | AJ790280.1 |
| ref\|NM_124340.2\| | emb\|CAO40161.1\| | | BQ146360.1 |
| gb\|AY519635.1\| | emb\|CAM58451.1\| | | BQ146831.1 |
| ref\|NM_001036014.1\| | ref\|NP_189074.1\| | | BG457971.1 |
| gb\|DQ267899.1\| | gb\|AAS58509.1\| | | BE324639.2 |
| gb\|AY112586.1\| | emb\|CAN66274.1\| | | FG453150.1 |
| ref\|NM_001050205.1\| | ref\|NP_193084.1\| | | BQ584246.1 |
| gb\|DQ277682.1\| | gb\|AAS10076.1\| | | CX540018.1 |
| gb\|DQ822972.1\| | gb\|ABH02836.1\| | | BI272897.1 |
| | | | FG453111.1 |

Blast analysis was carried out using GenBank Blast (www.//blast(dot)ncbi(dot)nlm(dot)nih(dot)gov/Blast.cgi?CMD=Web&PAGE_TYPE=BlastHome). For EOBI and II homologies done using tblastn the search was done in translated nucleotide database using a protein query, using nucleotide collection data base (nr/nt). The parameters used were as follows: Max target sequences: 100, Expect threshold: 10, Matrix: Blosu62, Gap costs: Existence: 11, extension:1. Compositional adjustments: conditional compositional score adjustment; For EOBI and II homologies done using tblastp the search was done as a protein-protein Blast using non-redundant protein sequences (nr). The parameters used were as follows: Max target sequences: 100, Expect threshold: 10, Matrix: Blosu62, Gap costs: Existence: 11, extension:1, Compositional adjustments: conditional compositional score adjustment; For EOBI and II homologies done using blastn the search was done by Megablast using nucleotide collection data base (nr/nt). The parameters used were as follows: Max target sequences: 100, Expect threshold: 10, Scoring Parameters Matrix: Match/Mismatch Scores 1-2, Gap Costs: linear, Filters and Masking. Filter-low complexity regions. Mask-Mask for lookup table only; For EOBI and II homologies done using blastn in EST database the search was done by Megablast using Non-human, Non-mouse ESTs (est others) database. The parameters used were as follows: Max target sequences: 100, Expect threshold: 10, Scoring Parameters Matrix: Match/Mismatch Scores 1-2, Gap Costs: linear, Filters and Masking. Filter-low complexity regions. Mask-Mask for lookup table only.

According to exemplary embodiments of this aspect of the present invention the polynucleotide comprises a nucleic acid sequence as set forth in GenBank Accession No. NP_189074 (MYB305), GenBank Accession No. P81396 (MYB340), GenBank Accession No. NP_566467 (MYB26), GenBank Accession No. NP_189418 (AtMYB21), GenBank Accession No. NP_001106037.1 (MYB8), GenBank Accession No. NP_198851 (AtMYB24), GenBank Accession No. ABW34394 (VvMYB24) or GenBank Accession Nos. NP_201038, NP_193612, ABH02849, ABH02847 (MYB99, MYB98, MYB182, MYB181).

In a further exemplary embodiment, the polynucleotide comprises a nucleic acid sequence as set forth in SEQ ID NO: 58.

According to an exemplary embodiment the polynucleotide comprises a nucleic acid sequence as set forth in SEQ ID NO: 1, 51 or 53.

Alternatively or additionally the polynucleotide comprises a nucleic acid sequence encoding a polypeptide having an amino acid sequence as set forth in SEQ ID NO: 2, 52 and 54.

While further reducing the present invention to practice the present inventors identified novel MYB genes of the phenylpropanoid pathway.

Thus, the present invention further envisages a polynucleotide comprising a nucleic acid sequence at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or more say 100% identical to SEQ ID NO: 58.

According to an exemplary embodiment the myb gene comprises an amino acid sequence endogenous to the plant.

Thus, the present invention encompasses nucleic acid sequences described hereinabove; fragments thereof, sequences hybridizable therewith, sequences homologous thereto, sequences orthologous thereto, sequences encoding similar polypeptides with different codon usage, altered sequences characterized by mutations, such as deletion, insertion or substitution of one or more nucleotides, either naturally occurring or man induced, either randomly or in a targeted fashion.

As used herein, the phrase "phenylpropanoid pathway" refers to intracellular pathway within a plant cell which leads to the production of a phenylpropanoid compound.

As used herein, the phrase "phenylpropanoid compound" refers to a plant-derived organic compound that is biosynthesized from the amino acid phenylalanine (Phe). Typically the term phenylpropanoid compound encompasses both volatile and non-volatile compounds.

As used herein, the phrase "volatile compound" refers to a plant-derived organic product of the phenylpropanoid pathway that can be emitted from the plant into the atmosphere. The volatile compounds may be emitted from any part of the plant (e.g. vegetative tissues including roots, stems, twigs, and leaves) although typically they are emitted from flowers. These compounds include terpenoids, fatty acid derivatives, benzenoids and phenylpropanoids, C5-branched compounds and various nitrogen and sulfur containing compounds, including, but not limited to, phenylacetaldehyde, benzaldehyde, benzyl alcohol, phenylethyl alcohol, phenylethyl acetate, benzylacetate, eugenol, vanillin, benzylbenzoate, methylbenzoate, isoeugenol, benzaldehyde 4-hydroxy, benzaldehyde 3,4-dimethoxy (vanillin methyl ether), benzaldehyde 4-hydroxy 3-methoxy, orcinol methyl ether, orcinol dimethyl ether, methyleugenol, isomethyleugenol, methylsalicylate and 3,5-dimethoxytoluene.

As used herein, the term "non-volatile compound" refers to a plant-derived organic product of the phenylpropanoid pathway that is not emitted from the plant. Such compounds include, but are not limited to, anthocyanins, proanthocyanins, stilbenes, flavonoids, chalcones, aurones, coumarins, tannins, lignins, flavones and flavonols.

As used herein, the term "enhancing" refers to an increase in production of a phenylpropanoid compound, for example, by at least 5%, 10%, 15%, 20%, 30%, 50%, 100%, 200%, 250%, 400% or more. The increase in production of a phenylpropanoid compound may be in the emission level or in the internal pool level and can typically be determined with respect to a native plant [i.e., a plant not modified with the biomolecules (polynucleotide or polypeptides) of the invention, e.g., a non-genetically modified plant of the same species which is grown under the same growth conditions]. The enhanced production of a phenylpropanoid compound may be determined by any method known to one of ordinary skill in the art, as for example by headspace sampling, solvent extraction, solid phase micro extraction and the analysis by gas chromatography-mass spectrometry or any other analytical instrument.

As is shown in detail in the examples section which follows, the present inventors have uncovered new genes of the Myb transcription factor family in *Petunia* (designated herein as EOBI and EOBII, see Example 4, hereinbelow). Sequence analysis of these new polynucleotides showed that they encode for a 202 amino acid protein (EOBI) and a 197 amino acid protein (EOBII), both comprising the conserved Myb R2R3 binding domain and a W-MDDIW motif (FIG. 13A).

Thus, the invention further provides an isolated polypeptide having an amino acid sequence at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 93%, at least about 94%, at least about 95%, at least about 96%, at least about 97%, at least about 98%, at least about 99%, or more say 100% homologous to an amino acid sequence selected from the group consisting of SEQ ID NOs: 52 or 54.

According to some embodiments of the invention, the polypeptide is set forth by SEQ ID NOs: 52 or 54.

As mentioned the present inventors further identified novel myb homologues from *Solanum lycopersicum*.

Thus, the invention further provides an isolated polypeptide having an amino acid sequence at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 93%, at least about 94%, at least about 95%, at least about 96%, at least about 97%, at least about 98%, at least about 99%, or more say 100% homologous to an amino acid sequence as set forth in SEQ ID NOs: 59.

The term "plant" as used herein encompasses whole plants, ancestors and progeny of the plants and plant parts, including flower, leaf, root (including tubers), fruit, seed, shoot, stem, twig) and plant cells (homogeneous or heterogeneous populations of cells), tissues and organs. The plant may be in any form including suspension cultures, embryos, meristematic regions, callus tissue, leaves, gametophytes, sporophytes, pollen, and microspores. Plants that are particularly useful in the methods of the invention include all plants which are commercially or scientifically valuable and which taste, aroma or pigmentation modification is desired. A suitable plant for use with the method of the invention can be any potted plant, hydroponically-grown plant, field-grown plant, greenhouse-grown plant, in vitro-grown plant or a plant grown in a bioreactor including all plants which belong to the superfamily Viridiplantae, in particular monocotyledonous and dicotyledonous plants including a fodder or forage legume, ornamental plant, food crop, tree, or shrub selected from the list comprising *Acacia* spp., *Acer* spp., *Actinidia* spp., *Aesculus* spp., *Agathis australis*, *Albizia amara*, *Alsophila tricolor*, *Andropogon* spp., *Arachis* spp, *Areca catechu*, *Astelia fragrans*, *Astragalus cicer*, *Baikiaea plurijuga*, *Betula* spp., *Brassica* spp., *Bruguiera gymnorrhiza*, *Burkea africana*, *Butea frondosa*, *Cadaba farinosa*, *Calliandra* spp, *Camellia sinensis*, *Canna indica*, *Capsicum* spp., *Cassia* spp., *Centroema pubescens*, *Chacoomeles* spp., *Cinnamomum cassia*, *Coffea arabica*, *Colophospermum mopane*, *Coronillia varia*, *Cotoneaster serotina*, *Crataegus* spp., *Cucumis* spp., *Cupressus* spp., *Cyathea dealbata*, *Cydonia oblonga*, *Cryptomeria japonica*, *Cymbopogon* spp., *Cynthea dealbata*, *Cydonia oblonga*, *Dalbergia monetaria*, *Davallia divaricata*, *Desmodium* spp., *Dicksonia squarosa*, *Dibeteropogon amplectens*, *Dioclea* spp, *Dolichos* spp., *Dorycnium rectum*, *Echinochloa pyramidalis*, *Ehraffia* spp., *Eleusine coracana*, *Eragrestis* spp., *Erythrina* spp., *Eucalypfus* spp., *Euclea schimperi*, *Eulalia vi/losa*, *Pagopyrum* spp., *Feijoa sellowlana*, *Fragaria* spp., *Flemingia* spp, *Freycinetia banksli*, *Geranium thunbergii*, *GinAgo biloba*, *Glycine javanica*, *Gliricidia* spp, *Gossypium hirsutum*, *Grevillea* spp., *Guibourtia coleosperma*, *Hedysarum* spp., *Hemaffhia altissima*, *Heteropogon contoffus*, *Hordeum vulgare*, *Hyparrhenia rufa*, *Hypericum erectum*, *Hypeffhelia dissolute*, *Indigo incamata*, *Iris* spp., *Leptarrhena pyrolifolia*, *Lespediza* spp., *Lettuca* spp., *Leucaena leucocephala*, *Loudetia simplex*, *Lotonus bainesli*, *Lotus* spp., *Macrotyloma axillare*, *Malus* spp., *Manihot esculenta*, *Medicago saliva*, *Metasequoia glyptostroboides*, *Musa sapientum*, *Nicotianum* spp., *Onobrychis* spp., *Ornithopus* spp., *Oryza* spp., *Peltophorum africanum*, *Pennisetum* spp., *Persea gratissima*, *Petunia* spp., Caryophyllaceae, Lamiaceae, *Phaseolus* spp., *Phoenix canariensis*, *Phormium cookianum*, *Photinia* spp., *Picea glauca*, *Pinus* spp., *Pisum sativam*, *Podocarpus totara*, *Pogonarthria fleckii*, *Pogonaffhria squarrosa*, *Populus* spp., *Prosopis cineraria*, *Pseudotsuga menziesii*, *Pterolobium stellatum*, *Pyrus communis*, *Quercus* spp., *Rhaphiolepsis umbellata*, *Rhopalostylis sapida*, *Rhus natalensis*, *Ribes grossularia*, *Ribes* spp., *Robinia pseudoacacia*, *Rosa* spp., *Rubus* spp., *Salix* spp., *Schyzachyrium sanguineum*, *Sciadopitys vefficillata*, *Sequoia sempervirens*, *Sequoiadendron giganteum*, Solanaceae sp., *Sorghum bicolor*, *Spinacia* spp., *Sporobolus fimbriatus*, *Stiburus alopecuroides*, *Stylosanthos humilis*, *Tadehagi* spp, *Taxodium distichum*, *Themeda triandra*, *Trifolium* spp., *Triticum* spp., *Tsuga heterophylla*, *Vaccinium* spp., *Vicia* spp., *Vitis vinifera*, *Watsonia pyramidata*, *Zantedeschia aethiopica*, *Zea mays*, amaranth, artichoke, asparagus, broccoli, Brussels sprouts, cabbage, canola, carrot, cauliflower, celery, collard greens, flax, kale, lentil, oilseed rape, okra, onion, potato, rice, soybean, straw, sugar beet, sugar cane, sunflower, tomato, squash tea, trees, as well as other plants listed in World Wide Web (dot) nationmaster (dot) com/encyclopedia/Plantae. Alternatively algae and other non-Viridiplantae can be used for the methods of the present invention.

According to an exemplary embodiment of the present invention, the plant is a petunia.

As used herein the phrase "plant cell" refers to isolated plant cells which are derived from disintegrated plant cell tissue or plant cell culture. As used herein the phrase "plant cell culture" refers to any type of native (naturally occurring) plant cells, plant cell lines and genetically modified plant cells, which are not assembled to form a complete plant, such that at least one biological structure of a plant is not present. Optionally, the plant cell culture may comprise a particular type of a plant cell or a plurality of different types of plant cells. It should be noted that optionally plant cultures featuring a particular type of plant cell may be originally derived from a plurality of different types of such plant cells.

It will be appreciated that enhancing production of a phenylpropanoid compound in a plant or plant cell may be further enhanced by upregulating in the plant or plant cell at least one substrate of the phenylpropanoid pathway, the substrate being upstream to the production of the phenylpropanoid compound, thereby enhancing the production of the phenylpropanoid compound in the plant or plant cell.

As used herein the phrase "a substrate of the phenylpropanoid pathway" refers to a molecule which may be enzymatically processed by an enzyme of the phenylpropanoid pathway. Any substrate upstream to the production of the phenylpropanoid compound is contemplated according to the present teachings including, but not limited to, phenylalanine, cinnamic acid, benzoic acid, coumaric acid, orcinol, salicylic acid, coniferyl alcohol, coniferyl acetate and ferulic acid.

Upregulating the substrate may be effected by contacting the plant or plant cell with the substrate; or alternatively or additionally by expressing in the plant or plant cell an enzyme capable of producing a substrate of the phenylpropanoid pathway.

As used herein the term "contacting" refers to externally supplying the plant or plant cell with a substrate as to upregulate its intracellular substrate levels. Any method of contacting a plant or plant cell may be used according to the present teachings, for example, a plant may be "fed" with the substrate e.g., L-phenylalanine (L-Phe, e.g. from Duchefa, Haarlem, Netherlands) via addition of the L-Phe to the plant's water supply or soil/hydroponic as described in detail in Example 1 of the example section which follows. Alternatively, the substrate may be added to the plant cell culture via addition to the cell growth medium. In the same way any substrate including cinnamic acid, benzoic acid, coumaric acid, orcinol, salicylic acid, coniferyl alcohol, coniferyl acetate and ferulic acid (all available from Sigma or Merck catalogue) may be contacted with the plant or plant cell.

As mentioned, upregulating the substrate may be effected by expressing an enzyme participating in the biosynthetic production of the substrate in the plant or plant cell.

This can be achieved, for example, by upregulating expression of genes which catalyze the substrate's (e.g. phenylalanine) biosynthesis. For example, L-Phe, may be catalyzed via a process which starts with Chorismate which is converted to Prephenate by the action of Chorismate mutase (CM). Prephenate is then converted to Phenylpyruvate via the action of Prephenate dehydratase (PDT). Consequently, Phenylpyruvate is catalyzed into L-Phenylalanine Enzymes catalyzing these steps have been characterized, some possessing merely PDT activity, and some (p-proteins) are multifunctional, possessing both CM (Chorismate mutase) as well as PDT activities [Warpeha et al. (2006) Plant Physiol. 140: 844-855]. Alternatively, Phe biosynthesis may occur via transamination of Prephenate to Arogenate via Prephenate aminotransferase (PAT), followed by dehydration/decarboxylation by Arogenate dehydratase (ADT). In some instances, a third enzyme Cyclohexadienyl dehydratase (CDT) is reported to have both PDT and ADT activities [Warpeha et al., supra].

Thus, according to an exemplary embodiment of the present invention, a polynucleotide which encodes for a polypeptide that catalyzes biosynthesis of a substrate of the phenylpropanoid pathway may be expressed in a plant or plant cell. Examples of such polynucleotides include, but are not limited to, prephenate dehydratase (PDT, such as set forth in GenBank Accession No. NP_014083 or a plant homologue of same), chorismate mutase (CM, such as set forth in GenBank Accession Nos. NP_566846, NP_177096), prephenate aminotransferase (PAT, such as set forth in GenBank Accession No. YP_001581880 or a plant homologue of same), arogenate dehydratase (ADT, such as set forth in GenBank Accession Nos. NP_563809, NP_197655, NP_187420, NP_190058, NP_001031024) and cyclohexadienyl dehydratase (CDT, such as set forth in GenBank Accession No. YP_970819 or a plant homologue of same).

According to some embodiments of the invention, upregulation of the substrate leads to an enhanced production of phenylpropanoid compound by at least 2 fold, at least 3 fold, at least 4 fold, at least 5 fold, at least 6 fold, at least 7 fold, at least 8 fold, at least 9 fold, or at least 10 fold as compared to a control plant [i.e., a plant not modified with the above-polynucleotide sequences, e.g., a non-genetically modified plant of the same species, but are otherwise of the same developmental age and grown under the same growth conditions].

It will be appreciated that upregulation of the substrate and/or myb polynucleotide may be effected during different hours of the day (i.e. during the day or night) as to maximize phenylpropanoid production (e.g. emission of volatile compounds).

As was shown by the present inventors (see Example 3, of the Examples section which follows), Phe feeding of Pap1-transgenic *petunia* flowers during the day leads to increased volatile emission to the level of volatile emission at night (FIGS. 7A-C) and thus abolishes the nocturnal rhythmus. It is important to note that the combination of Pap1-expression and Phe feeding leads to a continuous and strong volatile production during both day and night.

Thus, for example the substrate and/or myb polynucleotide is upregulated during the day as to maximize production of phenylpropanoid compounds during the day in plants having a high scent emission at night.

In other exemplary embodiments the substrate and/or myb polynucleotide is upregulated during the night as to maximize production of phenylpropanoid compounds during the night in plants having a high scent emission during the day.

Furthermore, expression of any of the polynucleotides described herein may be effected during predetermined developmental stages of the plant (e.g. from a young bud to a wilting stage as for example a flower pre anthesis, at anthesis or 1 day post anthesis) or in a tissue specific manner (e.g. in a flower) as will be explained in further detail hereinbelow.

Methods of genetically modifying whole plants, portions thereof or plant cells (which may be followed by plant regeneration) are well known in the art, some are discussed infra.

Constructs useful in the methods according to the present invention may be constructed using recombinant DNA technology well known to persons skilled in the art. The gene constructs may be inserted into vectors, which may be commercially available, suitable for transforming into plants and suitable for expression of the gene of interest in the transformed cells. The genetic construct can be an expression vector wherein said nucleic acid sequence is operably linked to one or more regulatory sequences allowing expression in the plant cells.

In a particular embodiment of the present invention the regulatory sequence is a plant-expressible promoter.

As used herein the phrase "plant-expressible promoter" refers to a promoter sequence, including any additional regulatory elements added thereto or contained therein, is at least capable of inducing, conferring, activating or enhancing expression in a plant cell, tissue or organ, preferably a monocotyledonous or dicotyledonous plant cell, tissue, or organ. Any suitable promoter sequence can be used in a nucleic acid construct used in accordance with the present invention. Preferably the promoter is a constitutive promoter, a tissue/developmental-specific promoter or an inducible promoter. Examples of preferred promoters useful for the methods of the present invention are presented in Table 3, 4, 5 and 6.

TABLE 3

Exemplary constitutive promoters for use in the performance of the present invention

| Gene Source | Expression Pattern | Reference |
| --- | --- | --- |
| Actin | constitutive | McElroy et. al, Plant Cell, 2: 163-171, 1990 |
| CAMV 35S | constitutive | Odell et al, Nature, 313: 810-812, 1985 |
| CaMV 19S | constitutive | Nilsson et al., Physiol. Plant 100: 456-462, 1997 |
| GOS2 | constitutive | de Pater et al, Plant J Nov; 2(6): 837-44, 1992 |
| ubiquitin | constitutive | Christensen et al, Plant Mol. Biol. 18: 675-689, 1992 |
| Rice cyclophilin | constitutive | Bucholz et al, Plant Mol Biol. 25(5): 837-43, 1994 |
| Maize H3 histone | constitutive | Lepetit et al, Mol. Gen. Genet. 231: 276-285, 1992 |
| Actin 2 | constitutive | An et al, Plant J. 10(1); 107-121, 1996 |

TABLE 4

Exemplary seed-preferred promoters for use in the performance of the present invention

| Gene Source | Expression Pattern | Reference |
| --- | --- | --- |
| Seed specific genes | seed | Simon, et al., Plant Mol. Biol. 5. 191, 1985; Scofield, etal., J. Biol. Chem. 262: 12202, 1987.; Baszczynski, et al., Plant Mol. Biol. 14: 633, 1990. |
| Brazil Nut albumin | seed | Pearson' et al., Plant Mol. Biol. 18: 235-245, 1992. |
| legumin | seed | Ellis, et al. Plant Mol. Biol. 10: 203-214, 1988 |
| Glutelin (rice) | seed | Takaiwa, et al., Mol. Gen. Genet. 208: 15-22, 1986; Takaiwa, et al., FEBS Letts. 221: 43-47, 1987 |
| Zein | seed | Matzke et al Plant Mol Biol, 143). 323-32 1990 |
| napA | seed | Stalberg, et al, Planta 199: 515-519, 1996 |
| wheat LMW and HMW, glutenin-1 | endosperm | Mol Gen Genet 216: 81-90, 1989; NAR 17: 461-2, |
| Wheat SPA | seed | Albanietal, Plant Cell, 9: 171-184, 1997 |
| wheat a, b and g gliadins | endosperm | EMBO3: 1409-15, 1984 |
| Barley ltr1 promoter | endosperm | |
| barley B1, C, D hordein | endosperm | Theor Appl Gen 98: 1253-62, 1999; Plant J 4: 343-55, 1993; Mol Gen Genet 250: 750-60, 1996 |
| Barley DOF | endosperm | Mena et al, The Plant Journal, 116(1): 53-62, 1998 |
| Biz2 | endosperm | EP99106056.7 |
| Synthetic promoter | endosperm | Vicente-Carbajosa et al., Plant J. 13: 629-640, 1998 |
| rice prolamin NRP33 | endosperm | Wu et al, Plant Cell Physiology 39(8) 885-889, 1998 |
| rice-globulin Glb-1 | endosperm | Wu et al, Plant Cell Physiology 398) 885-889, 1998 |
| rice OSH1 | emryo | Sato et al, Proc. Nati. Acad. Sci. USA, 93: 8117-8122 |
| rice alpha-globulin REB/OHP-1 | endosperm | Nakase et al. Plant Mol. Biol. 33: 513-S22, 1997 |
| rice ADP-glucose PP | endosperm | Trans Res 6: 157-68, 1997 |
| maize ESR gene family | endosperm | Plant J 12: 235-46, 1997 |
| sorgum gamma-kafirin | endosperm | PMB 32: 1029-35, 1996 |
| KNOX | emryo | Postma-Haarsma et al, Plant Mol. Biol. 39: 257-71, 1999 |
| rice oleosin | Embryo and aleuton | Wu et at, J. Biochem., 123: 386, 1998 |
| sunflower oleosin | Seed (embryo and dry seed) | Cummins, etal., Plant Mol. Biol. 19: 873-876, 1992 |

TABLE 5

Exemplary flower-specific promoters for use in the performance of the invention

| Gene Source | Expression Pattern | Reference |
|---|---|---|
| AtPRP4 | flowers | www.//salus. medium.edu/mmg/tierney/html |
| chalene synthase (chsA) | flowers | Van der Meer, et al., Plant Mol. Biol. 15, 95-109, 1990. |
| LAT52 | anther | Twell et al Mol. Gen Genet. 217: 240-245 (1989) |
| apetala-3 | flowers | |

TABLE 6

Alternative rice promoters for use in the performance of the invention

| PRO # | gene | expression |
|---|---|---|
| PR00001 | Metallothionein Mte | transfer layer of embryo + calli |
| PR00005 | putative beta-amylase | transfer layer of embryo |
| PR00009 | Putative cellulose synthase | Weak in roots |
| PR00012 | lipase (putative) | |
| PR00014 | Transferase (putative) | |
| PR00016 | peptidyl prolyl cis-trans isomerase (putative) | |
| PR00019 | unknown | |
| PR00020 | prp protein (putative) | |
| PR00029 | noduline (putative) | |
| PR00058 | Proteinase inhibitor Rgpi9 | seed |
| PR00061 | beta expansine EXPB9 | Weak in young flowers |
| PR00063 | Structural protein | young tissues + calli + embryo |
| PR00069 | xylosidase (putative) | |
| PR00075 | Prolamine 10 Kda | strong in endosperm |
| PR00076 | allergen RA2 | strong in endosperm |
| PR00077 | prolamine RP7 | strong in endosperm |
| PR00078 | CBP80 | |
| PR00079 | starch branching enzyme I | |
| PR00080 | Metallothioneine-like ML2 | transfer layer of embryo + calli |
| PR00081 | putative caffeoyl-CoA 3-0 methyltransferase | shoot |
| PR00087 | prolamine RM9 | strong in endosperm |
| PR00090 | prolamine RP6 | strong in endosperm |
| PR00091 | prolamine RP5 | strong in endosperm |
| PR00092 | allergen RA5 | |
| PR00095 | putative methionine aminopeptidase | embryo |
| PR00098 | ras-related GTP binding protein | |
| PR00104 | beta expansine EXPB1 | |
| PR00105 | Glycine rich protein | |
| PR00108 | metallothionein like protein (putative) | |
| PR00110 | RCc3 strong root | |
| PR00111 | uclacyanin 3-like protein | weak discrimination center/ shoot meristem |
| PR00116 | 26S proteasome regulatory particle non-ATPase subunit 11 | very weak meristem specific |
| PR00117 | putative 40S ribosomal protein | weak in endosperm |
| PR00122 | chlorophyll a/lo-binding protein precursor (Cab27) | very weak in shoot |
| PR00123 | putative protochlorophyllide reductase | Strong leaves |
| PR00126 | metallothionein RiCMT | strong discrimination center shoot meristem |
| PR00129 | GOS2 | Strong constitutive |
| PR00131 | GOS9 | |
| PR00133 | chitinase Cht-3 | very weak meristem specific |
| PR00135 | alpha-globulin | Strong in endosperm |
| PR00136 | alanine aminotransferase | Weak in endosperm |
| PR00138 | Cyclin A2 | |
| PR00139 | Cyclin D2 | |
| PR00140 | Cyclin D3 | |
| PR00141 | Cyclophyllin 2 | Shoot and seed |
| PR00146 | sucrose synthase SS1 (barley) | medium constitutive |
| PR00147 | trypsin inhibitor ITR1 (barley) | weak in endosperm |
| PR00149 | ubiquitine 2 with intron | strong constitutive |
| PR00151 | WSI18 | Embryo and stress |
| PR00156 | HVA22 homologue (putative) | |
| PR00157 | EL2 | |
| PR00169 | aquaporine | medium constitutive in young plants |

TABLE 6-continued

Alternative rice promoters for use in the performance of the invention

| PRO # | gene | expression |
|---|---|---|
| PR00170 | High mobility group protein | Strong constitutive |
| PR00171 | reversibly glycosylated protein RGP1 | weak constitutive |
| PR00173 | cytosolic MDH | shoot |
| PR00175 | RAB21 | Embryo and stress |
| PR00176 | CDPK7 | |
| PR00177 | Cdc2-1 | very weak in meristem |
| PR00197 | sucrose synthase 3 | |
| PRO0198 | OsVP1 | |
| PRO0200 | OSH1 | very weak in young plant meristem |
| PRO0208 | putative chlorophyllase | |
| PRO0210 | OsNRT1 | |
| PRO0211 | EXP3 | |
| PRO0216 | phosphate transporter OjPT1 | |
| PRO0218 | oleosin 18 kd | aleurone + embryo |
| PRO0219 | ubiquitine 2 without intron | |
| PRO0220 | RFL | |
| PRO0221 | maize UBI delta intron | not detected |
| PRO0223 | glutelin-1 | |
| PRO0224 | fragment of prolamin RP6 promoter | |
| PRO0225 | 4xABRE | |
| PRO0226 | glutelin OSGLUA3 | |
| PRO0227 | BLZ-2__short (barley) | |
| PR00228 | BLZ-2__long (barley) | |

Examples of inducible promoters include, but are not limited to, salt-inducible promoters such as RD29A (Yamaguchi-Shinozalei et al., Mol. Gen. Genet. 236:331-340, 1993); drought-inducible promoters such as maize rab17 gene promoter (Pla et. al., Plant Mol. Biol. 21:259-266, 1993), maize rab28 gene promoter (Busk et. al., Plant J. 11:1285-1295, 1997) and maize Ivr2 gene promoter (Pelleschi et. al., Plant Mol. Biol. 39:373-380, 1999); heat-inducible promoters such as heat tomato hsp80-promoter from tomato (U.S. Pat. No. 5,187,267) and light inducible promoters e.g. of the Cab gene family (White et al., PLANT PHYSIOLOGY, Vol 107, Issue 1 161-165, 1995).

Nucleic acid sequences of the polypeptides of the present invention may be optimized for plant expression. Examples of such sequence modifications include, but are not limited to, an altered G/C content to more closely approach that typically found in the plant species of interest, and the removal of codons atypically found in the plant species commonly referred to as codon optimization.

The phrase "codon optimization" refers to the selection of appropriate DNA nucleotides for use within a structural gene or fragment thereof that approaches codon usage within the plant of interest. Therefore, an optimized gene or nucleic acid sequence refers to a gene in which the nucleotide sequence of a native or naturally occurring gene has been modified in order to utilize statistically-preferred or statistically-favored codons within the plant. The nucleotide sequence typically is examined at the DNA level and the coding region optimized for expression in the plant species determined using any suitable procedure, for example as described in Sardana et al. (1996, Plant Cell Reports 15:677-681). A table of codon usage from highly expressed genes of dicotyledonous plants is compiled using the data of Murray et al. (1989, Nuc Acids Res. 17:477-498).

Nucleic acid constructs of the present invention preferably further include an appropriate selectable marker and/or an origin of replication. Preferably, the nucleic acid construct utilized is a shuttle vector, which can propagate both in E. coli (wherein the construct comprises an appropriate selectable marker and origin of replication) and be compatible with propagation in cells. The construct according to the present invention can be, for example, a plasmid, a bacmid, a phagemid, a cosmid, a phage, a virus or an artificial chromosome.

Plant cells may be transformed stably or transiently with the nucleic acid constructs of the present invention. In stable transformation, the nucleic acid molecule of the present invention is integrated into the plant genome and as such it represents a stable and inherited trait. In transient transformation, the nucleic acid molecule is expressed by the cell transformed but it is not integrated into the genome and as such it represents a transient trait.

There are various methods of introducing foreign genes into both monocotyledonous and dicotyledonous plants (Potrykus, I., Annu Rev. Plant. Physiol., Plant. Mol. Biol. (1991) 42:205-225; Shimamoto et al., Nature (1989) 338:274-276).

The principle methods of causing stable integration of exogenous DNA into plant genomic DNA include two main approaches:

(i) Agrobacterium-mediated gene transfer: Klee et al. (1987) Annu Rev. Plant Physiol. 38:467-486; Klee and Rogers in Cell Culture and Somatic Cell Genetics of Plants, Vol. 6, Molecular Biology of Plant Nuclear Genes, eds. Schell, J., and Vasil, L. K., Academic Publishers, San Diego, Calif. (1989) p. 2-25; Gatenby, in Plant Biotechnology, eds. Kung, S, and Arntzen, C. J., Butterworth Publishers, Boston, Mass. (1989) p. 93-112.

(ii) direct DNA uptake: Paszkowski et al., in Cell Culture and Somatic Cell Genetics of Plants, Vol. 6, Molecular Biology of Plant Nuclear Genes eds. Schell, J., and Vasil, L. K., Academic Publishers, San Diego, Calif. (1989) p. 52-68; including methods for direct uptake of DNA into protoplasts, Toriyama, K. et al. (1988) Bio/Technology 6:1072-1074. DNA uptake induced by brief electric shock of plant cells: Zhang et al. Plant Cell Rep. (1988) 7:379-384. Fromm et al. Nature (1986) 319:791-793. DNA injection into plant cells or tissues by particle bombardment, Klein et al. Bio/Technology (1988) 6:559-563; McCabe et al. Bio/Technology (1988) 6:923-926; Sanford, Physiol. Plant. (1990) 79:206-209; by the use of micropipette systems: Neuhaus et al., Theor. Appl.

Genet. (1987) 75:30-36; Neuhaus and Spangenberg, Physiol. Plant. (1990) 79:213-217; glass fibers or silicon carbide whisker transformation of cell cultures, embryos or callus tissue, U.S. Pat. No. 5,464,765 or by the direct incubation of DNA with germinating pollen, DeWet et al. in Experimental Manipulation of Ovule Tissue, eds. Chapman, G. P. and Mantell, S. H. and Daniels, W. Longman, London, (1985) p. 197-209; and Ohta, Proc. Natl. Acad. Sci. USA (1986) 83:715-719.

The *Agrobacterium* system includes the use of plasmid vectors that contain defined DNA segments that integrate into the plant genomic DNA. Methods of inoculation of the plant tissue vary depending upon the plant species and the *Agrobacterium* delivery system. A widely used approach is the leaf disc procedure which can be performed with any tissue explant that provides a good source for initiation of whole plant differentiation. Horsch et al. in Plant Molecular Biology Manual A5, Kluwer Academic Publishers, Dordrecht (1988) p. 1-9. A supplementary approach employs the *Agrobacterium* delivery system in combination with vacuum infiltration. The *Agrobacterium* system is especially viable in the creation of transgenic dicotyledonous plants.

There are various methods of direct DNA transfer into plant cells. In electroporation, the protoplasts are briefly exposed to a strong electric field. In microinjection, the DNA is mechanically injected directly into the cells using very small micropipettes. In microparticle bombardment, the DNA is adsorbed on microprojectiles such as magnesium sulfate crystals or tungsten particles, and the microprojectiles are physically accelerated into cells or plant tissues.

Following stable transformation plant propagation is exercised. The most common method of plant propagation is by seed. Regeneration by seed propagation, however, has the deficiency that due to heterozygosity there is a lack of uniformity in the crop, since seeds are produced by plants according to the genetic variances governed by Mendelian rules. Basically, each seed is genetically different and each will grow with its own specific traits. Therefore, it is preferred that the transformed plant be produced such that the regenerated plant has the identical traits and characteristics of the parent transgenic plant. Therefore, it is preferred that the transformed plant be regenerated by vegetative/micropropagation which provides a rapid, consistent reproduction of the transformed plants.

Micropropagation is a process of growing new generation plants from a single piece of tissue that has been excised from a selected parent plant or cultivar. This process permits the mass reproduction of plants having the preferred tissue expressing the fusion protein. The new generation plants which are produced are genetically identical to, and have all of the characteristics of, the original plant. Micropropagation allows mass production of quality plant material in a short period of time and offers a rapid multiplication of selected cultivars in the preservation of the characteristics of the original transgenic or transformed plant. The advantages of cloning plants are the speed of plant multiplication and the quality and uniformity of plants produced.

Micropropagation is a multi-stage procedure that requires alteration of culture medium or growth conditions between stages. Thus, the micropropagation process involves four basic stages: Stage one, initial tissue culturing; stage two, tissue culture multiplication; stage three, differentiation and plant formation; and stage four, greenhouse culturing and hardening. During stage one, initial tissue culturing, the tissue culture is established and certified contaminant-free. During stage two, the initial tissue culture is multiplied until a sufficient number of tissue samples are produced to meet production goals. During stage three, the tissue samples grown in stage two are divided and grown into individual plantlets. At stage four, the transformed plantlets are transferred to a greenhouse for hardening where the plants' tolerance to light is gradually increased so that it can be grown in the natural environment.

Although stable transformation is presently preferred, transient transformation of leaf cells, meristematic cells or the whole plant is also envisaged by the present invention.

Transient transformation can be effected by any of the direct DNA transfer methods described above or by viral infection using modified plant viruses.

Viruses that have been shown to be useful for the transformation of plant hosts include CaMV, TMV and BV. Transformation of plants using plant viruses is described in U.S. Pat. No. 4,855,237 (BGV), EP-A 67,553 (TMV), Japanese Published Application No. 63-14693 (TMV), EPA 194,809 (BV), EPA 278,667 (BV); and Gluzman, Y. et al., Communications in Molecular Biology: Viral Vectors, Cold Spring Harbor Laboratory, New York, pp. 172-189 (1988). Pseudovirus particles for use in expressing foreign DNA in many hosts, including plants, is described in WO 87/06261.

Construction of plant RNA viruses for the introduction and expression of non-viral exogenous nucleic acid sequences in plants is demonstrated by the above references as well as by Dawson, W. O. et al., Virology (1989) 172:285-292; Takamatsu et al. EMBO J. (1987) 6:307-311; French et al. Science (1986) 231:1294-1297; and Takamatsu et al. FEBS Letters (1990) 269:73-76.

When the virus is a DNA virus, suitable modifications can be made to the virus itself. Alternatively, the virus can first be cloned into a bacterial plasmid for ease of constructing the desired viral vector with the foreign DNA. The virus can then be excised from the plasmid. If the virus is a DNA virus, a bacterial origin of replication can be attached to the viral DNA, which is then replicated by the bacteria. Transcription and translation of this DNA will produce the coat protein which will encapsidate the viral DNA. If the virus is an RNA virus, the virus is generally cloned as a cDNA and inserted into a plasmid. The plasmid is then used to make all of the constructions. The RNA virus is then produced by transcribing the viral sequence of the plasmid and translation of the viral genes to produce the coat protein(s) which encapsidate the viral RNA.

Construction of plant RNA viruses for the introduction and expression in plants of non-viral exogenous nucleic acid sequences such as those included in the construct of the present invention is demonstrated by the above references as well as in U.S. Pat. No. 5,316,931.

In one embodiment, a plant viral nucleic acid is provided in which the native coat protein coding sequence has been deleted from a viral nucleic acid, a non-native plant viral coat protein coding sequence and a non-native promoter, preferably the subgenomic promoter of the non-native coat protein coding sequence, capable of expression in the plant host, packaging of the recombinant plant viral nucleic acid, and ensuring a systemic infection of the host by the recombinant plant viral nucleic acid, has been inserted. Alternatively, the coat protein gene may be inactivated by insertion of the non-native nucleic acid sequence within it, such that a protein is produced. The recombinant plant viral nucleic acid may contain one or more additional non-native subgenomic promoters. Each non-native subgenomic promoter is capable of transcribing or expressing adjacent genes or nucleic acid sequences in the plant host and incapable of recombination with each other and with native subgenomic promoters. Non-native (foreign) nucleic acid sequences may be inserted adjacent the native plant viral subgenomic promoter or the native and a non-native plant viral subgenomic promoters if more than one nucleic acid sequence is included. The non-native nucleic acid sequences are transcribed or expressed in the host plant under control of the subgenomic promoter to produce the desired products.

In a second embodiment, a recombinant plant viral nucleic acid is provided as in the first embodiment except that the native coat protein coding sequence is placed adjacent one of the non-native coat protein subgenomic promoters instead of a non-native coat protein coding sequence.

In a third embodiment, a recombinant plant viral nucleic acid is provided in which the native coat protein gene is adjacent its subgenomic promoter and one or more non-native subgenomic promoters have been inserted into the viral nucleic acid. The inserted non-native subgenomic promoters are capable of transcribing or expressing adjacent genes in a plant host and are incapable of recombination with each other and with native subgenomic promoters. Non-native nucleic acid sequences may be inserted adjacent the non-native subgenomic plant viral promoters such that said sequences are transcribed or expressed in the host plant under control of the subgenomic promoters to produce the desired product.

In a fourth embodiment, a recombinant plant viral nucleic acid is provided as in the third embodiment except that the native coat protein coding sequence is replaced by a non-native coat protein coding sequence.

The viral vectors are encapsidated by the coat proteins encoded by the recombinant plant viral nucleic acid to produce a recombinant plant virus. The recombinant plant viral nucleic acid or recombinant plant virus is used to infect appropriate host plants. The recombinant plant viral nucleic acid is capable of replication in the host, systemic spread in the host, and transcription or expression of foreign gene(s) (isolated nucleic acid) in the host to produce the desired protein.

In addition to the above, the nucleic acid molecule of the present invention can also be introduced into a chloroplast genome thereby enabling chloroplast expression.

A technique for introducing exogenous nucleic acid sequences to the genome of the chloroplasts is known. This technique involves the following procedures. First, plant cells are chemically treated so as to reduce the number of chloroplasts per cell to about one. Then, the exogenous nucleic acid is introduced via particle bombardment into the cells with the aim of introducing at least one exogenous nucleic acid molecule into the chloroplasts. The exogenous nucleic acid is selected such that it is integratable into the chloroplast's genome via homologous recombination which is readily effected by enzymes inherent to the chloroplast. To this end, the exogenous nucleic acid includes, in addition to a gene of interest, at least one nucleic acid stretch which is derived from the chloroplast's genome. In addition, the exogenous nucleic acid includes a selectable marker, which serves by sequential selection procedures to ascertain that all or substantially all of the copies of the chloroplast genomes following such selection will include the exogenous nucleic acid. Further details relating to this technique are found in U.S. Pat. Nos. 4,945,050; and 5,693,507 which are incorporated herein by reference. A polypeptide can thus be produced by the protein expression system of the chloroplast and become integrated into the chloroplast's inner membrane.

Since the present teachings contemplate expression of several different genes (e.g. a myb gene and a gene for catalyzing biosynthesis of a substrate) the present invention envisages expressing a plurality of exogenous polynucleotides in a single host plant to thereby achieve superior phenylpropanoid production.

Expressing a plurality of exogenous polynucleotides in a single host plant can be effected by co-introducing multiple nucleic acid constructs, each including a different exogenous polynucleotide, into a single plant cell. The transformed cell can then be regenerated into a mature plant using the methods described hereinabove.

Thus, according to an exemplary embodiment, a nucleic acid construct system comprising: (i) a first nucleic acid construct comprising a first nucleic acid sequence encoding a myb gene of the phenylpropanoid pathway; and (ii) a second nucleic acid construct comprising a second nucleic acid sequence encoding a gene for catalyzing biosynthesis of at least one substrate of the phenylpropanoid pathway; wherein the first nucleic acid sequence and the second nucleic acid sequence are under transcription control of a cis-acting regulatory element.

Alternatively, expressing a plurality of exogenous polynucleotides in a single host plant can be effected by co-introducing into a single plant-cell a single nucleic-acid construct including a plurality of different exogenous polynucleotides.

In an exemplary embodiment there is provided a nucleic acid construct comprising a first nucleic acid sequence encoding a myb gene of the phenylpropanoid pathway, as described above and a second nucleic acid sequence encoding an enzyme for catalyzing biosynthesis of at least one substrate of the phenylpropanoid pathway, wherein the first nucleic acid sequence and the second nucleic acid sequence are under transcription control of at least one cis-acting regulatory element.

Such a construct can be designed with a single promoter sequence which can transcribe a polycistronic message including all the different exogenous polynucleotide sequences. To enable co-translation of the different polypeptides encoded by the polycistronic message, the polynucleotide sequences can be inter-linked via an internal ribosome entry site (IRES) sequence which facilitates translation of polynucleotide sequences positioned downstream of the IRES sequence. In this case, a transcribed polycistronic RNA molecule encoding the different polypeptides described above will be translated from both the capped 5' end and the two internal IRES sequences of the polycistronic RNA molecule to thereby produce in the cell all different polypeptides. Alternatively, the construct can include several promoter sequences each linked to a different exogenous polynucleotide sequence.

The plant cell genetically modified with the construct including a plurality of different exogenous polynucleotides, can be regenerated into a mature plant, using the methods described hereinabove.

Alternatively, expressing a plurality of exogenous polynucleotides in a single host plant can be effected by introducing different nucleic acid constructs, including different exogenous polynucleotides, into a plurality of plants. The regenerated transformed plants can then be cross-bred and resultant progeny selected for superior phenylpropanoid production, using conventional plant breeding techniques.

Understanding of the role of myb genes in the phenylpropanoid pathway suggests not only upregulation of the pathway but also down regulation of the pathway such as in order to reduce production of irritating volatiles (i.e., overall modulation of the pathway).

Thus according to an aspect of the present invention there is provided a method of reducing production of a phenylpropanoid compound in a plant or plant cell, the method comprising downregulating expression of a myb gene of the phenylpropanoid pathway in the plant or plant cell, thereby reducing production of the phenylpropanoid compound.

As used herein, the term "reducing" refers to a decrease in production of a phenylpropanoid compound, for example, by at least 5%, 10%, 15%, 20%, 30%, 40%, 50%, 60%, 70%, 80%, 90% or more. The decrease in production of a phenylpropanoid compound may be in the emission level or in the internal pool level and can typically be determined with respect to a native plant [i.e., a plant not modified with the biomolecules (polynucleotide or polypeptides) of the invention, e.g., a non-genetically modified plant of the same species which is grown under the same growth conditions]. The decreased production of a phenylpropanoid compound may be determined by any method known to one of ordinary skill in the art, as for example by headspace sampling, solvent extraction, solid phase micro extraction and the analysis by gas chromatography-mass spectrometry or any other analytical instrument.

It will be appreciated that any method known to one of ordinary skill in the art can be used to downregulate expression of a myb gene of the phenylpropanoid pathway.

Downregulation of myb gene expression can be effected on the genomic and/or the transcript level using a variety of molecules which interfere with transcription and/or translation (e.g., RNA silencing agents, Ribozyme, DNAzyme and antisense), or on the protein level using e.g., antagonists, enzymes that cleave the polypeptide and the like.

Downregulation of myb gene expression may also be effected, for example, by virus-induced gene silencing (VIGS) in which an RNA-mediated antiviral defense mechanism is used. By the use of this system, plants are infected with virus vectors carrying inserts derived from host genes (e.g. sections of myb genes) and consequently the plant activates an antiviral defense mechanism which breaks down the viral expressed genes along with the identical endogenously expressed genes.

As depicted in detail in the example section which follows (see Example 4, hereinbelow), the present inventors have shown that downregulation of EOBI and EOBII in *Petunias* by VIGS (using SEQ ID NOs: 55 or 56, respectively) resulted in a significant reduction in internal pool levels (FIGS. 10A-B) and emission levels (FIG. 9F) of phenylpropanoid volatile compounds.

Thus, according to an embodiment of the present invention, down-regulating expression of a myb gene of the phenylpropanoid pathway is effected by expressing in the plant or plant cell an isolated polynucleotide comprising a nucleic acid sequence at least about 60%, at least about 65%, at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 93%, at least about 94%, at least about 95%, at least about 96%, at least about 97%, at least about 98%, at least about 99%, or more say 100% homologous to SEQ ID NOs: 55 or 56.

According to another exemplary embodiment, the isolated polynucleotide is as set forth by SEQ ID NOs: 55 or 56.

It will be appreciated that the genetically modified plants of the present invention are envisioned to exhibit modulated (e.g. enhanced or decreased) levels of scent emission.

According to an exemplary embodiment, the genetically modified plants of the present invention exhibit constant scent emission which is at least as high as that produced from a non-genetically modified plant of the same species during high scent emission hours (e.g. dark or light hours when scent production is typically at the highest level for the specific plant).

It will be appreciated that the genetically modified plants of the present invention may also comprise modulated (e.g. enhanced or decreased) taste and color.

The present invention also contemplates isolating the phenylpropanoid compounds from the genetically modified plants (as explained in detail hereinabove).

Thus, according to further embodiments of the invention, there is provided a method of plant extraction, the method comprising expressing in the plant a heterologous polynucleotide which produces a myb gene of the phenylpropanoid pathway and isolating a phenylpropanoid compound-containing fraction from the plant expressing the myb gene.

It will be appreciated that isolating the phenylpropanoid compound-containing fraction from the plant may be effected using any method known to one of ordinary skill in the art. For example, the emitted phenylpropanoid compounds may obtained by the use of an absorbent trap. According to this method (explained in detail in the materials and experimental procedures section in the Examples section which follows), volatiles emitted from detached flowers are collected using an adsorbent trap consisting of a glass tube containing 200 mg of Porapak Type Q polymer (80/100 mesh; Alltech, Deerfield, Ill.) held in place with plugs of silanized glass wool. Trapped volatiles are then eluted using 3 ml hexane (2 µg iso-butylbenzene may be added to each sample as an internal standard). Alternatively, internal pools of volatile compounds may be obtained, as for example from corolla limbs. According to a specific embodiment, the plant tissue is first obtained, then it is grounded (0.5-1.5 g FW) in liquid nitrogen and extracted in hexane (4 ml $g^{-1}$ of tissue) containing 0.5 µg $ml^{-1}$ iso-butylbenzene as the internal standard. Following an overnight incubation with shaking (at 150 rpm), extract is centrifuged at 10,500 g for 10 min and the supernatant is filtered through a 25 ml syringe with a 0.2 µM sterile nylon filter.

It will be appreciated that isolating the phenylpropanoid compound-containing fraction from the plant may be effected using any appropriate solvent known to one of ordinary skill in the art. Typically the solvent is chosen depending on the chemical characteristics of the compound/s of interest and/or the intended use of the compound, for example, hexane may be used for extraction of non-polar volatile compounds and methanol may be used for extraction of flavonoids [see e.g. Extraction, separation, and detection methods for phenolic acids and flavonoids, Stalikas, Constantine D. JOURNAL OF SEPARATION SCIENCE 30: 18 Pages: 3268-3295]. Other solvents which may be used according to the present teachings include, but are not limited to, glycerol, edible oil, cyclodextrin e.g. β-cyclodextrin and Methyl tert-butyl ether (MTBE) [as described in e.g. U.S. Pat. No. 5,073,267 fully incorporated herein by reference].

According to an embodiment of the invention, the isolated plant fraction has a phenylpropanoid compound profile as that of FIG. 2E closed bars.

The phenylpropanoid compounds isolated by the teaching of the present invention may be used to add taste and/or aroma to food products (e.g. herbal products), perfumery, air fresheners, cosmetics, cologne, detergent, soap, pharmaceuticals and to other commercial products.

It is expected that during the life of a patent maturing from this application many relevant myb genes will be developed and the scope of the term myb gene is intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Pap1 Expression in *Petunia* Leads to Increased Pigmentation and Scent

Materials and Experimental Procedures
Plant Material

*Petunia hybrida* 'Blue Spark' was used for the generation of transgenic plants. Plants were grown in a greenhouse under 22° C./16° C. day/night temperatures and natural photoperiod. Unless otherwise indicated, *petunia* flowers were collected at 2300 hours on the first night post-anthesis. For developmental analysis, buds and flowers were analyzed 120, 72 and 24 hours pre-anthesis (stages -5, -3 and -1, respectively), and 24, 48 and 72 hours post-anthesis (stages 1, 2 and 3, respectively). For day/night experiments, tissue was collected at two time points: 1100 hours and 2300 hours.

Construction of Chimeric Gene and Plant Transformation

Pap1 (GenBank accession no. AF325123) coding for Myb transcription factor (SEQ ID NO: 1) was cloned from *Arabidopsis* 'Colombia' DNA using PCR primers 5'-ATCTGCA-GACTTATACCTTTTACAATTTGTTTA-3' (SEQ ID NO: 3)

and 5'-TCAAACTGCAGAAACTAAGCCCA-3' (SEQ ID NO: 4). The amplified fragment was inserted into a pCd shuttle vector between the CaMV-35S promoter and OCS terminator and then the entire construct was inserted into binary vector pCGN1559 containing the neomycin phosphotransferase II gene (NptII) [Guterman et al. (2006) Plant Mol. Biol. 60: 555-563]. Binary vector pCGN1559 was also used for construction of pCGN7001 carrying the uidA gene encoding β-glucuronidase (GUS) driven by a mannopine synthetase promoter [Moyal Ben Zvi et al. (2008) Mol. Breeding. 22:543-553]. The constructs were transferred via *Agrobacterium tumefaciens* to *petunia* cv. Blue Spark using the standard leaf-disk transformation method (Guterman et al., supra).

RNA Analyses

Total RNA (10 μg) was isolated from control and transgenic plants (S1), fractionated through a 1% formaldehyde gel and transferred to a Hybond N+ membrane (Amersham-Pharmacia Biotech, Buckinghamshire, UK). $^{32}$P-labeled Pa1 (GenBank accession no. AY705976) (Rediprime; Amersham-Pharmacia Biotech) and S-adenosyl-L-methionine: benzoic acid/salicylic acid carboxyl methyltransferase (Bsmt1, GenBank accession no. AY233465) PCR fragments served as probes. Blots were hybridized in buffer consisting of 0.263 M Na2HPO4, 7% (w/v) SDS, 1 mM EDTA and 1% (w/v) BSA at 60° C., washed twice in 2×SSC, 0.1% SDS at 60° C. for 20 min each and exposed to X-ray film (Fuji, Tokyo, Japan) with two intensifying screens at −70° C. For semi-quantitative RT-PCR analyses, total RNA was treated with RNase-free DNase (Promega, Madison, Wis.) and cDNA was generated using oligo(dT)15 primer and M-MLV reverse transcriptase (both from Promega). Control samples were generated without addition of reverse transcriptase to the reaction.

The primers used for the semi-quantitative RT-PCR experiments were:

```
Pap1 (AF325123)
                                        (SEQ ID NO: 5)
5'-TTCCTACAACACCGGCACTAA-3'
and
                                        (SEQ ID NO: 6)
5'-TTTCTGTTGTCGTCGCTTCA-3', Epsp synthase (M21084)
                                        (SEQ ID NO: 7)
5'-TCATTACATGCTTGGTGCCTTG-3'
and
                                        (SEQ ID NO: 8)
5'-TTGGCTGCTAATGGATCCAGA-3', C4h (TC173066)
                                        (SEQ ID NO: 9)
5'-TTGTCAAATGTGGGAGCGTG-3'
and
                                        (SEQ ID NO: 10)
5'-TGGGATTCAAACCTGGCATC-3', Chs (X14599)
                                        (SEQ ID NO: 11)
5'-TCCCGGGGTGGAGGCATTCCAACCATT-3'
and
                                        (SEQ ID NO: 12)
5'-GGCCCTCGAGCATTCAAGACCTTCACCAG-3', Chi (Y00852)
                                        (SEQ ID NO: 13)
5'-ATGAATTCGGGATGTTGTTACAGGTC-3'
and
```

```
                                        (SEQ ID NO: 14)
5'-ATGAATTCTTTCTCGGTCTCCGGTTT-3',

F3h (X60512)
                                        (SEQ ID NO: 15)
5'-ATGAGCTCCACACTGATCCAGGAACC-3'
and
                                        (SEQ ID NO: 16)
5'-ATTCTAGATTACAACAGTAGGTAGGA-3', Dfr (X15537)
                                        (SEQ ID NO: 17)
5'-ATGACGTCGTTGGTCCATTCATCACA-3'
and
                                        (SEQ ID NO: 18)
5'-ATTCTAGAATGGCAATGGCTTCTCG-3', Paas (DQ243784)
                                        (SEQ ID NO: 19)
5'-ATCTCGAGCAACCCAGAATTTGATGGTCA-3'
and
                                        (SEQ ID NO: 20)
5'-AGAATTCACACCACCACCACCACCA-3', Actin (AA660796)
                                        (SEQ ID NO: 21)
5'-GGTTTTGCTGGGGATGATGC-3'
and
                                        (SEQ ID NO: 22)
5'-CATTGAATGTCTCAAACATG ATTTGAGTC-3'.
``` cDNA amplification was conducted with an initial denaturation step of 94° C. for 3 min, followed by 26 to 30 cycles of 94° C. for 10 s, 62° C. for 10 s, 72° C. for 20 s, and a final elongation step of 72° C. for 10 min. Actin cDNA was used as a reference for standardization of cDNA amounts in the reactions with different *petunia* lines. To confirm that analyzed samples were not contaminated with DNA, PCR amplification was also conducted with samples generated without reverse transcriptase.

Collection and GC-MS Analysis of Volatile Compounds

Volatiles emitted from detached *petunia* flowers were collected using an adsorbent trap consisting of a glass tube containing 200 mg of polymer Porapak Type Q (80/100 mesh; Alltech, Deerfield, Ill.) held in place with plugs of silanized glass wool (Guterman et al., 2006). Trapped volatiles were eluted using 3 ml hexane, and 2 μg iso-butylbenzene was added per sample as an internal standard for each. To determine pool sizes of volatile compounds, limbs were ground in liquid nitrogen and extracted in hexane (4 ml g$^{-1}$ of tissue) containing 0.5 μg ml$^{-1}$ iso-butylbenzene as the internal standard. Following overnight incubation with shaking at 150 rpm, extract was centrifuged at 10,500 g for 10 min and the supernatant filtered through a 25-ml syringe with a 0.2-μM sterile nylon filter. To assess whether the bound form of benzaldehyde accumulated in *petunia* limbs, tissue (0.6 g) was incubated with 9 ml phosphate citrate buffer pH 4.5 with or without 15 units of glucosidase mixture Novarom G (Novo Nordisk Ferment Ltd., Bagsvaerd, Denmark) at 37° C. overnight, and then transferred to −20° C. to stop enzymatic reactions. Hexane (10 ml) containing 0.5 μg ml$^{-1}$ iso-butylbenzene as an internal standard was added to each sample, and following vortexing, the upper phase was recovered.

GC-MS analysis was performed using a device composed of a Pa1 auto-sampler (CTC Analytic, Zwingen, Switzerland), a TRACE GC 2000 equipped with an Rtx-5SIL MS (Restek, i.d. 0.25 μm, 30 m×0.25 mm) fused-silica capillary column, and a TRACE DSQ quadrupole mass spectrometer (ThermoFinnigan, Hemel, UK). Helium was used as the carrier gas at a flow rate of 0.9 ml min$^{-1}$. The injection temperature was set to 250° C. (splitless mode), the interface to 280° C., and the ion source adjusted to 200° C. The analysis was performed under the following temperature program: 5 min of isothermal heating at 50° C., followed by a 5° C. min$^{-1}$ oven temperature ramp to 260° C., and a final increase from 250 to 280° C. at 10° C. min$^{-1}$. The transfer line temperature was 280° C. The system was equilibrated for 1 min at 70° C. before injection of the next sample. Mass spectra were recorded at 2 scan s$^{-1}$ with a scanning range of 40 to 450 mass-to-charge ratio, and an electron energy of 70 eV. Compounds were tentatively identified (>95% match) based on NIST/EPA/NIH Mass Spectral Library (Data Version: NIST 05, Software Version 2.0d) using the XCALIBUR v1.3 program (ThermoFinnigan) library. Further identification of compounds was based on comparison of mass spectra and retention times with those of authentic standards (Sigma, Milwaukee, Wis.) analyzed under similar conditions.

For evaluating the affect of Phe feeding on volatile production, control and Pap1-transgenic flowers were collected at 0800 hour and 1600 hour, placed in a glass vial containing 10 ml of water with or without 5 mg L-phenylalanine (Duchefa, Haarlem, Netherlands) and headspace was collected during the day (0800-1600 hours) and night (1600-0800 hours). To assess internal pools of volatiles, control and Pap1-transgenic flowers collected at 1600 hour were placed in a glass vial containing 10 ml of water with or without L-phenylalanine and at 2300 hour volatile were extracted as above.

Analytical Methods for Identification and Quantification of Non-Volatile Phenylpropanoid Compounds To determine the internal pool sizes of Phe, corolla limbs were extracted with methanol followed by phase separation with chloroform and water (10 ml methanol:5 ml chloroform:6 ml water). Amino acids in the aqueous phase were purified by Dowex-50-H+ ion-exchange chromatography. The pool size of Phe was quantified by GC-MS of N(O,S)-heptafluorobutyryl isobutyl amino acid derivatives, using -amino-n-butyrate as an internal standard. To determine the labeling of the endogenous non-volatile intermediate metabolites, limbs of control and Pap1-transgenic *petunia* were extracted with methanol and analyzed by LC-MS. Prior to injection into the mass spectrometer, extracted compounds were separated using a Supelco Discovery HS C18 column (15 cm×2.1 mm i.d.) attached to a Waters 2690 separations module (Milford, Mass.) with attached column oven. Compound elution was monitored at 210 and 280 nm with a Waters 996 UV/Vis photodiode array detector. Complete baseline separation was achieved at a flow rate of 0.25 ml min-1 with the column incubated at a constant temperature of 40° C. Solvent A was 0.05% formic acid in water; solvent B was 100% acetonitrile. The column was pre-equilibrated with 5% solvent B in solvent A. After injection of up to 25 µl of aqueous sample, the column was washed with 0.5 ml of pre-equilibration solvent. Compounds were eluted from the column with a linear gradient from 5% to 66% solvent B over 13.75 ml. The column was then washed by increasing solvent B to 100% (linear gradient in 0.75 ml) and holding at 100% solvent B for 0.75 ml. The column was then re-equilibrated by returning the column to 5% solvent B (over 0.75 ml) followed by a 2.5-ml wash with this solvent. Total run time was 70 min.

In-Vivo Isotope Labeling of Benzaldehyde

For stable isotope labeling of benzaldehyde, deuterium-labeled Phe (L-Phe-ring-2H5) purchased from Cambridge Isotope Laboratories (Andover, Mass.) was used. Newly synthesized labeled benzaldehyde exhibited a mass shift by 5 amu. The percentage of labeling was determined as the intensity of the shifted representative molecular ion divided by the sum of intensities for unshifted and shifted representative molecular ions. Benzaldehyde labeling was monitored at four time points: 45, 60, 120 and 240 min from 2H5-Phe feeding.

Anthocyanin Content

Corolla limbs were extracted in methanol containing 1% (v/v) HCl (100 mg tissue per 15 ml). Absorption values of the extract at A530 and A657 were measured to determine anthocyanin content using the formula A530-0.25A657, allowing for subtraction of chlorophyll interference.

Results

*Petunia hybrida* cv. Blue Spark was used, in contrast to the commonly studied white-flowering cv. Michelle [Quattrocchio et al., supra], because its flowers are pigmented. Constitutive 35S CaMV-driven expression of Pap1 in *petunia* had no negative effect on plant development and transgenic plants did not appear to be different from control plants with respect to growth rate, development, time to flowering or kinetics of flower senescence (data not shown). As expected, transgenic plants expressing Pap1 exhibited increased pigmentation levels (FIG. 1A) while transformation of *petunia* with the identical vector carrying the UidA gene coding for the β-glucuronidase (Gus) reporter gene (instead of Pap1) yielded only transgenic plants with true-to-type flower color (data not shown). Analyses of anthocyanin content in the corolla limbs of three independent transgenic lines revealed increased anthocyanin levels throughout flower development, up to nine-fold relative to limbs of control plants (FIG. 1B). Limbs of both control and Pap1-transgenic lines demonstrated similar developmental patterns of anthocyanin accumulation, peaking at around anthesis.

Transgenic Pap1 *petunia* flowers exhibiting enhanced pigmentation were noticeably more fragrant than control flowers. To quantitatively compare the floral-scent profile of transgenic and control *petunia* flowers, dynamic headspace analysis was conducted. Control flowers emitted the benzenoid compounds benzaldehyde and methylbenzoate. The emission of benzaldehyde, a common *petunia* scent compound, increased by three to five times in independent Pap1-transgenic lines as compared to the control flowers (FIGS. 2A-B). On the other hand, methylbenzoate emission levels, as well as expression levels of the gene responsible for its formation, were similar in Pap1-transgenic and control *petunia* flowers (FIGS. 2C-D).

The internal pool levels of benzaldehyde, as well as of benzyl alcohol, methylbenzoate and isoeugenol, were similar in transgenic flowers and in controls (FIGS. 2E-F). In contrast, internal pool levels of phenylacetaldehyde, benzaldehyde 4-hydroxy, benzaldehyde 3,4-dimethoxy (vanillin methyl ether) and benzaldehyde 4-hydroxy 3-methoxy (vanillin) were up to 10-fold higher in transgenic compared to control flowers (FIGS. 2E-F). Patterns of volatile accumulation and emission in transgenic and control flowers were similar throughout flower development (FIG. 3) as well as during the day/night cycle (FIGS. 4A-B).

Example 2

Pap1 Expression Leads to Increased Phenylalanine Utilization and Metabolic Flux in *Petunia*

Materials and Experimental Procedures
As described in detail in Example 1, hereinabove.
Results
To gain insight into the metabolic flux within the phenylpropanoid pathway in transgenic vs. control flowers and to assess substrate availability for volatile production, analysis of the levels of pathway intermediates was carried out. The internal pool size of phenylalanine (Phe) oscillated greatly between day and night in control flowers, with peak accumulation occurring at night (FIG. 5A). However, this nocturnal increase in Phe level was not observed in Pap1-transgenic flowers. In fact, night-time Phe levels were five- to sevenfold lower in transgenic vs. control flowers, whereas daytime Phe levels were only slightly affected (FIG. 5A). Levels of cinnamic and coumaric acid were similar in Pap1-transgenic and control flowers (FIGS. 6A-B).

Since L-Phe ammonia lyase (PAL), via catabolism of Phe, catalyzes a major branch point between primary and secondary metabolisms and hence can control flux in the phenylpropanoid pathway, Pa1's expression level was analyzed in transgenic and wild-type flowers. RNA-blot analyses revealed elevated Pa1 mRNA levels in Pap1 flowers compared to control flowers (FIG. 5B). To further evaluate whether the night-time depletion of the Phe pool in Pap1-transgenic flowers (FIG. 5A) is due to increased utilization of Phe, inventors used an in-vivo stable-isotope-labeling approach to monitor the rate of $^2H_5$-Phe conversion to benzaldehyde. $^2H_5$-Phe was more rapidly converted to benzaldehyde in transgenic flowers, resulting in 57% labeling of total benzaldehyde compared to 30% in the limbs of control flowers (FIG. 5C), and reflecting an 80% higher flux from Phe to benzaldehyde in the transgenic flowers.

Example 3

Abolishment of Nocturnal Rhythms of Scent Production Through Increased Phe Availability in Pap1 Transgenic Flowers Materials and Experimental Procedures
As described in detail in Example 1, hereinabove.
Results
To evaluate whether substrate availability limits volatile production in Pap1-transgenic flowers during the day, the volatiles produced in Pap1-transgenic vs. control flowers was examined following feeding of flowers with phenylalanine. Volatile accumulation and emission was unaffected in Pap1-transgenic flowers following Phe feeding during the night (FIGS. 7A-C), however, increased volatile emission was detected in Phe fed Pap1-transgenic flowers comparing with non-fed Pap1-transgenic flowers during the day (about 7-fold and 5-fold increase in benzaldehyde and methylbenzoate emission, respectively, FIGS. 7B-C). Volatile production in control flowers was not only unaffected by Phe feeding (FIGS. 7A-B), but even reduced (FIGS. 7A-B). The inhibitory effect of Phe feeding on volatile production in control flowers was most prominent during the night when reduction of about 2-3-fold in both benzaldehyde and methylbenzoate emission was detected (FIGS. 7B-C).

To examine the effect of Pap1 on the expression of genes downstream from Pa1 in the phenylpropanoid/benzenoid pathway (FIG. 8, namely, C4h coding for cinnamic acid-4-hydroxylase, Chs for chalcone synthase, Chi for chalcone isomerase, F3h for flavanone 3-hydroxylase, Dfr for dihydroflavonol-4-reductase, and Paas for phenylacetaldehyde synthase), semi-quantitative RT-PCR analysis was conducted using RNA isolated from transgenic and control flowers. Higher expression levels of C4h, involved in the formation of coumaric acid, were detected in Pap1-transgenic flowers, as were higher levels of Dfr and F3h, which are involved in later biochemical steps of the anthocyanin pathway. The expression of early anthocyanin biosynthetic genes (Chs and Chi) remained unaffected in transgenic flowers (FIG. 5D). The expression of Paas, a recently identified gene encoding the protein catalyzing phenylacetaldehyde biosynthesis (Kaminaga et al., supra), was strongly upregulated in Pap1-transgenic flowers compared to controls (FIG. 5D). It should be noted that phenylacetaldehyde levels were also markedly increased in the transgenic flowers (FIGS. 2E-F). Expression levels of 5-enolpyruvylshikimate 3-phosphate synthase (Epsp synthase), a well-characterized gene from the shikimate pathway involved in the formation of Phe was also determined. As evident from FIG. 5D, RNA levels of Epsp synthase were comparable in Pap1-transgenic and control *petunia* flowers.

Example 4

Identification and Isolation of EOBI and EOBII from *Petunia*

Materials and Experimental Procedures
Plant Material
Rooted plantlets of *Petunia hybrida* line P720 used for virus-induced gene silencing (VIGS) infection were obtained from Danziger—"Dan" Flower Farm (Mishmar Hashiva, Israel). Plants were grown in a greenhouse under 25° C./20° C. day/night temperatures and natural photoperiod. For dynamic headspace analysis, flowers were collected 2 days post-anthesis (dpa) at 17:00 h.
Plasmid Construction
The myb-like fragments were isolated by RT-PCR using as a template RNA from flowers of *Petunia hybrida* line P720 and degenerate primers R2f and R3r. Primers were designed complementary to the conserved amino acid sequences KKGPWTPEE, SEQ ID NO: 23 (5'-AAGAAAGCN-SCWTGGCANSMNGMAGAA-3', SEQ ID NO: 24) and DNEIKNYWN, SEQ ID NO: 25 (5'-TTCCARTRRTTNTT-NAYNTCRTTRTC-3', SEQ ID NO: 26) of the R2R3MYB motifs. The PCR products were cloned into pGEMT-Easy (Promega) and subjected to DNA sequencing. Subsequently, the fragments were transferred to Tobacco rattle virus-based (TRV), pTRV2 and pTRV2-CHS (chalcone synthase) constructs [Spitzer et al., (2007) Plant Physiol. 145: 1241-1250] for functional analyses. EOBs (Emission of Benzenoids), EOBI (GenBank accession no: EU360892, SEQ ID NO: 51) and EOBII (GenBank accession no: EU360893, SEQ ID NO: 53), were PCR cloned using petunia cDNA library and primers based on the sequence of myb-like fragment EOB (primers used for EOB1: FEOB1 and Rp1, REOB1 and Fp1; primers used for EOB2: FEOB2 and Rp1, REOB2 and Fp1, see Table 7, hereinbelow).

To generate pTRV2-CHS (Spitzer et al., supra) containing 3' region of EOBI and pTRV2-CHS containing 3' region of EOBII, 85 bp (from 689-773) from EOBI (SEQ ID NO: 55) and 205 bp (from 669-873) from EOBII (SEQ ID NO: 56), respectively—were PCR amplified and inserted upstream of CHS in pTRV2-CHS.

To construct EOBI and EOBII fused to GFP, the respective open reading frames 606 bp (from 1-606) and 591 bp (from 1-591) were PCR amplified with addition of HpaI in the forward primer (HPAFE1 and HPAFE2, see Table 7, hereinbelow) and the addition of nucleotides encoding amino acids glycin-prolyin-glycin in the reverse primer (GPGRE1 and GPGRE2, see Table 7, hereinbelow). The amplification product was inserted into pGEMT-Easy (Promega). Subsequently the EOBI and EOBII sequences were cloned into pTRV-GFP to generate pTRV2-EOBI:GFP and pTRV2-EOBII:GFP.

TABLE 7

PCR primers

| Primer name | Sequence (5' to 3') | SEQ ID NO: |
|---|---|---|
| HPAFE1 | AACGAGATGGATAAAAGAACATGCAATTCTCA | 41 |
| HPAFE2 | AACGAGATGGATAAAAAACCATGCAACTCTCA | 42 |
| GPGRE1 | TCCTGGTCCGTTGGTTGCATCATTAAGCAATTG | 43 |
| GPGRE2 | TCCTGGTCCATCACCATTAAGCAATTGCATGG | 44 |
| FEOB1 | GAACTGCATGCTAAGTGGG | 45 |
| Rp1 | GACTCGAGTCGACATCG | 46 |
| REOB1 | AATGTACGTGATCAACATTTAAACTCTTTACA | 47 |
| Fp1 | GATTTAGGTGACACTATAGGGAGACC | 48 |
| FEOB2 | GAACTGCATGCTAAGTGGG | 49 |
| REOB2 | GACCACCTGTTTCCCCACTTAGC | 50 |

Agroinoculation of TRV Vectors

*Agrobacterium tumefaciens* (strain AGLO) transformed with pTRV1, pTRV2 and pTRV2 derivatives were prepared as described previously [Liu et al. (2002) Plant J 31: 777-786]. The *Agrobacterium* culture was grown overnight at 28° C. in LB medium with 50 mg/L kanamycin and 200 µM acetosyringone. The cells were harvested and resuspended in inoculation buffer containing 10 mM MES, 200 µM acetosyringone and 10 mM $MgCl_2$ to an $OD_{550}$ of 10. Following an additional 3 h of incubation at 28° C., the bacteria with the pTRV1 was mixed with the bacteria containing the pTRV2 derivates in a 1:1 ratio; 200-400 µl of this mixture was injected into the stem or applied on the cut surface after removing the apical meristems of *petunia* plantlets. For the pTRV2-EOBI:GFP and pTRV2-EOBII:GFP seedlings of *Nicotiana benthamiana* (3 weeks old) were infected by leaf infiltration using syringe (Liu et al., supra). Transient expression of GFP fusions in *Nicotiana benthamiana* epidermis was evaluated using an epi-florescence microscope IX8 (Olympus, Japan) 36 h after infection.

Collection and GC-MS Analysis of Volatile Compounds

Volatiles emitted from detached *petunia* flowers were collected using an adsorbent trap consisting of a glass tube containing 200 mg of Porapak Type Q polymer (80/100 mesh; Alltech, Deerfield, Ill.) held in place with plugs of silanized glass wool as was previously described [Guterman et al. (2006) Plant Molecular Biology 60: 555-563]. Trapped volatiles were eluted using 3 ml hexane, and 2 µg iso-butylbenzene was added to each sample as an internal standard.

To determine the pool sizes of volatile compounds in corolla limbs, tissue (0.5-1.5 g FW) was ground in liquid nitrogen and extracted in hexane (4 ml $g^{-1}$ of tissue) containing 0.5 µg $ml^{-1}$ iso-butylbenzene as the internal standard. Following overnight incubation with shaking at 150 rpm, extract was centrifuged at 10,500 g for 10 min and the supernatant filtered through a 25 ml syringe with a 0.2 µM sterile nylon filter.

GC-MS analysis was performed using a device composed of a Pa1 auto-sampler (CTC Analytic, Zwingen, Switzerland), a TRACE GC 2000 equipped with an Rtx-5SIL MS (Restek, i.d. 0.25 µm, 30 m×0.25 mm) fused-silica capillary column, and a TRACE DSQ quadrupole mass spectrometer (ThermoFinnigan, Hemel, UK). Helium was used as the carrier gas at a flow rate of 0.9 ml/min. The injection temperature was set to 250° C. (splitless mode), the interface to 280° C., and the ion source adjusted to 200° C. The analysis was performed under the following temperature program: 2 min of isothermal heating at 40° C. followed by a 10° C./min oven temperature ramp to 250° C. The transfer line temperature was 280° C. The system was equilibrated for 1 min at 70° C. before injection of the next sample. Mass spectra were recorded at 2.65 scans with a scanning range of 40 to 450 mass-to-charge ratio, and an electron energy of 70 eV. Compounds were tentatively identified (higher than 95% match) based on NIST/EPA/NIH Mass Spectral Library (Data Version: NIST 05, Software Version 2.0d) using the XCALIBUR v1.3 program (ThermoFinnigan) library. Further identification of major compounds was based on comparison of mass spectra and retention times with those of authentic standards (Sigma) analyzed under similar conditions.

Real-Time PCR Analysis

*Petunia* total RNA was extracted using Tri-reagent™ kit (Molecular Research Center Inc., Cincinnati, Ohio), and treated with RNase-free DNase (Fermentas, Vilnius, Lithuania). First-strand cDNA was synthesized using 1 µg of total RNA, oligo d(T) primer and Reverse transcriptase ImProm-II™ (Promega, Palo Alto, Calif.).

PCR was performed for 40 cycles (94° C. for 15 min and then cycling: 94° C. for 10 sec; 60° C. for 30 sec and 72° C. for 20 sec). Real-time PCR primers for EOBI amplification were 5'-TTCTCCATCTTCATACACTGGAAATA-3' (SEQ ID NO: 27) and 5'-GCTAGGCAGCTAGATTACTGATT-3' (SEQ ID NO: 28), primers for EOBII were 5'-TTGAGT-TAAACCCTAGATTGAACC-3' (SEQ ID NO: 29) and 5'-AGTTTGTTGTATTACACGATGACCA-3' (SEQ ID NO: 30). Theses primers were unable to amplify EOBI and EOBII fragments cloned in pTRV2.

For C4H amplification the primers were 5'-TTGTCAAAT-GTGGGAGCGTG-3' (SEQ ID NO: 31) and 5'-TGGGAT-TCAAACCTGGCATC-3' (SEQ ID NO: 32). For BPBT, 5'-TGTTGAAGGGTGATGCTCAA-3' (SEQ ID NO: 33) and 5'-GGATTTGGCATTTCAAACAAA-3' (SEQ ID NO: 34). For PAL2,5'-TGCTAATGGTGAACTTCATCCA-3' (SEQ ID NO: 35) and 5'-TGACATTCTTCT-CACTTTCACCA-3' (SEQ ID NO: 36) and for FHT, 5'-GC-CTTAACCAAGGCATGTGT-3' (SEQ ID NO: 37) and 5'-TAGCTTGAAGCCCACCAACT-3' (SEQ ID NO: 38). The transcript level of *Nicotiana tabacum* ACTIN (GenBank accession no. U60495) was amplified with primers 5'-TGCT-GATCGTATGAGCAAGGAA-3' (SEQ ID NO: 39) and 5'-GGTGGAGCAACAACCTTAATCTTC-3' (SEQ ID NO: 40) and was used as reference for standardization of cDNA amounts. Real-time quantitative PCR reactions were performed in the presence of SYBR® Green I (ABgene, Epsom, UK) dye on a Corbett Research Rotor-Gene™ 6000 cycler, and data analysis was performed using Rotor-Gene 6000 series software 1.7.

Phylogenetic Analysis

Tree was generated by Neighbor joining method in AlignX of vector NTI Advance 9.0.

The alignment was created using the Clustal W algorithm using AlignX of vector NTI Advance 9.0.

Results

To generate a collection of PCR products of putative regulatory factors from *petunia* flowers (line P720) inventors used degenerate primers to R2R3, RWD, WRKY, bHLH and EPF (see materials and experimental procedures section, hereinabove), among others, domains present in transcription factors belonging to the R2R3 Myb, basic helixloop-helix, WD40 and zinc-finger protein families. As a template, inventors used reverse-transcribed RNA prepared from *petunia* flowers, 1 and 2 days post-anthesis, when scent production was high. This collection of sequenced fragments was then screened for their relevance to scent production, using virus-induced gene silencing (VIGS) system. Full-length sequences of the genes tentatively identified as scent-related were then cloned. Two of these newly identified and cloned genes, belonging to the Myb transcription factor family, were named EOBI and EOBII (Emission of Benzenoids; GB: EU360892 and EU360893, respectively). Both protein sequences contained the SANT/MYB DNA-binding domains, indicative of Myb-type transcription factors.

Discoloration of *petunia* corollas (FIGS. 9B-D) showed successful VIGS silencing by pTRV2-CHS, pTRV2-CHS-EOBI and pTRV2-CHS-EOBII, respectively, as compared to a control *petunia* infected with an empty TRV2 construct (FIG. 9A). Furthermore, to assess the involvement of EOB genes in regulating flavonoid biosynthesis, *petunia* plantlets were infected with TRV (lacking CHS) containing EOBI fragment (from nucleotide at position 102 to position 390 TRV-EOB) with a conserved sequence for both EOBI and EOBII (93.4% identity). As evident from FIG. 9E, no effect on anthocyanin pathway was noticeable by infection with the conserved sequence (the infected plants did not have any visual phenotype change). Suppression of both EOBI and EOBII was verified in petals of infected *petunia* plants as determined by transcript levels (FIG. 9H).

Flowers of petunia plants infected by TRV-CHS vector fused to sequences tentatively named EMISSION OF BENZENOIDS I (EOBI) (TRV-CHS:EOBI) and EMISSION OF BENZENOIDS II (EOBII) (TRV-CHS:EOBII) emitted reduced levels of volatiles from the Phenylpropanoid pathway such as benzaldehyde, benzyl alcohol, phenylethyl alcohol, benzyl acetate (for EOBII silencing only), eugenol, vanillin, isoeugenol, and benzylbenzoate (FIG. 9F). The levels of emitted volatile monoterpens such as limonene and pinene did not change (FIG. 9G).

To further evaluate the effect of EOBs on benzenoid volatiles, internal pools of phenylpropanoids was analyzed in TRV-CHS:EOBI and TRV-CHS:EOBII infected *petunia* flowers. The internal pools of the majority of phenylpropanoid volatiles including benzaldehyde, benzyl alcohol, phenylacetaldehyde, benzylacetate, eugenol, vanillin and benzylbenzoate, in the petals harvested from the TRV-CHS: EOBI and TRV-CHS:EOBII infected plants was much lower compared to control TRV-CHS inoculated flowers (FIGS. 10A-B), indicating that benzenoid volatile production (rather then release) is affected by EOBI and II. Specificity of EOBs to benzenoid volatiles was further demonstrated by the observation that levels of fatty acid derived volatile ethyl hexanol (FIG. 10A) were not affected in TRV-CHS:EOBI and TRV-CHS:EOBII infected flowers.

Suppression of EOBI and EOBII in petals of plants infected with TRV-CHS: EOBI and TRV-CHS:EOBII, respectively, was confirmed using real-time PCR. As showed in FIG. 11, the transcript levels of EOBI and EOBII in petals of TRV-CHS:EOBI and II infected plants was approximately 40% and 15%, respectively, of that in control TRV-CHS infected flowers. To rule out unspecific silencing of EOBI in flowers with suppressed EOBII and vise versa, inventors analyzed the levels of EOBII in flowers inoculated with TRV-CHS:EOBI and levels of EOBI in flowers inoculated with TRV-CHS:EOBII. As shown in FIG. 11, the silencing was specific and no cross silencing between EOBI and II was observed. The mRNA level of EOBI and II did not change in flowers of plants infected with TRV-CHS:EOBII and TRV-CHS:EOBI, respectively. as detected by real-time RT-PCR.

Example 5

Temporal and Spatial Expression Profile of EOB Genes

Materials and Experimental Procedures
As described in detail in Example 4, hereinabove.
Results To characterize EOBI and EOBII expression, the transcript levels of both was analyzed in *petunia* flowers at different stages of development, at various time points during the day and night and in different organs and tissues. This was done using real-time RT-PCR. mRNA was extracted from flower corollas at different developmental stages: from a young 1.5 cm bud to flowers at senescence. As shown in FIGS. 12A and 12B, the levels of EOBI and EOBII transcripts increased parallel to bud development. The EOBII transcript accumulated to the highest level in flowers at anthesis, levels of EOBI transcript peak 1 day post anthesis. GC-MS headspace analysis of the emission pattern of volatile phenylpropanoids during flower development revealed that the level of phenylpropanoid volatile emission mimics EOBs expression, thus, the level of volatiles increased parallel to flower development, peaking at 2 DPA and then decreases in senescing flowers (FIG. 12C).

Analysis of EOBs relative expression in different plant organs further suggested an involvement of EOBs in floral scent production. Thus, the level of both EOBI and EOBII transcripts was flower specific and negligible levels were detected in roots, stem, leaf and sepals (FIGS. 12D-E). The highest level of EOB expression was found in the corolla, less in flower pistil and even lower in flower tube and stamens (FIGS. 12D-E).

Analysis of the diurnal expression pattern of EOBs revealed it to be rhythmic, as could be expected for scent related genes. The transcript levels were highest in the early morning hours and lowest during late afternoon hours (FIGS. 12F-G). Furthermore, the peak in EOBs expression preceded scent production by several hours (FIG. 12H), again as can be expected of scent regulating factors.

Example 6

EOB Encodes for a R2R3MYB Domain

Materials and Experimental Procedures
As described in detail in Example 4, hereinabove.
Results Sequence analysis of EOBI and EOBII cDNA showed an ORF encoding a 202 amino acid (SEQ ID NO: 52) and a 197 amino acid (SEQ ID NO: 54) protein, respectively (FIG. 13A). Database analysis showed that the predicted proteins contained the conserved MYB R2R3 binding domain near its N-terminal end. Another R2R3MYB-like gene *Arabidopsis* AtPAP1 was shown herein to activate the production of volatile phenylpropanoids in *petunia* flowers (Examples 1-2, hereinabove).

Moreover, at the end of the C-terminal region of EOBI and EOBII there was a W-MDDIW motif (SEQ ID NO: 57, FIG. 13A) that has been previously shown to comprise major importance in trans-activation [Li et al. (2006) Biochemical and Biophysical Research Communications 341: 1155-1163]. EOBI and EOBII belong to subgroup 19 of MYB R2R3 transcription factors as divided previously on the basis of motif comparison outside of the binding domain [Kranz et al. (1998) The Plant Journal 16: 263-276]. Other members of this group of genes share high homology to the EOB genes and contain the W-MDDIW motif (SEQ ID NO: 57). These include AmMYB305, AmMYB340, PsMYB26 and AtMYB21 (FIGS. 13A and B) which are also predominantly expressed in flowers, are involved in the regulation of the general Phenylpropanoids pathway and are most likely regulated by light [Li et al., supra; Moyano et al. (1996) Plant Cell 8: 1519-1532; Uimari and Strommer (1997) Plant Journal 12: 1273-1284]. The closest relatives of *petunia* EOB genes are MYB305 from ornamental tobacco; VvMYBX4, GmMYB99,98,182,181, with unknown function; PsMYB26, AmMYB340 and AmMYB305 (FIG. 13B) that regulate the phenylpropanoid pathway in floral tissues. The two last genes directly activate PAL as was concluded by their ability to bind to the PAL promoter and activate a reporter gene fused to the PAL promoter in yeast and protoplasts [Sablowski et al. (1994) Embo Journal 13: 128-137; Moyano et al., supra; Uimari and Strommer, supra]. Other related proteins are GhMYB8 with an unknown function; AtMYB21 that activates PAL transcription, regulated by COP1 and its expression has been shown to be flower specific [Shin et al. (2002) The Plant Journal 30: 23-32; Li et al., supra). AtMYB24 has also been shown to be flower specific and regulates the phenylpropanoid genes. AtMYB24 expression is most likely induced by dark and it's over expression resulted in up-regulation of PAL2 and C4h and suppression of CHS and DFR transcript levels in *Arabidopsis* (Li et al., supra). It is worth noting that phylogenetically EOBI and EOBII are distant from PhODO1 (FIG. 13B).

Example 7

EOB Genes are Localized to the Nucleus

Materials and Experimental Procedures
As described in detail in Example 4, hereinabove.
Results
As was described above (Example 6), EOB genes were shown to belong to the MYB transcription factors and hence they are expected to be localized to the nucleus. To confirm nuclear localization of EOBI and EOBII, inventors constructed EOBI:GFP and EOBII:GFP (green fluorescent protein fusion proteins) and followed their expression. Microscopy analyses localized the GFP's fluorescence in both cases to the nucleus (FIGS. 14A-H).

Example 8

EOBI and EOBII Regulate the Phenylpropanoid Pathway

Materials and Experimental Procedures
As described in detail in Example 4, hereinabove.
Results
To further detail the effect of EOBI and EOBII on scent production, inventors analyzed the expression levels of genes involved in floral scent production in pTRV2-CHS:EOBI- and pTRV2-CHS:EOBII-suppressed *petunia* flowers as compared to control "empty" pTRV2-CHS-suppressed flowers. As can be seen in FIG. 15A, the level of the transcript coding for cinnamate 4-hydroxylase (C4H), an enzyme involved in the production of the volatiles e.g. iso-eugenol, eugenol and vaneline, was down regulated in EOBI silenced flowers, as compared to control flowers. In EOBII silenced flowers, benzoyl-CoA:benzyl alcohol/phenylethanol benzoyltransferase (BPBT), an enzyme involved in the production of volatile benzenoids, was strongly down-regulated (FIG. 15B). Moreover, the level of L-phenylalanine ammonia lyase 2 (PAL2) transcript was down regulated in EOBII-suppressed flowers (FIG. 15C). To further evaluate specificity of EOBI and EOBII to benzenoid volatile production, inventors analyzed the level of FHT a transcript encoding flavanone 3-hydroxylase, a key enzyme in the early unbranched segment of the flavonoid biosynthetic pathway. FHT levels were unaffected in EOBI and EOBII-suppressed flowers relative to control flowers (FIG. 15D) further demonstrating the specificity of EOBI and II to benzenoid volatile production.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of enhancing production of a scent-related benzanoid compound in a plant or plant cell, the method comprising expressing in the plant or plant cell an exogenous polynucleotide encoding an EOBI polypeptide having an amino acid sequence at least 95% identical to SEQ ID NO: 52, said polypeptide comprising a myb R2R3 bind in/domain near the N-terminus and a W-MDDIW motif near the C-terminus of said polypeptide, thereby enhancing the production of the benzanoid compound in the plant or plant cell, and wherein said benzanoid compound is selected from the group consisting of phenylacetaldehyde, ethylbenzene, benzaldehyde, methylbenzoate, isoeuglenol, benzyl alcohol, phenylethyl alcohol, vanillin and benzyl benzoate.

2. The method of claim 1, wherein said scent-related benzanoid compound is benzaldehyde.

3. The method of claim 1, wherein said exogenous polynucleotide is as set forth in SEQ ID NO: 51.

4. The method of claim 1, wherein said EOBI polypeptide is as set forth in SEQ ID NO: 52.

5. The method of claim 1, wherein said scent-related compound is phenylacetaldehyde.

6. The method of claim 1, wherein said benzanoid compound is methylbenzoate.

7. The method of claim 1, wherein said plant or plant cell further has enhanced emission of a scent-related benzanoid compound selected from the group consisting of benzaldehyde, benzyl alcohol, phenylethyl alcohol, vanillin, euglenol, isoeuglenol and benzyl benzoate.

8. The method of claim 7, wherein said cent-related benzanoid compound is phenylethyl alcohol.

9. The method of claim 7, wherein said scent-related benzanoid compound is vanillin.

10. The method of claim 7, wherein said scent-related benzanoid compound is euglenol.

11. The method of claim 7, wherein said scent-related benzanoid compound is isoeuglenol.

12. The method of claim 7, wherein said scent-related benzanoid compound is benzyl benzoate.

* * * * *

SEQUENCE LISTING

<160> NUMBER OF SEQ ID NOS: 62

<210> SEQ ID NO 1
<211> LENGTH: 7918
<212> TYPE: DNA
<213> ORGANISM: Arabidopsis thaliana

<400> SEQUENCE: 1

```
ggtaccttag attatccaaa tttgtagctg caaaagttgt tcctgtgttc aagaaagaaa        60
gacctgtaaa atgatctgga tgtgtttggt tatatatata agaagactta aaagataatg       120
acttaatctc gtaacgagtc acacggacgt gacgctgaaa ctcacacacg ttggtgccac       180
gtctttgtct ttcctctttt gctctacttt tttctcctca taggtgatag gtcccataag       240
```

-continued

```
caatgaaata aaaaaaatgg taattgactt ttctccaaac attttcgaat ctgattttct      300
ttttcaaggt tttataacct ctacattcca gaatatgact aatgcatca  ttatccaatt      360 attttttata ctgtaaactc attattatga atattcttta tttcaaaaaa ttaccattga      420
tttataagtt tattagtata atatataaca tatggaataa aacttttatt taaaaaaaaa      480 tattttccc  caaaaaagt  aggattaata acctgattaa taaataaaaa gtgttatatt      540
tttaagcatt gtatgcattt actttatcat agttgtcttg ttttaagag  ttaaaaaata     600 atgatgaaca atttcacgga caacgattcc acgataaagc tttccctgca acactcagat      660
tttctaaaga cggttttgca ttgcgttttc tgggattcga acccaaaca  tgatgtacaa      720 gtattaatga actcttagtt aaccattaga ttaaaaatat tttcactatt aattttctct      780
taaaaatatt aataattttt tgaaatcaaa aattatagtt attttatttt aataaacgag      840
aaacactaca aaaaaagtta actgcattta gataatttaa taaactaaaa tatccacata      900
aaaatttcaa atttatcaaa aataaaacat caatttgttt tttgtttttaa attaaagatt     960 tgctattgat tgcataagga agaaaacttt acaaagccga aaggcctaag agcccaacac     1020
acacaaaaga agaaccattt tggatcaagg gaaccgacca tgggtattag aagtagtggt     1080
ataaagccca tcatatccca acacataacc cacgaatgtt taatattaaa agtttgttgt     1140
tcggctcatg attagcgatg atcatacaga aagtttgtat ctaatacgtg ccttgaattt     1200
tatgtgtaca acaaacaaat taaattattc aaaaccataa attataaaaa ataattacag     1260
aaataaaact atattaagag cgagcctacc atccggtgtg caactttcta gtttatatac     1320
agtggcggat caacgttaat gaggcaaatt ggttcaaatt catctaaata agactagagt     1380
tcacaggttc gattcctcct tataacaatt tgctcccacc aatttttttt gctgggtccg     1440
cccctggtta tatatatact tctacaccag gtttgggttc gagtccacac ataattaacg     1500
acacaattat agtgcacgat agaatgaact aaaacagcta gagcgtagag ggctcattgt     1560
ctataaaaat ccttcgttaa cttgcaagaa accaagagta gagggctcac acttaagtct     1620
cctacatgac gattatattt cgtcaaaaag aagcaattag ttagctttac agcatatcat     1680
ttcgcctagg ttttccatcg tacacgtaaa ttttcatgca agaaagcaga aatatacaaa     1740
tactaacttt tagatactga aaatgagat  cagattctag tcaaattttg ttaaaagtat     1800
ttataaattt aaattgcaag tcctcaaaaa gtacgactaa aaatgctttt cttagaaaat     1860
gataataaac cggcgtttta tatataagtg tttcttttc  tcttctgtcc agaagtaaat     1920
cattaagaac caatatggct tttcttaaac taatctccgt gataatcaaa tctttgatca     1980
ttctccacac aatcccatca acaacatcga tctcactaga tgcaccaaca atgattctaa     2040
tcggcactac taactataga gatagttgtc ccaaaaaaaa aaaaaaaaac taactagaga     2100
gataaatcat attcaataca tgtactattt ctactatact taagaaaatt tgtataccac     2160
tatcttaact cttaacactg aacatactat acactatctt aactcccaac tcttgtaaaa     2220
gaatatctaa ttttaagaaa agacttcaaa tgcttgttaa atttctagtg aagatgcaca     2280
ttctaaaaac tggtaaaatg gtaagaaaaa aatatataaa aaaatagcct tattaaaatt     2340
tatatctcct atttctctat ccaaactaca cggatgaagc ttattgttat tcatccaccc     2400
tttttctcaa ttctgtccta tttcttgtgc atgaaacttc tccatcttgt aatcggataa     2460
atcataccca aatttttct  ttctgaaaac atatatacc  gaacattaat tactatcgtc     2520
ctttctccta attttgttaa gaaacatgtt tgtttgtttt tagtactgaa aaaggatgga     2580
gatacttgct agatcctatg aacctttttct ctctaggaca aatcagtaac caaacaataa     2640
```

```
cttagcaaat taagcacgac agctaataca taaaatgtgg atatcaaaca tgcacgtcac   2700 ttccttttt  ccgtcacgtg tttttataaa ttttctcaca tactcacact ctctataaga   2760
cctccaatca tttgtgaaac catactatat ataccctctt ccttgaccaa tttacttata   2820 cctttacaa  tttgtttata tattttacgt atctatcttt gttccatgga gggttcgtcc   2880
aaagggctgc gaaaaggtgc ttggactact gaagaagata gtctcttgag acagtgcatt   2940
aataagtatg gagaaggcaa atggcaccaa gttcctgtaa gagctggtat gttatttacg   3000
aacacacaca cactaaccga cacacacaca cacaaatatg aatatctata atcactacca   3060
atagtcttcg ttctctctat tttctattca gaaaattgat taatacccgg tattaaaaaa   3120 aaaaaaaaa  atttgtttaa atgagtacaa atcattgtta caacttcttt atgctgtttt   3180
tacatgctat taaaggttgt gcatgaaaat ttcttttgct gttcgtattt gtttacacc    3240 taaacgaaga tttttactta aaattaaaga aaaaaatta  tactaatttt agttacgttg   3300
cgtattgcta gcttctccta taaagtcgtt caaatttta  cacgcttgtc ttcttgtaaa   3360
tgaattcgtg ggaaaattt  gtatgaacac gtgtttctgt gttggaacag ttctttattt   3420
ttattggtgt gcatagattc ttcctgataa aatatataga aggagacaaa taaaaaacag   3480
tcttagtatg taggtataat caaagaatca attattggtt ttgtagggct aaaccggtgc   3540
aggaaaagtt gtagattaag atggttgaac tatttgaagc caagtatcaa gagaggaaaa   3600
cttagctctg atgaagtcga tcttcttctt cgccttcata ggcttctagg aataggtat    3660 taattgttac ctcgatacta cttaactcgg agagtcgtca taagttaata ctaataacat   3720
atgtatattt tcttacaatt gttaggtggt ctttaattgc tggaagatta cctggtcgga   3780
ccgcaaatga cgtcaagaat tactggaaca ctcatctgag taagaaacat gaaccgtgtt   3840
gtaagataaa gatgaaaaag agagacatta cgcccattcc tacaacaccg gcactaaaaa   3900
acaatgttta taagcctcga cctcgatcct tcacagttaa caacgactgc aaccatctca   3960
atgccccacc aaaagttgac gttaatcctc catgccttgg acttaacatc aataatgttt   4020
gtgacaatag tatcatatac aacaaagata agaagaaaga ccaactagtg aataatttga   4080
ttgatggaga taatatgtgg ttagagaaat tcctagagga aagccaagag gtagatattt   4140
tggttcctga agcgacgaca acagaaaagg gggacacctt ggcttttgac gttgatcaac   4200
tttggagtct tttcgatgga gagactgtga aatttgatta gtgtttcgaa catttgtttg   4260
cgtttgtgta taggtttgct ttcacctttt aatttgtgtg ttttgataaa taagctaata   4320 gttttagca  ttttaatgaa atatttcaag tttccgtgtt tacattttga agaaaataaa   4380
atattaatat attctgaaga ttttttgttt ttttttggtta tctacatgac aacagtaaaa   4440
atagaaaaaa aatcttatt  tttgaaaaag gtatgtatcc ggtgtttaga atactttccg   4500
aaatcaaacc gcctatattt ctaatcacta tgtaaaattg taaaccaatt gggttaaaac   4560
tcaactaaca aactttctaa ataaatgtca ttttgtttt  caaatatgat tgaactcgga   4620
tttaggagtt ttaccttca  gtaccaaacc ttctctaccg accatgtatg gttgggcaaa   4680
tgtcatgttt tacaatgttt agattactaa acactttggt tgagaaggca atgctttatt   4740
tatatattct gaagtcatgt tttagtgtta ttttatta   tttttaaatg catagattgt   4800
taacgtgcag attctcatat gggcttagtt tctggatttt gattatcaaa accgtattcc   4860
actcttaaat gattacgaca aaaaaatcaa tactactaac aaacctatttt cccagttatt   4920 aattagtcaa taacaattgt caaatttaat aacgtacttg ctagtaataa agttttaacg   4980
acgatcatag ataggttttt gaaacccata ctcgcagaag ttctgataca aaaatttgta   5040
```

```
ctccctctat ttcaaaatat taaatgtttt agataaaagc acaatgttta agaaactaat    5100
taatcttgag tttcttacat tataaacata aattaatatc tattaaaaat aatttgacca    5160
atgatataac ttacagcata atataaatag ttaaaaaaaa actgtttact ttaataattt    5220
gcataacaac tagctagtct ggtccaagaa cggtagtagg atgagatttt agaaggtcgt    5280
aatgtgtaag actaataatc atgcgataga cgatcatgca tgaattattt tatgtaatac    5340
ttatatggtt ccaaaatcta taagaaccct caattataaa agtaatatct attaaatatt    5400
taaacgataa tttcatacgg aaaattaata gataaattct tctatttgtt tttaaatata    5460
tgtaaatgcg aaagtgtccc atgcaatttt atatatttaa tcaagtgaaa actcgaaaac    5520
aaaaaacttg atgtacttca acaagttttt tttggcaagt aatacccatt ctgttccggt    5580
tggactataa atgcatggaa aagcaccaaa aaaggcatgg atactttcgc gattttttgcc    5640
attttttgtat ctttgttcat cgctccgttc aaaagaacct cttgtcgtta ctataataag    5700
ttatggacca acggtattgt catgtatcaa ataactatg tagcatacgt gtattgtgaa    5760
tcaatgaagc aatagagaga taacatactg aaacgtccac atctcgttta taaaaaaatc    5820
gtctacatgc ttctctttgg ctggacatcc caacttttct caccgtaacc agtgaaattg    5880
tattatttgg taagaattac ggatggagtt agatttatttt tgttgtgtgt gtataaatca    5940
atacttatac agttttttacg tgtataacgg cacgcctcat gggttttgct aataaggtcc    6000
aagtagtgga cagaaaagaa cttgtgattg aatagtgttt tgtattgaaa ggttaaaacg    6060
tgtttccaaa tggattcaac caaattccaa catgttcagt gtcgtacatg cgaaaacatt    6120
atcgagtaaa ataagttcca ttatactttg attttgtatt gattccatag agtagaaatg    6180
tgtgctttag cttatagtta aacactatct tcaagggggt aatgctggat tcgaagtatt    6240
taattagtcc tgttcgaccg aatcaaagtt caatcgattt tgaaaaacaa tcatttcggg    6300
tatagcttga aacatcccaa accacaagtt ccaaaagcac acatattatc accattcaac    6360
taaccattcg ggtttgataa ccggtagttg gatgttcaaa gatctcatca gatttggtgt    6420
caagaggata attgtgattg agttgtgaac ccttgtgatg gagatagttt ccttgtttgg    6480
atgttaagtt gaattttggg atcatccttg tttcaaaaag actggaaaac acacaaaaaa    6540
aaaaaaaaaa aaacttgcaa ataaatttaa tttttagaaa ttttatattg tagtgaaaaa    6600
tgtttgcaaa ttttagctgg agatgttttt ccatttggaa tttttttttct taattttgcc    6660
ttttatttta cattgtatat tgctagcttc ttcttgacaa gaaagaacga tgtcaacctc    6720
tgatttgtct tcttataaat gaatttgttg aaaattgctg tacgagcaag tgttttttgtg    6780
ttggaacatg tctctatttc tattggtgtg catagattct tcatgataaa atatataagg    6840
agacaaataa gaaagcagtc ttattaggta ggattgccta aaatattcgt tagattcgct    6900
tggatctatt attcggttaa attgattcga aaaatctgaa tatccataat tttacgaagc    6960
aaatcaaata ttaaaaattg atattcgtta aaaacagaaa aaataacaaa tattaaatttt    7020
aaataggcgg atatcctctc taattcggta tacatgaata tatgtatatg tatatagata    7080
agtataaata tatatattaa taatcttact cttttttatat gtaagtttta gaagtttatg    7140
ttcatcaaat tagttatttta actattagtt taaaaaattg aaaagagata ttttttccaa    7200
tgaagttttta cttattttgg attaaatttc taattttttat gttttttaatt tttataattg    7260
tttttgagat atacttaaca aatcgaatat ctagcaaata actcggattt taacggaata    7320
tctggacagc cggatattcg gttactttcg aaacaaatac gaatcagaaa actaattatt    7380
ccgatatagc aaatcggatc acaaatacta ccaaaatcca tgatatatgt gtcgtgtcca    7440
```

```
cccctattag taggtataat taattgtaat tagtggtttt gtaagactaa atcagcccag    7500
gaagagttgt agactaagat gcttatacta tttgaagcca agtatcaaga gaggaagatt    7560
taggctctga tgaagttgat cttcttcttc gccttcccaa ccttctagga aatagtattt    7620
gttatacttt atactaatta attacttcgg gattcataag attattaata acatattatt    7680
cgtataatgt ttaacaactt ttagattggc tttgattgct ggtctattgg ctggtcagac    7740
cacaaacggt gtcaaaaatt acttgaacac tcaactgagt aagaaacatg aaccatgttg    7800
taagatttag ataaaaaaaa aaaaaaagca ttacttccaa tgctaccata ctgggctaaa    7860
aatggatgtt tttaatctcg accttaatcc ttctcattta acagcagtgg cctaccaa     7918
```

<210> SEQ ID NO 2
<211> LENGTH: 248
<212> TYPE: PRT
<213> ORGANISM: Arabidopsis thaliana

<400> SEQUENCE: 2

```
Met Glu Gly Ser Ser Lys Gly Leu Arg Lys Gly Ala Trp Thr Thr Glu
1               5                   10                  15

Glu Asp Ser Leu Leu Arg Gln Cys Ile Asn Lys Tyr Gly Glu Gly Lys
            20                  25                  30

Trp His Gln Val Pro Val Arg Ala Gly Leu Asn Arg Cys Arg Lys Ser
        35                  40                  45

Cys Arg Leu Arg Trp Leu Asn Tyr Leu Lys Pro Ser Ile Lys Arg Gly
    50                  55                  60

Lys Leu Ser Ser Asp Glu Val Asp Leu Leu Leu Arg Leu His Arg Leu
65                  70                  75                  80

Leu Gly Asn Arg Trp Ser Leu Ile Ala Gly Arg Leu Pro Gly Arg Thr
                85                  90                  95

Ala Asn Asp Val Lys Asn Tyr Trp Asn Thr His Leu Ser Lys Lys His
            100                 105                 110

Glu Pro Cys Cys Lys Ile Lys Met Lys Lys Arg Asp Ile Thr Pro Ile
        115                 120                 125

Pro Thr Thr Pro Ala Leu Lys Asn Asn Val Tyr Lys Pro Arg Pro Arg
    130                 135                 140

Ser Phe Thr Val Asn Asn Asp Cys Asn His Leu Asn Ala Pro Pro Lys
145                 150                 155                 160

Val Asp Val Asn Pro Pro Cys Leu Gly Leu Asn Ile Asn Asn Val Cys
                165                 170                 175

Asp Asn Ser Ile Ile Tyr Asn Lys Asp Lys Lys Asp Gln Leu Val
            180                 185                 190

Asn Asn Leu Ile Asp Gly Asp Asn Met Trp Leu Glu Lys Phe Leu Glu
        195                 200                 205

Glu Ser Gln Glu Val Asp Ile Leu Val Pro Glu Ala Thr Thr Thr Glu
    210                 215                 220

Lys Gly Asp Thr Leu Ala Phe Asp Val Asp Gln Leu Trp Ser Leu Phe
225                 230                 235                 240

Asp Gly Glu Thr Val Lys Phe Asp
                245
```

<210> SEQ ID NO 3
<211> LENGTH: 33
<212> TYPE: DNA
<213> ORGANISM: Artificial sequence
<220> FEATURE:
<223> OTHER INFORMATION: Single strand DNA oligonucleotide

```
<400> SEQUENCE: 3
atctgcagac ttatacctttt tacaatttgt tta                           33

<210> SEQ ID NO 4
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 4
tcaaactgca gaaactaagc cca                                       23

<210> SEQ ID NO 5
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 5
ttcctacaac accggcacta a                                         21

<210> SEQ ID NO 6
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 6
tttctgttgt cgtcgcttca                                           20

<210> SEQ ID NO 7
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 7
tcattacatg cttggtgcct tg                                        22

<210> SEQ ID NO 8
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 8
ttggctgcta atggatccag a                                         21

<210> SEQ ID NO 9
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 9
ttgtcaaatg tgggagcgtg                                           20

<210> SEQ ID NO 10
<211> LENGTH: 20
<212> TYPE: DNA
```

```
<213> ORGANISM: Artificial sequence
<220> FEATURE:
<223> OTHER INFORMATION: Single strand DNA oligonucleotide

<400> SEQUENCE: 10
tgggattcaa acctggcatc                                              20

<210> SEQ ID NO 11
<211> LENGTH: 27
<212> TYPE: DNA
<213> ORGANISM: Artificial sequence
<220> FEATURE:
<223> OTHER INFORMATION: Single strand DNA oligonucleotide

<400> SEQUENCE: 11
tcccggggtg gaggcattcc aaccatt                                      27

<210> SEQ ID NO 12
<211> LENGTH: 29
<212> TYPE: DNA
<213> ORGANISM: Artificial sequence
<220> FEATURE:
<223> OTHER INFORMATION: Single strand DNA oligonucleotide

<400> SEQUENCE: 12
ggccctcgag cattcaagac cttcaccag                                    29

<210> SEQ ID NO 13
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 13
atgaattcgg gatgttgtta caggtc                                       26

<210> SEQ ID NO 14
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 14
atgaattctt tctcggtctc cggttt                                       26

<210> SEQ ID NO 15
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 15
atgagctcca cactgatcca ggaacc                                       26

<210> SEQ ID NO 16
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 16
attctagatt acaacagtag gtagga                                       26
```

<210> SEQ ID NO 17
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 17
atgacgtcgt tggtccattc atcaca                                      26

<210> SEQ ID NO 18
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 18
attctagaat ggcaatggct tctcg                                       25

<210> SEQ ID NO 19
<211> LENGTH: 29
<212> TYPE: DNA
<213> ORGANISM: Artificial sequence
<220> FEATURE:
<223> OTHER INFORMATION: Single strand DNA oligonucleotide

<400> SEQUENCE: 19
atctcgagca acccagaatt tgatggtca                                   29

<210> SEQ ID NO 20
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 20
agaattcaca ccaccaccac cacca                                       25

<210> SEQ ID NO 21
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 21
ggttttgctg gggatgatgc                                             20

<210> SEQ ID NO 22
<211> LENGTH: 29
<212> TYPE: DNA
<213> ORGANISM: Artificial sequence
<220> FEATURE:
<223> OTHER INFORMATION: Single strand DNA oligonucleotide

<400> SEQUENCE: 22
cattgaatgt ctcaaacatg atttgagtc                                   29

<210> SEQ ID NO 23
<211> LENGTH: 9
<212> TYPE: PRT
<213> ORGANISM: Artificial sequence
<220> FEATURE:
<223> OTHER INFORMATION: Conserved MYB motif amino acid sequence
      according to which a degenerate primer was designed

<400> SEQUENCE: 23

Lys Lys Gly Pro Trp Thr Pro Glu Glu
1               5

<210> SEQ ID NO 24
<211> LENGTH: 27
<212> TYPE: DNA
<213> ORGANISM: Artificial sequence
<220> FEATURE:
<223> OTHER INFORMATION: Single strand DNA oligonucleotide
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t

<400> SEQUENCE: 24
aagaaagcns cwtggcansm ngmagaa                                          27

<210> SEQ ID NO 25
<211> LENGTH: 9
<212> TYPE: PRT
<213> ORGANISM: Artificial sequence
<220> FEATURE:
<223> OTHER INFORMATION: Conserved MYB motif amino acid sequence
      according to which a degenerate primer was designed

<400> SEQUENCE: 25

Asp Asn Glu Ile Lys Asn Tyr Trp Asn
1               5

<210> SEQ ID NO 26
<211> LENGTH: 26
<212> TYPE: DNA
<213> ORGANISM: Artificial sequence
<220> FEATURE:
<223> OTHER INFORMATION: Single strand DNA oligonucleotide
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 26
ttccartrrt tnttnayntc rttrtc                                           26

<210> SEQ ID NO 27
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 27
ttctccatct tcatacactg gaaata                                           26

<210> SEQ ID NO 28
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 28
gctaggcagc tagattactg att                                            23

<210> SEQ ID NO 29
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 29
ttgagttaaa ccctagattg aacc                                           24

<210> SEQ ID NO 30
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 30
agtttgttgt attacacgat gacca                                          25

<210> SEQ ID NO 31
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 31
ttgtcaaatg tgggagcgtg                                                20

<210> SEQ ID NO 32
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 32
tgggattcaa acctggcatc                                                20

<210> SEQ ID NO 33
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 33
tgttgaaggg tgatgctcaa                                                20

<210> SEQ ID NO 34
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 34
ggatttggca tttcaaacaa a                                     21

<210> SEQ ID NO 35
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 35
tgctaatggt gaacttcatc ca                                    22

<210> SEQ ID NO 36
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 36
tgacattctt ctcactttca cca                                   23

<210> SEQ ID NO 37
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 37
gccttaacca aggcatgtgt                                       20

<210> SEQ ID NO 38
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 38
tagcttgaag cccaccaact                                       20

<210> SEQ ID NO 39
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 39
tgctgatcgt atgagcaagg aa                                    22

<210> SEQ ID NO 40
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 40
ggtggagcaa caaccttaat cttc                                  24

<210> SEQ ID NO 41
<211> LENGTH: 32
<212> TYPE: DNA

```
<213> ORGANISM: Artificial sequence
<220> FEATURE:
<223> OTHER INFORMATION: Single strand DNA oligonucleotide

<400> SEQUENCE: 41
aacgagatgg ataaaagaac atgcaattct ca                              32

<210> SEQ ID NO 42
<211> LENGTH: 32
<212> TYPE: DNA
<213> ORGANISM: Artificial sequence
<220> FEATURE:
<223> OTHER INFORMATION: Single strand DNA oligonucleotide

<400> SEQUENCE: 42
aacgagatgg ataaaaaacc atgcaactct ca                              32

<210> SEQ ID NO 43
<211> LENGTH: 33
<212> TYPE: DNA
<213> ORGANISM: Artificial sequence
<220> FEATURE:
<223> OTHER INFORMATION: Single strand DNA oligonucleotide

<400> SEQUENCE: 43
tcctggtccg ttggttgcat cattaagcaa ttg                             33

<210> SEQ ID NO 44
<211> LENGTH: 32
<212> TYPE: DNA
<213> ORGANISM: Artificial sequence
<220> FEATURE:
<223> OTHER INFORMATION: Single strand DNA oligonucleotide

<400> SEQUENCE: 44
tcctggtcca tcaccattaa gcaattgcat gg                              32

<210> SEQ ID NO 45
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 45
gaactgcatg ctaagtggg                                             19

<210> SEQ ID NO 46
<211> LENGTH: 17
<212> TYPE: DNA
<213> ORGANISM: Artificial sequence
<220> FEATURE:
<223> OTHER INFORMATION: Single strand DNA oligonucleotide

<400> SEQUENCE: 46
gactcgagtc gacatcg                                               17

<210> SEQ ID NO 47
<211> LENGTH: 32
<212> TYPE: DNA
<213> ORGANISM: Artificial sequence
<220> FEATURE:
<223> OTHER INFORMATION: Single strand DNA oligonucleotide

<400> SEQUENCE: 47
aatgtacgtg atcaacattt aaactcttta ca                              32
```

```
<210> SEQ ID NO 48
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 48
gatttaggtg acactatagg gagacc                                          26

<210> SEQ ID NO 49
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 49
gaactgcatg ctaagtggg                                                  19

<210> SEQ ID NO 50
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 50
gaccacctgt ttccccactt agc                                             23

<210> SEQ ID NO 51
<211> LENGTH: 790
<212> TYPE: DNA
<213> ORGANISM: Petunia x hybrida

<400> SEQUENCE: 51
ttaaaacaac tagttttaca acccatctct cttctcttgt tttttcctc tcttaaaaca       60 aaatggataa agaacatgc aattctcaag atgttgaagt taggaaaggt ccttggacta      120
tggaagaaga tttaattctc ataaactata tagctaatca tggtgaaggt gtttggaatt     180
ccttagctcg atctgctggt ctaaagcgta ccggaaaaag ttgtcgactt cggtggctta     240
attatctccg gccagatgtc cggaggggaa atattcaccc tgaagaacag ctcttgatta     300
tggaactgca tgctaagtgg ggaaacaggt ggtcaaaaat tgcaaagcat tgccaggaa      360 gaactgataa tgagataaag aattattgga ggactaggat acagaagcac attaataagc     420
aagcagatca aaacatgaag aaacaatcaa aatgtgagca caatgatcaa caagcaatta     480
gtacaagtca agtatctact ggtcctacag ataccattga ctcctattct ccatcttcat     540
acactggaaa tactaataat aatatggaaa atattacctt tcatggcaat tttccaactg     600
aaacaaatga aaatatttgg agcatagaag atctctggtc cttgcaattg cttaatgatg     660
caaccaacta attataatta atcagtaatc tagctgccta gcaattatta tgtaaagagt     720
ttaaatgttg atcacgtaca ttatctttt atgtctattc ttcttcgtga gtcaaaaaaa     780
aaaaaaaaaa                                                            790

<210> SEQ ID NO 52
<211> LENGTH: 202
<212> TYPE: PRT
<213> ORGANISM: Petunia x hybrida

<400> SEQUENCE: 52
```

```
Met Asp Lys Arg Thr Cys Asn Ser Gln Asp Val Glu Val Arg Lys Gly
1               5                   10                  15

Pro Trp Thr Met Glu Glu Asp Leu Ile Leu Ile Asn Tyr Ile Ala Asn
            20                  25                  30

His Gly Glu Gly Val Trp Asn Ser Leu Ala Arg Ser Ala Gly Leu Lys
        35                  40                  45

Arg Thr Gly Lys Ser Cys Arg Leu Arg Trp Leu Asn Tyr Leu Arg Pro
    50                  55                  60

Asp Val Arg Arg Gly Asn Ile Thr Pro Glu Glu Gln Leu Leu Ile Met
65                  70                  75                  80

Glu Leu His Ala Lys Trp Gly Asn Arg Trp Ser Lys Ile Ala Lys His
                85                  90                  95

Leu Pro Gly Arg Thr Asp Asn Glu Ile Lys Asn Tyr Trp Arg Thr Arg
            100                 105                 110

Ile Gln Lys His Ile Asn Lys Gln Ala Asp Gln Asn Met Lys Lys Gln
        115                 120                 125

Ser Lys Cys Glu His Asn Asp Gln Gln Ala Ile Ser Thr Ser Gln Val
    130                 135                 140

Ser Thr Gly Pro Thr Asp Thr Ile Asp Ser Tyr Ser Pro Ser Ser Tyr
145                 150                 155                 160

Thr Gly Asn Thr Asn Asn Asn Met Glu Asn Ile Thr Phe His Gly Asn
                165                 170                 175

Phe Pro Thr Glu Thr Asn Glu Asn Ile Trp Ser Ile Glu Asp Leu Trp
            180                 185                 190

Ser Leu Gln Leu Leu Asn Asp Ala Thr Asn
    195                 200

<210> SEQ ID NO 53
<211> LENGTH: 895
<212> TYPE: DNA
<213> ORGANISM: Petunia x hybrida

<400> SEQUENCE: 53
atcttcactc cctatcccat ctctttctct ctctccctct ccctttttt ccttcatctc     60
ttaaaaaaga tggataaaaa accatgcaac tctcaagatg ctgaagtgag gaaaggacct    120
tggactatgg aagaagattt aattctcata aactacattg ctaatcatgg tgaaggtgtt    180
tggaattcct tagctaaatc tgctggtctc aaacgtaccg ggaaaagttg tcggcttcgg    240
tgcttaatt atctccggcc tgatgtccgg aggggcaata ttacacctga gaacaacttt    300
tgattatgg aactgcatgc taagtgggga acaggtggtc gaaaattgc gaagcatttg    360
cctggaagaa cagataatga aataaagaac tattggagga ctagaattca gaagcacatt    420
aagcaagcag aaaccatgaa tggacaagca gcttcttcag agcaaaatga tcatcaagaa    480
gcttgcacta gccaaatgtc taatggtcca atgacaata ccattgatca gacctactct    540
cccacttcat actctggaaa tgtggacact ttccaagcag gccctaattt tctcactgaa    600
gcaaatgaca acatgtggag catggaagac atctggtcca tgcaattgct taatggtgat    660
taagtatttt gagttaaacc ctagattgaa ccatctcatg agtgagtacg tactacaaaa    720
agttaagcct ctagttagct agttttatat agtgctaata ttttgcatta tatatccccc    780
atatatgtga gttaagtggt cattgtgtaa tacaacaaac tcttatataa ccctgttcat    840
ataatatata gatgcatgga ggtgcctatg gttatattaa aaaaaaaaaa aaaaa         895

<210> SEQ ID NO 54
<211> LENGTH: 197
```

-continued

```
<212> TYPE: PRT
<213> ORGANISM: Petunia x hybrida

<400> SEQUENCE: 54

Met Asp Lys Lys Pro Cys Asn Ser Gln Asp Ala Glu Val Arg Lys Gly
1               5                   10                  15

Pro Trp Thr Met Glu Glu Asp Leu Ile Leu Ile Asn Tyr Ile Ala Asn
            20                  25                  30

His Gly Glu Gly Val Trp Asn Ser Leu Ala Lys Ser Ala Gly Leu Lys
        35                  40                  45

Arg Thr Gly Lys Ser Cys Arg Leu Arg Trp Leu Asn Tyr Leu Arg Pro
    50                  55                  60

Asp Val Arg Arg Gly Asn Ile Thr Pro Glu Glu Gln Leu Leu Ile Met
65                  70                  75                  80

Glu Leu His Ala Lys Trp Gly Asn Arg Trp Ser Lys Ile Ala Lys His
                85                  90                  95

Leu Pro Gly Arg Thr Asp Asn Glu Ile Lys Asn Tyr Trp Arg Thr Arg
            100                 105                 110

Ile Gln Lys His Ile Lys Gln Ala Glu Thr Met Asn Gly Gln Ala Ala
        115                 120                 125

Ser Ser Glu Gln Asn Asp His Gln Glu Ala Cys Thr Ser Gln Met Ser
    130                 135                 140

Asn Gly Pro Asn Asp Asn Thr Ile Asp Gln Thr Tyr Ser Pro Thr Ser
145                 150                 155                 160

Tyr Ser Gly Asn Val Asp Thr Phe Gln Ala Gly Pro Asn Phe Leu Thr
                165                 170                 175

Glu Ala Asn Asp Asn Met Trp Ser Met Glu Asp Ile Trp Ser Met Gln
            180                 185                 190

Leu Leu Asn Gly Asp
        195

<210> SEQ ID NO 55
<211> LENGTH: 85
<212> TYPE: DNA
<213> ORGANISM: Artificial sequence
<220> FEATURE:
<223> OTHER INFORMATION: 3' region of EOBI (from 689-773) inserted into
      pTRV2-CHS

<400> SEQUENCE: 55
tctagctgcc tagcaattat tatgtaaaga gtttaaatgt tgatcacgta cattatcttt    60
ttatgtctat tcttcttcgt gagtc                                         85

<210> SEQ ID NO 56
<211> LENGTH: 205
<212> TYPE: DNA
<213> ORGANISM: Artificial sequence
<220> FEATURE:
<223> OTHER INFORMATION: 3' region of EOBII (from 669-873) inserted
      into pTRV2-CHS

<400> SEQUENCE: 56
ttgagttaaa ccctagattg aaccatctca tgagtgagta cgtactacaa aaagttaagc    60
ctctagttag ctagttttat atagtgctaa tattttgcat tatatatccc ccatatatgt   120
gagttaagtg gtcattgtgt aatacaacaa actcttatat aaccctgttc atataatata   180
tagatgcatg gaggtgccta tggtt                                        205

<210> SEQ ID NO 57
```

```
<211> LENGTH: 7
<212> TYPE: PRT
<213> ORGANISM: Artificial sequence
<220> FEATURE:
<223> OTHER INFORMATION: W-MDDIW motif sequence
<220> FEATURE:
<221> NAME/KEY: misc_feature
<222> LOCATION: (2)..(2)
<223> OTHER INFORMATION: Xaa can be any naturally occurring amino acid

<400> SEQUENCE: 57

Trp Xaa Met Asp Asp Ile Trp
1               5

<210> SEQ ID NO 58
<211> LENGTH: 1028
<212> TYPE: DNA
<213> ORGANISM: Solanum lycopersicum

<400> SEQUENCE: 58
aactacaaaa aaaaaaaaaa cttttttctt cacatcccat tcctcttctc ttctttatta      60
tataaaaaaa atggataaaa gaacatgtga ttctcaagat gttgaagtta ggaaaggtcc     120
ttggactatg gaagaagatt tgattctcat caattacatt gctaatcatg gtgaaggtgt     180
ttggaattcc ctcgctcgat ccgctggtac taattgatcg tcatgtttag attggggctt     240
aattatgttg tatatattta atttttttcg tgtgtaatag gtttgaagcg tactggaaaa     300
agttgtagac ttagatggct taattatctc cgacctgatg ttcggagggg aaatattaca     360
ccggaggaac aattgttgat catggaacta catgccaagt ggggaaaccg gtgagttgat     420
ttctttttct agctagggtt ttgataatta ataaaatga tgaaattata taaaagaaaa      480
tttgaaaaat tgtagaaatt tctccttcat tttttttaaaa atgaaaaata aaaaaaatct    540
cccatgtgtt tgtatgtgtt ggatggataa agaggaattg tcccaaaatc tcttagaact    600
agatttgaca tcatgaaaga gagtgatggg gaatttacaa cgtgtttaat gtaacctaaa    660
gtttggattt tttatttatt tatgatttct tattgggtgt caaaagtatt cttcttaata   720
attaattttt tttattgagg attaactcat tttcccttct tttcttccct aaaatttgtt    780
gaaatcctta gttttttttcc attcaaaaaa ttaatccgat cataatatca aatttataat   840
gaatagacct aatcttctat tactcctatc attttttatc ttacttttat ttttaatttg    900
tttcaaaaag tctctgttat tgttattttt ttaacaaaat tttaattcta aattttcgta    960
tgatattttt aagatcacaa tatttttaata tattacacat gtctttagtt tataatacat   1020
aattcaaa                                                              1028

<210> SEQ ID NO 59
<211> LENGTH: 89
<212> TYPE: PRT
<213> ORGANISM: Solanum lycopersicum

<400> SEQUENCE: 59

Met Asp Lys Arg Thr Cys Asp Ser Gln Asp Val Glu Val Arg Lys Gly
1               5                   10                  15

Pro Trp Thr Met Glu Glu Asp Leu Ile Leu Ile Asn Tyr Ile Ala Asn
            20                  25                  30

His Gly Glu Gly Val Trp Asn Ser Leu Ala Arg Ser Ala Gly Leu Lys
        35                  40                  45

Arg Thr Gly Lys Ser Cys Arg Leu Arg Trp Leu Asn Tyr Leu Arg Pro
    50                  55                  60

Asp Val Arg Arg Gly Asn Ile Thr Pro Glu Glu Gln Leu Leu Ile Met
```

```
                65                  70                  75                  80
Glu Leu His Ala Lys Trp Gly Asn Arg
                85

<210> SEQ ID NO 60
<211> LENGTH: 106
<212> TYPE: PRT
<213> ORGANISM: Petunia x hybrida
<220> FEATURE:
<221> NAME/KEY: misc_feature
<223> OTHER INFORMATION: EOBI R2R3

<400> SEQUENCE: 60

Glu Val Arg Lys Gly Pro Trp Thr Met Glu Glu Asp Leu Ile Leu Ile
1               5                   10                  15

Asn Tyr Ile Ala Asn His Gly Glu Gly Val Trp Asn Ser Leu Ala Arg
            20                  25                  30

Ser Ala Gly Leu Lys Arg Thr Gly Lys Ser Cys Arg Leu Arg Trp Leu
        35                  40                  45

Asn Tyr Leu Arg Pro Asp Val Arg Arg Gly Asn Ile Thr Pro Glu Glu
    50                  55                  60

Gln Leu Leu Ile Met Glu Leu His Ala Lys Trp Gly Asn Arg Trp Ser
65                  70                  75                  80

Lys Ile Ala Lys His Leu Pro Gly Arg Thr Asp Asn Glu Ile Lys Asn
                85                  90                  95

Tyr Trp Arg Thr Arg Ile Gln Lys His Ile
            100                 105

<210> SEQ ID NO 61
<211> LENGTH: 106
<212> TYPE: PRT
<213> ORGANISM: Petunia x hybrida
<220> FEATURE:
<221> NAME/KEY: misc_feature
<223> OTHER INFORMATION: EOBII R2R3

<400> SEQUENCE: 61

Glu Val Arg Lys Gly Pro Trp Thr Met Glu Glu Asp Leu Ile Leu Ile
1               5                   10                  15

Asn Tyr Ile Ala Asn His Gly Glu Gly Val Trp Asn Ser Leu Ala Lys
            20                  25                  30

Ser Ala Gly Leu Lys Arg Thr Gly Lys Ser Cys Arg Leu Arg Trp Leu
        35                  40                  45

Asn Tyr Leu Arg Pro Asp Val Arg Arg Gly Asn Ile Thr Pro Glu Glu
    50                  55                  60

Gln Leu Leu Ile Met Glu Leu His Ala Lys Trp Gly Asn Arg Trp Ser
65                  70                  75                  80

Lys Ile Ala Lys His Leu Pro Gly Arg Thr Asp Asn Glu Ile Lys Asn
                85                  90                  95

Tyr Trp Arg Thr Arg Ile Gln Lys His Ile
            100                 105

<210> SEQ ID NO 62
<211> LENGTH: 104
<212> TYPE: PRT
<213> ORGANISM: Arabidopsis thaliana
<220> FEATURE:
<221> NAME/KEY: misc_feature
<223> OTHER INFORMATION: PAP1 R2R3

<400> SEQUENCE: 62
```

```
Leu Arg Lys Gly Ala Trp Thr Thr Glu Glu Asp Ser Leu Leu Arg Gln
1               5                   10                  15

Cys Ile Asn Lys Tyr Gly Glu Gly Lys Trp His Gln Val Pro Val Arg
            20                  25                  30

Ala Gly Leu Asn Arg Cys Arg Lys Ser Cys Arg Leu Arg Trp Leu Asn
            35                  40                  45

Tyr Leu Lys Pro Ser Ile Lys Arg Gly Lys Leu Ser Ser Asp Glu Val
        50                  55                  60

Asp Leu Leu Leu Arg Leu His Arg Leu Leu Gly Asn Arg Trp Ser Leu
65                  70                  75                  80

Ile Ala Gly Arg Leu Pro Gly Arg Thr Ala Asn Asp Val Lys Asn Tyr
                85                  90                  95

Trp Asn Thr His Leu Ser Lys Lys
            100
```